(12) United States Patent
Liao

(10) Patent No.: US 11,365,188 B2
(45) Date of Patent: Jun. 21, 2022

(54) JAK INHIBITORS

(71) Applicant: Xibin Liao, Edison, NJ (US)

(72) Inventor: Xibin Liao, Edison, NJ (US)

( * ) Notice: Subject to any disclaimer, the term of this patent is extended or adjusted under 35 U.S.C. 154(b) by 0 days.

(21) Appl. No.: 16/979,455

(22) PCT Filed: Mar. 18, 2019

(86) PCT No.: PCT/US2019/022657
§ 371 (c)(1),
(2) Date: Sep. 9, 2020

(87) PCT Pub. No.: WO2019/182924
PCT Pub. Date: Sep. 26, 2019

(65) Prior Publication Data
US 2021/0053943 A1 Feb. 25, 2021

Related U.S. Application Data

(60) Provisional application No. 62/646,167, filed on Mar. 21, 2018.

(51) Int. Cl.
*C07D 403/04* (2006.01)
*A61K 45/06* (2006.01)

(52) U.S. Cl.
CPC ............ *C07D 403/04* (2013.01); *A61K 45/06* (2013.01)

(58) Field of Classification Search
CPC ... C07D 471/02; C07D 471/10; A61K 31/496
See application file for complete search history.

(56) References Cited

U.S. PATENT DOCUMENTS

| 2014/0336207 A1 | 11/2014 | Zhang et al. |
| 2016/0045508 A1 | 2/2016 | Vazquez et al. |
| 2017/0247373 A1 | 8/2017 | Masse et al. |

FOREIGN PATENT DOCUMENTS

WO  WO-2018169700 A1 * 9/2018 ............. A61K 45/06

OTHER PUBLICATIONS

Chough, C. et al. Design, synthesis and evaluation of (R)-3-(7-(methyl(7H-pyrrolo[2, 3-d]pyridin-4-yl)-5-azaspiro[2.4]heptan-5-yl)-3-oxopropanenitrile as JAK1-selective inhibitor, Medicinal Chemistry Communications 9, pp. 477-489, Jan. 15, 2018.
Supplementary European Search Report from EP 19770607 dated Jul. 8, 2021.

\* cited by examiner

*Primary Examiner* — Theodore R. Howell
*Assistant Examiner* — George W Kosturko
(74) *Attorney, Agent, or Firm* — SZDC Law P.C.

(57) ABSTRACT

Janus kinases (JAKs) inhibitors have the following Formula (I):

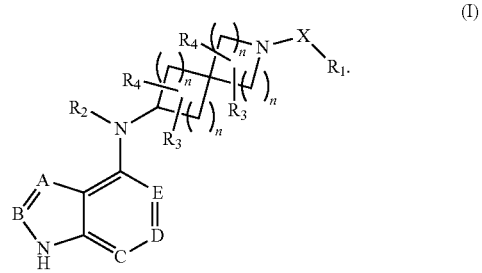

14 Claims, No Drawings

JAK INHIBITORS

This application is the National Stage Application of PCT/US2019/022657, filed on Mar. 18, 2019, which claims priority to U.S. Provisional Patent Application No. 62/646,167, filed on Mar. 21, 2018, which is incorporated by reference for all purposes as if fully set forth herein.

FIELD OF THE INVENTION

The present invention relates to certain new compounds, or pharmaceutically acceptable salts, as well as their compositions and methods of use, that inhibit the activity of Janus kinases (JAKs) and are useful in the treatment of disease related to the activity of JAKs including, for example, inflammatory disorders, autoimmune disorders, cancer, and other diseases.

BACKGROUND OF THE INVENTION

Janus kinases (JAKs) is a family of intracellular, nonreceptor tyrosine kinases that transduce cytokine-mediated signals via the JAK-STAT pathway. The four known mammalian JAK family members are: Janus kinase 1 (JAK1), Janus kinase 2 (JAK2), Janus kinase 3 (JAK3), and Tyrosine kinase 2 (TYK2).

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses whether classically allergic reactions or not.

JAK1 plays a critical role in mediation of biological responses and JAK1 is widely expressed and associated with several major cytokine receptor families. It is involved in signaling by members of the IL-2 receptor family (IL-2, IL-4, IL-7R, IL-9R, IL-15R, and IL-21R), the IL-4 receptor family (IL-4R, IL-13R), the gp130 receptor family and class II cytokine receptors. JAK1 also mediates the activation of signal transducer and activator of transcription 3, STAT3. Persistent STAT3 activation is tumorigenic and promotes cancer cell survival and proliferation. Inhibition of JAK1 is continually needed for developing new and more effective pharmaceuticals that are aimed at the immune and inflammatory pathways, as well as agents for the prevention and treatment of autoimmune diseases, hyperactive inflammatory response, allergies, cancer and some immune reactions caused by other therapeutics. Inhibition of JAK1 can block STAT3 activation resulting in tumor growth inhibition and tumor immune surveillance. In addition, activating JAK1 mutations have been identified in both T-lineage acute lymphoblastic leukemia and Asian hepatocellular carcinoma and have been demonstrated as oncogenic.

JAK2 is known to form homodimers that mediate EPO and TPO receptor-signaling to the STAT5 pathway, which regulates red blood cells and platelet production. Inhibition of JAK2 can result in anemia and thrombocytopenia.

JAK1 and JAK2 have high degree of structural similarity. JAK1 inhibitors may also inhibit JAK2. Compounds that selectively inhibit JAK1 may have a better hepatotoxicity and immunogenicity profile than compounds that selectively inhibit JAK2 or JAK1/2 dual inhibitors.

There remains a need to provide JAK1 inhibitors that selectively inhibits JAK1 and reduce or avoid JAK2 and JAK3 inhibition. The compounds of the invention, as well as its compositions and methods described herein are directed toward those needs and other ends.

SUMMARY OF THE INVENTION

The present invention provides a JAK inhibitor that is a compound of general formula (I), or a pharmaceutically acceptable salt, prodrug, hydrate, or solvate thereof,

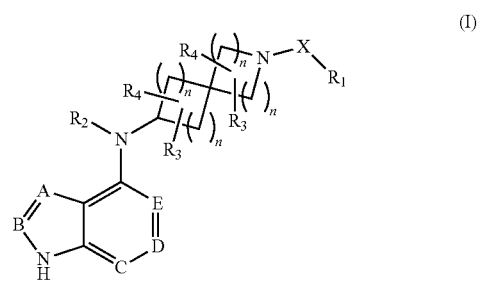

(I)

In formula (I), n is an integer of 0-5;

A, B, C, D and E are independently N or C—$R_5$, and noted that herein B does not represent boron atom and C does not represent carbon atom;

$R_5$ is selected from the group consisting of hydrogen, deuterium, halogen, hydroxy, amino, nitro, CN, —$SO_2NH_2$, —$SONH_2$, —NHOH, —$CONH_2$, —$OR_{5a}$, —$N(R_{5a})_2$, and —$SR_{5a}$; or $R_5$ is selected from the group consisting of alkyl, cycloalkyl, alkoxy, alkylthio, alkylsulfonyl, heterocyclyl, aryl, heteroaryl, —$CF_3$, —$CF_2H$, —$OCF_3$, —$OCF_2H$, $C_{1-6}$ alkyl substituted with one to five fluorines, $C_{3-6}$ cycloalkyl substituted with one to five fluorines, $C_{1-4}$ alkoxy substituted with one to five fluorines, $C_{1-4}$ alkylthio substituted with one to five fluorines, $C_{1-4}$ alkylsulfonyl substituted with one to five fluorines, carboxy, $C_{1-4}$ alkyloxycarbonyl, and $C_{1-4}$ alkylcarbonyl;

$R_{5a}$ is selected from the group consisting of alkyl, cycloalkyl, alkoxy, alkylthio, alkylsulfonyl, heterocyclyl, aryl, heteroaryl, —$CF_3$, —$CF_2H$, —$OCF_3$, —$OCF_2H$, $C_{1-6}$ alkyl substituted with one to five fluorines, $C_{3-6}$ cycloalkyl substituted with one to five fluorines, $C_{1-4}$ alkoxy substituted with one to five fluorines, $C_{1-4}$ alkylthio substituted with one to five fluorines, $C_{1-4}$ alkylsulfonyl substituted with one to five fluorines, carboxy, $C_{1-4}$ alkyloxycarbonyl, and $C_{1-4}$ alkylcarbonyl;

$R_2$, $R_3$, and $R_4$ independently at each occurrence are selected from the group consisting of hydrogen, alkyl, alkenyl, alkynyl, cycloalkyl, cycloalkenyl, cycloalkylalkyl, cycloalkylalkenyl, cycloalkylalkynyl, cycloalkenylalkyl, cycloalkenylalkenyl, cycloalkenylalkynyl, heterocyclyl, heterocyclylalkyl, heterocyclylalkenyl, heterocyclylalkynyl, aryl, arylalkyl, arylalkenyl, arylalkynyl, arylcycloalkyl, aryloxyalkyl, aryloxycycloalkyl, heteroaryl, heteroarylalkyl, heteroarylalkenyl, heteroarylalkynyl, heteroarylcycloalkyl, heteroaryloxyalkyl, and heteroaryloxycycloalkyl, any of which may be optionally substituted with one or more $R_{2a}$;

$R_{2a}$ is selected from the group consisting of halogen, cyano, hydroxy, oxo, —$NH_2$, —$SO_2NH_2$, —$SONH_2$, —$CONH_2$, alkyl, alkenyl, alkynyl, cycloalkyl, cycloalkeny, heterocyclyl, $R_{2b}$O-L-, $R_{2b}$S-L-, $(R_{2b})_2$N-L-, $R_{2b}$—C(=O) L-, $R_{2b}$—C=O)-L-, $(R_{2b})_2$N—C(=O)-L-, $R_{2b}$—C (=O)N (R_{2b})-L-, $R_{2b}$O—C(=O)N(R_{2b})-L-, $(R_{2b})_2$NC(=O)N (R_{2b})-L-, $R_{2b}$—C(=O)O-L-, $R_{2b}$O—C(=O)O-L-, $(R_{2b})_2$N—C(=O)O-L-, $R_{2b}$O—S(=O)$_2$-L-, $(R_{2b})_2$ N—S (=O)$_2$-L-, $R_{2b}$—S(=O)$_2$N($R_{2b}$)-L-, $R_{2b}$—S(=O)$_2$N($R_{2b}$)-

L-, $(R_{2b})_2$N—S(=O)$_2$N($R_{2b}$)-L-, $R_{2b}$ S(=O)$_2$O-L-, $R_{2b}$—S(=O)$_2$O-L-, $(R_{2b})$N—S(=O)$_2$O-L-, aryl-, aryloxy-, heteroaryl, and heteroaryloxy;

$R_{2b}$ independently at each occurrence is selected from the group consisting of alkyl, alkenyl, alkynyl, cycloalkyl, heterocyclyl, aryl, and heteroaryl;

$R_1$ is hydrogen, alkyl, heteroalkyl, aryl, aryloxy, heteroaryl, or heteroaryloxy, which may be optionally substituted with one or more $R_{1a}$, wherein any two $R_{1a}$ form, together with the ring atom(s) to which they are attached, a cycloalkyl or heterocycle, and two $R_{1a}$ are either attached to the same C atom or to two nonadjacent C atoms; $R_{1a}$ independently at each occurrence is selected from the group consisting of halogen, cyano, hydroxy, oxo, —NH$_2$, —SO$_2$NH$_2$, —SONH$_2$, —CONH$_2$, alkyl, alkenyl, alkynyl, alkenylalkyl, alkynylalkyl, cycloalkyl, cycloalkenyl, cycloalkylalkyl, cycloalkylalkenyl, heterocyclyl, $R_{1b}$O-L-, $R_{1b}$S-L-, $(R_{1b})_2$N-L-, $R_{1b}$—C(=O)L-, $R_{1b}$—C(=O)-L-, $(R_{1b})_2$N—C(=O)-L-, $R_{1b}$—C(=O)N($R_{1b}$)-L-, $R_{1b}$O—C(=O)N($R_{1b}$)-L-, $(R_{1b})_2$NC(=O)N($R_{1b}$)-L-, $R_{1b}$—C(=O)O-L-, $R_{1b}$O—C(=O)O-L-, $(R_{1b})_2$N—C(=O)O-L-, $R_{1b}$O—S(=O)$_2$-L-, $(R_{1b})_2$N—S(=O)$_2$-L-, $R_{1b}$—S(=O)$_2$N($R_{1b}$)-L-, $R_{1b}$—S(=O)$_2$N($R_{1b}$)-L-, $(R_{1b})_2$N—S(=O)$_2$N($R_{1b}$)-L-, $R_{1b}$ S(=O)$_2$O-L-, $R_{1b}$—S(=O)$_2$O-L-, $(R_{1b})$N—S(=O)$_2$O-L-, aryl, aryloxy, heteroaryl, and heteroaryloxy;

$R_{1b}$ independently at each occurrence is selected from the group consisting of alkyl, alkenyl, alkynyl, cycloalkyl, heterocyclyl, aryl, and heteroaryl;

L is a covalent bond or L is independently at each occurrence selected from the group consisting of alkyl, cycloalkyl, alkylcycloalkyl and cycloalkyl; and X is a covalent bond or X is —C(=O)—, —S(=O)—, —S(=O)$_2$—, —C(=O)O—, —C(=O)NH—, —S(=O)NH—, —S(=O)$_2$NH—.

In another embodiment, in formula (I), n is 1 and 2.

In another embodiment, in formula (I), $R_3$ and $R_4$ are both hydrogens.

In another embodiment, in formula (I), $R_5$ is hydrogen.

In another embodiment, in formula (I), $R_2$ is alkyl.

In another embodiment, in formula (I), X is —C(=O)—, —S(=O)—, —S(=O)$_2$—, —C(=O)O—, —C(=O)NH—, —S(=O)NH—, —S(=O)$_2$NH—.

In another embodiment, in formula (I), $R_1$ is

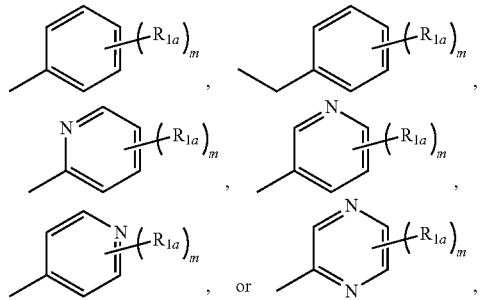

m is an integer of 1-3; and $R_{1a}$ independently at each occurrence is selected from the group consisting of halogen, cyano, hydroxy, —NH$_2$, —SO$_2$NH$_2$, —SONH$_2$, —CONH$_2$, alkyl, alkenyl, alkynyl, alkenylalkyl, alkynylalkyl, cycloalkyl, cycloalkenyl, cycloalkylalkyl, cycloalkylalkenyl, heterocyclyl, aryl, aryloxy, heteroaryl, and heteroaryloxy.

In another embodiment, in formula (I), $R_1$ is

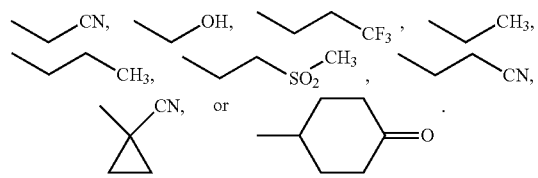

In another embodiment, in formula (I), $R_1$ is

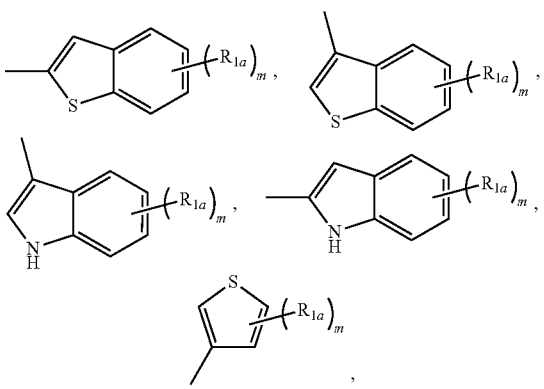

m is an integer of 1-3; and $R_{1a}$ independently at each occurrence is selected from the group consisting of halogen, cyano, hydroxy, —NH$_2$, —SO$_2$NH$_2$, —SONH$_2$, —CONH$_2$, alkyl, alkenyl, alkynyl, alkenylalkyl-, alkynylalkyl, cycloalkyl, cycloalkenyl, cycloalkylalkyl, cycloalkylalkenyl, heterocyclyl, aryl-, aryloxy-, heteroaryl, and heteroaryloxy.

In another embodiment, in formula (I), A and B are CH, C is N, D is CH, and E is N.

In another embodiment, the compound of formula (I) is selected from the group consisting of 2-fluoro-4-(6-(methyl(7H-pyrrolo[2,3-d]pyrimidin-4-yl)amino)-2-azaspiro[3.3]heptane-2-carbonyl)benzonitrile; 3-(6-(methyl(7H-pyrrolo[2,3-d]pyrimidin-4-yl)amino)-2-azaspiro[3.3]heptan-2-yl)-3-oxopropanenitrile; 2-hydroxy-1-(6-(methyl(7H-pyrrolo[2,3-d]pyrimidin-4-yl)amino)-2-azaspiro[3.3]heptan-2-yl)ethanone; 1-(6-(methyl(7H-pyrrolo[2,3-d]pyrimidin-4-yl)amino)-2-azaspiro[3.3]heptan-2-yl)ethanone; 1-(6-(methyl(7H-pyrrolo[2,3-d]pyrimidin-4-yl)amino)-2-azaspiro[3.3]heptan-2-yl)propan-1-one; N-(2-(ethylsulfonyl)-2-azaspiro[3.3]heptan-6-yl)-N-methyl-7H-pyrrolo[2,3-d]pyrimidin-4-amine; methyl 6-(methyl(7H-pyrrolo[2,3-d]pyrimidin-4-yl)amino)-2-azaspiro[3.3]heptane-2-carboxylate; ethyl 6-(methyl(7H-pyrrolo[2,3-d]pyrimidin-4-yl)amino)-2-azaspiro[3.3]heptane-2-carboxylate; (6-(methyl(7H-pyrrolo[2,3-d]pyrimidin-4-yl)amino)-2-azaspiro[3.3]heptan-2-yl)(pyridin-3-yl)methanone; 4-(6-(methyl(7H-pyrrolo[2,3-d]pyrimidin-4-yl)amino)-2-azaspiro[3.3]heptan-2-yl)-4-oxobutanenitrile; 3-(6-(methyl(7H-pyrrolo[2,3-d]pyrimidin-4-yl)amino)-2-azaspiro[3.3]heptane-2-carbonyl)

benzonitrile; 4-(6-(methyl(7H-pyrrolo[2,3-d]pyrimidin-4-yl)amino)-2-azaspiro[3.3]heptane-2-carbonyl)cyclohexanone; (6-(methyl(7H-pyrrolo[2,3-d]pyrimidin-4-yl)amino)-2-azaspiro[3.3]heptan-2-yl)(3-(trifluoromethyl)phenyl)methanone; 3-fluoro-4-(6-(methyl(7H-pyrrolo[2,3-d]pyrimidin-4-yl)amino)-2-azaspiro[3.3]heptane-2-carbonyl)benzonitrile; 4-(2-(6-(methyl(7H-pyrrolo[2,3-d]pyrimidin-4-yl)amino)-2-azaspiro[3.3]heptan-2-yl)-2-oxoethyl)benzonitrile; 1-(6-(methyl(7H-pyrrolo[2,3-d]pyrimidin-4-yl)amino)-2-azaspiro[3.3]heptan-2-yl)-3-(methylsulfonyl)propan-1-one; (6-(methyl(7H-pyrrolo[2,3-d]pyrimidin-4-yl)amino)-2-azaspiro[3.3]heptan-2-yl)(3-(trifluoromethoxy)phenyl)methanone; (6-(methyl(7H-pyrrolo[2,3-d]pyrimidin-4-yl)amino)-2-azaspiro[3.3]heptan-2-yl)(pyrazin-2-yl)methanone; 1-(6-(methyl(7H-pyrrolo[2,3-d]pyrimidin-4-yl)amino)-2-azaspiro[3.3]heptane-2-carbonyl)cyclopropanecarbonitrile; benzo[b]thiophen-2-yl(6-(methyl(7H-pyrrolo[2,3-d]pyrimidin-4-yl)amino)-2-azaspiro[3.3]heptan-2-yl)methanone; 4,4,4-trifluoro-1-(6-(methyl(7H-pyrrolo[2,3-d]pyrimidin-4-yl)amino)-2-azaspiro[3.3]heptan-2-yl)butan-1-one; benzo[b]thiophen-3-yl(6-(methyl(7H-pyrrolo[2,3-d]pyrimidin-4-yl)amino)-2-azaspiro[3.3]heptan-2-yl)methanone; 2-(1H-indol-3-yl)-1-(6-(methyl(7H-pyrrolo[2,3-d]pyrimidin-4-yl)amino)-2-azaspiro[3.3]heptan-2-yl)ethenone; (4-methoxyphenyl)(6-(methyl(7H-pyrrolo[2,3-d]pyrimidin-4-yl)amino)-2-azaspiro[3.3]heptan-2-yl)methanone; (4-chlorophenyl)(6-(methyl(7H-pyrrolo[2,3-d]pyrimidin-4-yl)amino)-2-azaspiro[3.3]heptan-2-yl)methanone; (4-ethynylphenyl)(6-(methyl(7H-pyrrolo[2,3-d]pyrimidin-4-yl)amino)-2-azaspiro[3.3]heptan-2-yl)methanone; (4-fluorophenyl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(3-methylthiophen-2-yl)methanone; (6-(methyl(7H-pyrrolo[2,3-d]pyrimidin-4-yl)amino)-2-azaspiro[3.3]heptan-2-yl)(6-methylpyrazin-2-yl)methanone; (1H-indol-2-yl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(4-(trifluoromethyl)phenyl)methanone; (5-chloropyridin-2-yl)(6-(methyl(7H-pyrrolo[2,3-d]pyrimidin-4-yl)amino)-2-azaspiro[3.3]heptan-2-yl)methanone; N-(3-chlorophenyl)-6-(methyl(7H-pyrrolo[2,3-d]pyrimidin-4-yl)amino)-2-azaspiro[3.3]heptane-2-carboxamide; 2-methyl-4-(6-(methyl(7H-pyrrolo[2,3-d]pyrimidin-4-yl)amino)-2-azaspiro[3.3]heptane-2-carbonyl)benzonitrile; 5-(6-(methyl(7H-pyrrolo[2,3-d]pyrimidin-4-yl)amino)-2-azaspiro[3.3]heptane-2-carbonyl)picolinonitrile; 2-chloro-4-(6-(methyl(7H-pyrrolo[2,3-d]pyrimidin-4-yl)amino)-2-azaspiro[3.3]heptane-2-carbonyl)benzonitrile; 3-chloro-4-(6-(methyl(7H-pyrrolo[2,3-d]pyrimidin-4-yl)amino)-2-azaspiro[3.3]heptane-2-carbonyl)benzonitrile; (4-iodophenyl)(6-(methyl(7H-pyrrolo[2,3-d]pyrimidin-4-yl)amino)-2-azaspiro[3.3]heptan-2-yl)methanone; (4-cyclopropylphenyl)(6-(methyl(7H-pyrrolo[2,3-d]pyrimidin-4-yl)amino)-2-azaspiro[3.3]heptan-2-yl)methanone; (4-ethynyl-3-methylphenyl)(6-(methyl(7H-pyrrolo[2,3-d]pyrimidin-4-yl)amino)-2-azaspiro[3.3]heptan-2-yl)methanone; (4-ethynyl-2-fluorophenyl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(4-(prop-1-yn-1-yl)phenyl)methanone; (2-chloro-4-ethynylphenyl)(6-(methyl(7H-pyrrolo[2,3-d]pyrimidin-4-yl)amino)-2-azaspiro[3.3]heptan-2-yl)methanone; 3-methyl-4-(6-(methyl(7H-pyrrolo[2,3-d]pyrimidin-4-yl)amino)-2-azaspiro[3.3]heptane-2-carbonyl)benzonitrile; (6-(methyl(7H-pyrrolo[2,3-d]pyrimidin-4-yl)amino)-2-azaspiro[3.3]heptan-2-yl)(1H-pyrazol-3-yl)methanone; (3-chloro-4-ethynylphenyl)(6-(methyl(7H-pyrrolo[2,3-d]pyrimidin-4-yl)amino)-2-azaspiro[3.3]heptan-2-yl)methanone; (4-ethynyl-3-fluorophenyl)(6-(methyl(7H-pyrrolo[2,3-d]pyrimidin-4-yl)amino)-2-azaspiro[3.3]heptan-2-yl)methanone; (5-ethynylpyridin-2-yl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(1-methyl-H-benzo[d]imidazol-5-yl)methanone; (6-(methyl(7H-pyrrolo[2,3-d]pyrimidin-4-yl)amino)-2-azaspiro[3.3]heptan-2-yl)(1-methyl-1H-pyrazol-3-yl)methanone. 2,5-difluoro-4-(6-(methyl(7H-pyrrolo[2,3-d]pyrimidin-4-yl)amino)-2-azaspiro[3.3]heptane-2-carbonyl)benzonitrile; 2,6-difluoro-4-(6-(methyl(7H-pyrrolo[2,3-d]pyrimidin-4-yl)amino)-2-azaspiro[3.3]heptane-2-carbonyl)benzonitrile; 2,3-difluoro-4-(6-(methyl(7H-pyrrolo[2,3-d]pyrimidin-4-yl)amino)-2-azaspiro[3.3]heptane-2-carbonyl)benzonitrile; 5-fluoro-2-methyl-4-(6-(methyl(7H-pyrrolo[2,3-d]pyrimidin-4-yl)amino)-2-azaspiro[3.3]heptane-2-carbonyl)benzonitrile; (2,3-difluorophenyl)(6-(methyl(7H-pyrrolo[2,3-d]pyrimidin-4-yl)amino)-2-azaspiro[3.3]heptan-2-yl)methanone; 3,5-difluoro-4-(6-(methyl(7H-pyrrolo[2,3-d]pyrimidin-4-yl)amino)-2-azaspiro[3.3]heptane-2-carbonyl)benzonitrile.2-Fluoro-5-{6-[methyl-(7H-pyrrolo[2,3-d]pyrimidin-4-yl)-amino]-2-aza-spiro[3.3]heptane-2-carbonyl}-benzonitrile; 3-Fluoro-5-{6-[methyl-(7H-pyrrolo[2,3-d]pyrimidin-4-yl)-amino]-2-aza-spiro[3.3]heptane-2-carbonyl}-benzonitrile; 2,5-Difluoro-4-{6-[methyl-(7H-pyrrolo[2,3-d]pyrimidin-4-yl)-amino]-2-aza-spiro[3.3]heptane-2-carbonyl}-benzonitrile; 2,3-Dichloro-4-{6-[methyl-(7H-pyrrolo[2,3-d]pyrimidin-4-yl)-amino]-2-aza-spiro[3.3]heptane-2-carbonyl}-benzonitrile; 2,3-Difluoro-5-{6-[methyl-(7H-pyrrolo[2,3-d]pyrimidin-4-yl)-amino]-2-aza-spiro[3.3]heptane-2-carbonyl}-benzonitrile; 3,4-Difluoro-5-{6-[methyl-(7H-pyrrolo[2,3-d]pyrimidin-4-yl)-amino]-2-aza-spiro[3.3]heptane-2-carbonyl}-benzonitrile; (4-Ethynyl-3-fluorophenyl)-{6-[-[(methyl-d$_3$)-(7H-pyrrolo[2,3-d]pyrimidin-4-yl)-amino]-2-aza-spiro[3.3]hept-2-yl}-methanone; 2-Fluoro-4-{6-[-[(methyl-d$_3$)-(7H-pyrrolo[2,3-d]pyrimidin-4-yl)-amino]-2-aza-spiro[3.3]heptane-2-carbonyl}-benzonitrile; (3-Fluoro-4-prop-1-ynyl-phenyl)-{6-[-[(methyl-d$_3$)-(7H-pyrrolo[2,3-d]pyrimidin-4-yl)-amino]-2-aza-spiro[3.3]hept-2-yl}-methanone; 2,3-Difluoro-4-{6-[(methyl-d$_3$)-(7H-pyrrolo[2,3-d]pyrimidin-4-yl)-amino]-2-aza-spiro[3.3]heptane-2-carbonyl}-benzonitrile; [4-(1-Methyl-1H-pyrazol-3-yl)-phenyl]-{6-[methyl-(7H-pyrrolo[2,3-d]pyrimidin-4-yl)-amino]-2-aza-spiro[3.3]hept-2-yl}-methanone; (1-Cyclopropyl-1H-pyrazol-4-yl)-{6-[methyl-(7H-pyrrolo[2,3-d]pyrimidin-4-yl)-amino]-2-aza-spiro[3.3]hept-2-yl}-methanone; 2,6-Difluoro-3-{6-[methyl-(7H-pyrrolo[2,3-d]pyrimidin-4-yl)-amino]-2-aza-spiro[3.3]heptane-2-carbonyl}-benzonitrile; N-(3-methoxy-1,2,4-thiadiazol-5-yl)-6-(methyl(7H-pyrrolo[2,3-d]pyrimidin-4-yl)amino)-2-azaspiro[3.3]heptane-2-carboxamide; 4-(6-(methyl(7H-pyrrolo[2,3-d]pyrimidin-4-yl)amino)-2-azaspiro[3.3]heptane-2-carbonyl)benzenesulfonamide; 1-{9-[Methyl-(7H-pyrrolo[2,3-d]pyrimidin-4-yl)-amino]-3-aza-spiro[5.5]undec-3-yl}-ethanone; (3-Ethanesulfonyl-3-aza-spiro[5.5]undec-9-yl)-methyl-(7H-pyrrolo[2,3-d]pyrimidin-4-yl)-amine; 2-Hydroxy-1-{9-[methyl-(7H-pyrrolo[2,3-d]pyrimidin-4-yl)-amino]-3-aza-spiro[5.5]undec-3-yl}-ethanone; 1-{9-[Methyl-(7H-pyrrolo[2,3-d]pyrimidin-4-yl)-amino]-3-aza-spiro[5.5]undec-3-yl}-propan-1-one;

Methyl-(7H-pyrrolo[2,3-d]pyrimidin-4-yl)-[3-(2,2,2-trifluoro-ethyl)-3-aza-spiro[5.5]undec-9-yl]-amine; {9-[Methyl-(7H-pyrrolo[2,3-d]pyrimidin-4-yl)-amino]-3-aza-spiro[5.5]undec-3-yl}-pyridin-3-yl-methanone; 4-{9-[Methyl-(7H-pyrrolo[2,3-d]pyrimidin-4-yl)-amino]-3-aza-spiro[5.5]undec-3-yl}-4-oxo-butyronitrile; 4-{9-[Methyl-(7H-pyrrolo[2,3-d]pyrimidin-4-yl)-amino]-3-aza-spiro[5.5]undecane-3-carbonyl}-cyclohexanone; {9-[Methyl-(7H-pyrrolo[2,3-d]pyrimidin-4-yl)-amino]-3-aza-spiro[5.5]undec-3-yl}-(3-trifluoromethyl-phenyl)-methanone; 3-Fluoro-4-{9-[methyl-(7H-pyrrolo[2,3-d]pyrimidin-4-yl)-amino]-3-aza-spiro[5.5]undecane-3-carbonyl}-benzonitrile; 4-(2-{9-[Methyl-(7H-pyrrolo[2,3-d]pyrimidin-4-yl)-amino]-3-aza-spiro[5.5]undec-3-yl}-2-oxo-ethyl)-benzonitrile; 3-Methanesulfonyl-1-{9-[methyl-(7H-pyrrolo[2,3-d]pyrimidin-4-yl)-amino]-3-aza-spiro[5.5]undec-3-yl}-propan-1-one; 2-Fluoro-4-{9-[methyl-(7H-pyrrolo[2,3-d]pyrimidin-4-yl)-amino]-3-aza-spiro[5.5]undecane-3-carbonyl}-benzonitrile; {9-[Methyl-(7H-pyrrolo[2,3-d]pyrimidin-4-yl)-amino]-3-aza-spiro[5.5]undec-3-yl}-pyrazin-2-yl-methanone; 1-{9-[Methyl-(7H-pyrrolo[2,3-d]pyrimidin-4-yl)-amino]-3-aza-spiro[5.5]undecane-3-carbonyl}-cyclopropanecarbonitrile; (6-Methyl-pyrazin-2-yl)-{9-[methyl-(7H-pyrrolo[2,3-d]pyrimidin-4-yl)-amino]-3-aza-spiro[5.5]undec-3-yl}-methanone; 4,4,4-Trifluoro-1-{9-[methyl-(7H-pyrrolo[2,3-d]pyrimidin-4-yl)-amino]-3-aza-spiro[5.5]undec-3-yl}-butan-1-one; Benzo[b]thiophen-3-yl-{9-[methyl-(7H-pyrrolo[2,3-d]pyrimidin-4-yl)-amino]-3-aza-spiro[5.5]undec-3-yl}-methanone; 2-(1H-Indol-3-yl)-1-{9-[methyl-(7H-pyrrolo[2,3-d]pyrimidin-4-yl)-amino]-3-aza-spiro[5.5]undec-3-yl}-ethanone; {9-[Methyl-(7H-pyrrolo[2,3-d]pyrimidin-4-yl)-amino]-3-aza-spiro[5.5]undec-3-yl}-(3-methyl-thiophen-2-yl)-methanone; (1H-Indol-2-yl)-{9-[methyl-(7H-pyrrolo[2,3-d]pyrimidin-4-yl)-amino]-3-aza-spiro[5.5]undec-3-yl}-methanone; (6,7-Dihydro-5H-pyrrolo[2,3-d]pyrimidin-4-yl)-methyl-[3-(propane-1-sulfonyl)-3-aza-spiro[5.5]undec-9-yl]-amine; 2-Methylamino-1-{9-[methyl-(7H-pyrrolo[2,3-d]pyrimidin-4-yl)-amino]-3-aza-spiro[5.5]undec-3-yl}-ethanone; 9-[(6,7-Dihydro-5H-pyrrolo[2,3-d]pyrimidin-4-yl)-methyl-amino]-3-aza-spiro[5.5]undecane-3-carboxylic acid isopropyl ester; Cyclopropyl-{9-[methyl-(7H-pyrrolo[2,3-d]pyrimidin-4-yl)-amino]-3-aza-spiro[5.5]undec-3-yl}-methanone 1-{9-[Methyl-(7H-pyrrolo[2,3-d]pyrimidin-4-yl)-amino]-3-aza-spiro[5.5]undec-3-yl}-butan-1-one; {9-[Methyl-(7H-pyrrolo[2,3-d]pyrimidin-4-yl)-amino]-3-aza-spiro[5.5]undec-3-yl}-(3-trifluoromethoxy-phenyl)-methanone; 3-{9-[Methyl-(7H-pyrrolo[2,3-d]pyrimidin-4-yl)-amino]-3-aza-spiro[5.5]undecane-3-carbonyl}-benzonitrile; 9-[Methyl-(7H-pyrrolo[2,3-d]pyrimidin-4-yl)-amino]-3-aza-spiro[5.5]undecane-3-carboxylic acid ethyl ester; Methyl-(7H-pyrrolo[2,3-d]pyrimidin-4-yl)-[3-(2,2,2-trifluoro-ethanesulfonyl)-3-aza-spiro[5.5]undec-9-yl]-amine; 3-{9-[Methyl-(7H-pyrrolo[2,3-d]pyrimidin-4-yl)-amino]-3-aza-spiro[5.5]undec-3-yl}-3-oxo-propionitrile; Benzo[b]thiophen-2-yl-{9-[methyl-(7H-pyrrolo[2,3-d]pyrimidin-4-yl)-amino]-3-aza-spiro[5.5]undec-3-yl}-methanone; tert-butyl 9-(methyl(7H-pyrrolo[2,3-d]pyrimidin-4-yl)amino)-3-azaspiro[5.5]undecane-3-carboxylate; 2-methoxy-1-(9-(methyl(7H-pyrrolo[2,3-d]pyrimidin-4-yl)amino)-3-azaspiro[5.5]undecan-3-yl)ethan-1-one; 1-(9-(methyl(7H-pyrrolo[2,3-d]pyrimidin-4-yl)amino)-3-azaspiro[5.5]undecan-3-yl)-2-phenoxyethan-1-one; 2,2,2-trifluoroethyl 9-(methyl(7H-pyrrolo[2,3-d]pyrimidin-4-yl)amino)-3-azaspiro[5.5]undecane-3-carboxylate; N-(3-methoxy-1,2,4-thiadiazol-5-yl)-9-(methyl(7H-pyrrolo[2,3-d]pyrimidin-4-yl)amino)-3-azaspiro[5.5]undecane-3-carboxamide; 9-(methyl(7H-pyrrolo[2,3-d]pyrimidin-4-yl)amino)-N-(2,2,2-trifluoroethyl)-3-azaspiro[5.5]undecane-3-carboxamide; N-methyl-9-(methyl(7H-pyrrolo[2,3-d]pyrimidin-4-yl)amino)-3-azaspiro[5.5]undecane-3-carboxamide; N,N-diethyl-9-(methyl(7H-pyrrolo[2,3-d]pyrimidin-4-yl)amino)-3-azaspiro[5.5]undecane-3-sulfonamide; 4-(9-(methyl(7H-pyrrolo[2,3-d]pyrimidin-4-yl)amino)-3-azaspiro[5.5]undecane-3-carbonyl)benzenesulfonamide; 3-(9-(methyl(7H-pyrrolo[2,3-d]pyrimidin-4-yl)amino)-3-azaspiro[5.5]undecan-3-yl)-3-oxopropane-1-sulfonamide; 3-fluoro-5-(2-(9-(methyl(7H-pyrrolo[2,3-d]pyrimidin-4-yl)amino)-3-azaspiro[5.5]undecan-3-yl)-2-oxoethoxy)benzonitrile; 4-(2-(9-(methyl(7H-pyrrolo[2,3-d]pyrimidin-4-yl)amino)-3-azaspiro[5.5]undecan-3-yl)-2-oxoethoxy)benzonitrile; 3-(2-(9-(methyl(7H-pyrrolo[2,3-d]pyrimidin-4-yl)amino)-3-azaspiro[5.5]undecan-3-yl)-2-oxoethoxy)benzonitrile; 2-fluoro-4-(2-(9-(methyl(7H-pyrrolo[2,3-d]pyrimidin-4-yl)amino)-3-azaspiro[5.5]undecan-3-yl)-2-oxoethoxy)benzonitrile; 2,3-difluoro-4-(2-(9-(methyl(7H-pyrrolo[2,3-d]pyrimidin-4-yl)amino)-3-azaspiro[5.5]undecan-3-yl)-2-oxoethoxy)benzonitrile; N-(4-methoxyphenyl)-9-(methyl(7H-pyrrolo[2,3-d]pyrimidin-4-yl)amino)-3-azaspiro[5.5]undecane-3-carboxamide; N-(3-methoxyphenyl)-9-(methyl(7H-pyrrolo[2,3-d]pyrimidin-4-yl)amino)-3-azaspiro[5.5]undecane-3-carboxamide; N-(4-cyanophenyl)-9-(methyl(7H-pyrrolo[2,3-d]pyrimidin-4-yl)amino)-3-azaspiro[5.5]undecane-3-carboxamide; N-(3-cyanophenyl)-9-(methyl(7H-pyrrolo[2,3-d]pyrimidin-4-yl)amino)-3-azaspiro[5.5]undecane-3-carboxamide; N-(6-cyanopyridin-2-yl)-9-(methyl(7H-pyrrolo[2,3-d]pyrimidin-4-yl)amino)-3-azaspiro[5.5]undecane-3-carboxamide; N-(6-methoxypyridin-2-yl)-9-(methyl(7H-pyrrolo[2,3-d]pyrimidin-4-yl)amino)-3-azaspiro[5.5]undecane-3-carboxamide; N-(5-cyanopyridin-2-yl)-9-(methyl(7H-pyrrolo[2,3-d]pyrimidin-4-yl)amino)-3-azaspiro[5.5]undecane-3-carboxamide; 9-(methyl(7H-pyrrolo[2,3-d]pyrimidin-4-yl)amino)-N-(5-methylthiazol-2-yl)-3-azaspiro[5.5]undecane-3-carboxamide; 9-(methyl(7H-pyrrolo[2,3-d]pyrimidin-4-yl)amino)-N-(1-methyl-1H-pyrazol-3-yl)-3-azaspiro[5.5]undecane-3-carboxamide; 9-(methyl(7H-pyrrolo[2,3-d]pyrimidin-4-yl)amino)-N-(5-methylpyrazin-2-yl)-3-azaspiro[5.5]undecane-3-carboxamide; N-(5-methoxypyrazin-2-yl)-9-(methyl(7H-pyrrolo[2,3-d]pyrimidin-4-yl)amino)-3-azaspiro[5.5]undecane-3-carboxamide; N-(5-methoxypyridin-2-yl)-9-(methyl(7H-pyrrolo[2,3-d]pyrimidin-4-yl)amino)-3-azaspiro[5.5]undecane-3-carboxamide; N-(5-fluorothiazol-2-yl)-9-(methyl(7H-pyrrolo[2,3-d]pyrimidin-4-yl)amino)-3-azaspiro[5.5]undecane-3-carboxamide; N-(5-chlorothiazol-2-yl)-9-(methyl(7H-pyrrolo[2,3-d]pyrimidin-4-yl)amino)-3-azaspiro[5.5]undecane-3-carboxamide; N-(5-cyanothiazol-2-yl)-9-(methyl(7H-pyrrolo[2,3-d]pyrimidin-4-yl)amino)-3-azaspiro[5.5]undecane-3-carboxamide; 9-(methyl(7H-pyrrolo[2,3-d]pyrimidin-4-yl)amino)-N-(thiazol-2-yl)-3-azaspiro[5.5]undecane-3-carboxamide; and N-(5-methoxythiazolo[5,4-b]pyridin-2-yl)-9-(methyl(7H-pyrrolo[2,3-d]pyrimidin-4-yl)amino)-3-azaspiro[5.5]undecane-3-carboxamide.

In another embodiment, the present invention provides a pharmaceutical composition including a therapeutically effective amount of the compound of formula (I) and a pharmaceutically acceptable excipient.

In another embodiment, the present invention provides a method for treating an autoimmune disease, cancers, tumors, inflammatory diseases, or immunologically mediated diseases. The method includes administering to a subject in need thereof a composition containing a therapeutically effective amount of the compound of formula (I) and other therapeutic agents.

In another embodiment, the method is administered in combination with a therapeutic agent selected from the group consisting of anticancer drugs, steroid drugs, methotrexates, leflunomides, anti-TNFa agents, calcineurin inhibitors, antihistaminic drugs, and a mixture thereof.

DETAILED DESCRIPTION OF THE INVENTION

The methods described herein include administering to a subject in need a composition containing a therapeutically effective amount of one or more JAK inhibitor compounds described herein.

Prodrugs mean any compound which releases an active parent drug according to the compound Formula (I) in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds.

Tautomers mean compounds produced by the phenomenon wherein a proton of one atom of a molecule shifts to another atom. Tautomers also refer to one of two or more structural isomers that exist in equilibrium and are readily converted from one isomeric form to another. One of ordinary skill in the art would recognize that other tautomeric ring atom arrangements are possible. All such isomeric forms of these compounds are expressly included in the present disclosure.

Isomers mean compounds having identical molecular formulae but differ in the nature or sequence of bonding of their atoms or in the arrangement of their atoms in space. Isomers that differ in the arrangement of their atoms in space are termed stereoisomers. Stereoisomers that are not mirror images of one another are termed diastereomers, and those that are no superimposable mirror images of each other are termed enantiomers. When a compound has an asymmetric center, for example, it is bonded to four different groups, a pair of enantiomers is possible. A chiral compound can exist as either individual enantiomer or as a mixture thereof. Unless otherwise indicated, the description is intended to include individual stereoisomers as well as mixtures.

Certain compounds of the present disclosure can exist in unsolvated forms as well as solvated forms, including hydrated forms. Solvates refer to a complex formed by combination of solvent molecules with the compound of formula I. The solvent can be an organic compound, an inorganic compound, or a mixture thereof.

Pharmaceutically acceptable salts represent those salts, which are, within the scope of medical judgment, suitable for use in contact for the tissues of humans and lower animals without undue toxicity, irritation, allergic response and the like, and are commensurate with a reasonable benefit/risk ratio. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

Therapeutically effective amount means an amount of compound or a composition of the present invention effective in inhibiting Janus kinase and thus producing the desired therapeutic effect.

As used herein, the term alkyl refers to a monovalent straight or branched chain, saturated aliphatic hydrocarbon radical having a number of carbon atoms in the specified range. For example, alkyl refers to any of the hexyl alkyl and pentyl alkyl isomers as well as n-, iso-, sec- and t-butyl, n- and iso-propyl, ethyl and methyl. Alkyl also includes saturated aliphatic hydrocarbon radicals wherein one or more hydrogens are replaced with deuterium, for example, $CD_3$.

The term branched alkyl refers to an alkyl group as defined above except that straight chain alkyl groups in the specified range are excluded. As defined herein, branched alkyl includes alkyl groups in which the alkyl is attached to the rest of the compound via a secondary or tertiary carbon. For example, isopropyl is a branched alkyl group.

The term cycloalkyl refers to any monocyclic ring of an alkane having a number of carbon atoms in the specified range. For example, cycloalkyl refers to cyclopropyl, cyclobutyl, cyclopentyl, and cyclohexyl.

The term halogen refers to fluorine, chlorine, bromine and iodine (alternatively referred to as fluoro, chloro, bromo, and iodo).

The term haloalkyl refers to an alkyl group as defined above in which one or more of the hydrogen atoms have been replaced with a halogen (i.e., F, Cl, Br and/or I). For example, haloalkyl refers to a linear or branched alkyl group as defined above with one or more halogen substituents. The term fluoroalkyl has an analogous meaning except that the halogen substituents are restricted to fluoro. Suitable fluoroalkyls include the series $(CH_2)_{0-4}CF_3$.

The term C(O) or CO refers to carbonyl. The terms $S(O)_2$ or $SO_2$ refers to sulfonyl.

The term S(O) or SO refers to sulfinyl.

The term aryl refers to phenyl, naphthyl, tetrahydronaphthyl, idenyl, dihydroindenyl and the like. An aryl of particular interest is phenyl.

The term heteroaryl refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl.

Heteroaryls of particular interest are pyrrolyl, imidazolyl, pyridyl, pyrazinyl, quinolinyl (or quinolyl), isoquinolinyl (or isoquinolyl), and quinoxalinyl. Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings, which can be used in the present invention. These rings are merely representative. Synthetic methods for preparing the compounds of the present invention are illustrated in the following Schemes, Methods, and Examples. Starting materials are commercially available or may be prepared according to procedures known in the art or as described herein.

The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily appreciate that known variations in the conditions and processes can be used to prepare such compounds.

The present invention provides The JAK inhibitor compounds having general formula (I).

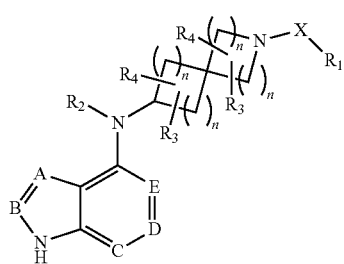

(I)

The JAK inhibitor compounds of formula (I) can be prepared by methods well known in the art of organic chemistry. The starting material used for the synthesis of these compounds can be either synthesized or obtained from commercial sources, such as, but not limited to, Chinese chemical companies or Sigma-Aldrich Chemical Co. (St. Louis, Mo.) at China. The compounds described herein, and other related compounds having different substituents are optionally synthesized using techniques and materials, such as described, for example, in March, ADVANCED ORGANIC CHEMISTRY 4th Ed., (Wiley 1992); Carey and Sundberg, ADVANCED ORGANIC CHEMISTRY 4th Ed., Vols. A and B (Plenum 2000, 2001); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (JohnWiley and Sons, 1991); and Larock's Comprehensive Organic Transformations (VCH Publishers Inc., 1989). Other methods for the synthesis of compounds described herein may be found in International Patent Application Publication No. WO 2011/003418 A1, Dymock al. *Future Medicinal Chemistry* (2014)6(12), 1439-1471. The definitions of chemistry terms used in this application may be found in these reference (if not otherwise defined herein). As a guide the following synthetic methods may be utilized.

During the synthetic sequences it may be necessary and/or desirable to protect sensitive or reactive groups on any of the molecules concerned. This is achieved by means of conventional protecting groups, such as those described in T. W Greene and P. G. M. Wutts "Protective groups in Organic Synthesis" 3rd Edition, John Wiley and Sons, 1999. The protective groups are optionally removed at a convenient subsequent stage using methods well known in the art. The products of the reactions are optionally isolated and purified. If desired, using conventional techniques, but not limited to, filtration, distillation crystallization, chromatography and the like. Such materials are optionally characterized using conventional means, including physical constant and spectra data.

Compounds described herein may possess one or more sterocenters and each center may exist in the R or S configuration. The compounds presented herein include all diasterometic, enantiomeric, and epimeric forms as well as the appropriate mixtures thereof.

The JAK inhibitor compounds of formula (I) can be, for example, 6-(1λ-azanyl)-2-azaspiro[3.3]heptane derivatives can be prepared by the general synthetic route shown in Scheme I.

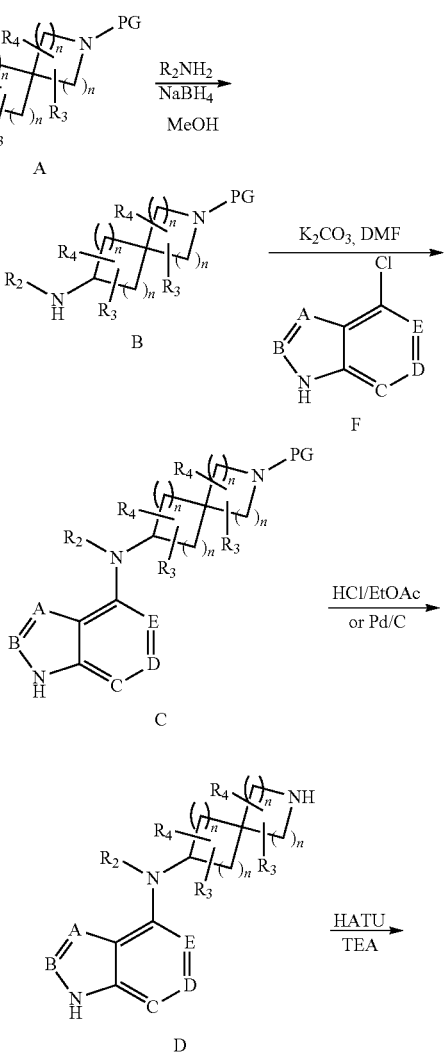

Scheme I

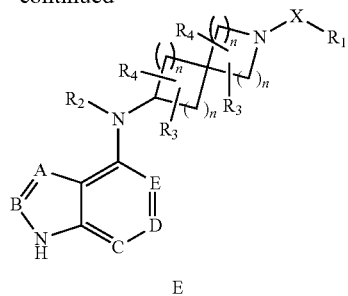

E

Referring to Scheme I, different commercially available or are prepared from commercially available molecules by synthetic transformations ketone (A), in which PG is a protecting functional group (e.g. BOC, Benzyl etc, could be added to a range of substituted amine through reductive amination to convert a carbonyl group to an amine via an intermediate imine which can be reduced with a suitable reducing agent (e.g., sodium borohydride), a followed by replacement of Cl of the substituted pyrrolo-pyrimidine F to give a product C with $K_2CO_3$ in DMF or other solvent, then (a) deprotection reaction under acidic conditions for Boc protecting group and (b) deprotection reactions based on hydrogenolysis for benzyl type protecting group to give intermediate D.

Introduction of X—$R_1$ in compounds of general formula D can for example be achieved by reacting compounds of general formula E with suitable derivatives of X—$R_1$, isocyanated derivatives of $R_1$, isothiocyanate derivatives of $R_1$, sulfonylhalide or ester derivatives of $R_1$, sulfinylhalide or ester derivatives of $R_1$, carboxylic acid derivatives of $R_1$ under suitable coupling conditions, and amine derivatives of $R_1$ with a suitable carbonylating agent.

It is to be understood that both the foregoing general description and the following detailed description are exemplary and explanatory and are intended to provide further explanation of the invention as claimed.

General experimental conditions: Preparative thin layer chromatography (PTLC) was performed on 20×20 cm plates (500 micron thick silica gel). Silica gel chromatography was performed on a Biotage Horizon flash chromatography system. 1H NMR spectra were recorded on a Bruker Ascend TM 400 spectrometer at 400 MHz at 298° K, and the chemical shifts are given in parts per million (ppm) referenced to the residual proton signal of the deuterated solvents: $CDCl_3$ at δ=7.26 ppm and $CH_3OH$ or $CH_3OD$ at δ=3.30 ppm. LCMS spectra were taken on an Agilent Technologies 1260 Infinity or 6120 Quadrupole spectrometer.

Mass spectra (MS) were measured by electrospray ion-mass spectroscopy (ESI). All temperatures are in degrees Celsius unless otherwise noted.

Analytical HPLC mass spectrometry conditions: LC1: Column: SB-C18 50 mm×4.6 mm×2.7 μm/poroshell 120 EC-C18 3.0×50 mm 2.7-micron; Detector: DAD; Detection Wavelength: 214 nm 254 nm 280 nm; Solvents: A: MEOH B: 0.1% FA in H2O; Run Time: 8 minutes; Drying Gas Flow 12.0l/min; Nebulizer Pressure 35 psig; Drying Gas Temperature 250.

| Gradient: | | | | |
|---|---|---|---|---|
| Time | A (%) | B(%) | Flow (ml/min) | Max Pressure |
| 0 | 90 | 10 | 0.5 | 400 |
| 1 | 90 | 10 | 0.5 | 400 |
| 2.5 | 5 | 95 | 0.5 | 400 |
| 4.5 | 5 | 95 | 0.5 | 400 |
| 5 | 90 | 10 | 0.5 | 400 |
| 8 | 90 | 10 | 0.5 | 400 |

LIST OF ABBREVIATIONS

AcOH=acetic acid; Alk=alkyl; Ar=aryl; Boc=tert-butyloxycarbonyl; bs=broad singlet; $CH_2Cl_2$=dichloromethane; d=doublet; dd=doublet of doublets; DBU=1,8-diazabicyclo[5.4.0]undec-7-ene; DCM=dichloromethane; DEAD=diethyl azodicarboxylate; DMF=N,N-dimethylformamide; DMSO=dimethyl sulfoxide; EA=ethyl acetate; ESI=electrospray ionization; Et=ethyl; EtOAc=ethyl acetate; EtOH=ethyl alcohol; h=hours; HOAc=acetic acid; LiOH=lithium hydroxide; m=multiplet; Me=methyl; MeCN=acetonitrile; MeOH=methyl alcohol; MgSO4=magnesium sulfate; min=minutes; MS=30 mass spectroscopy; NaCl=sodium chloride; NaOH=sodium hydroxide; Na2SO4=sodium sulfate; NMR=nuclear magnetic resonance spectroscopy; PE=petroleum ether; PG=protecting group; Ph=phenyl; rt=room temperature; s=singlet; t=triplet; TFA=trifluoroacetic acid; THF=tetrahydrofuran; Ts=p-toluenesulfonyl (tosyl).

The compounds of the present invention can be prepared following general methods detailed below. In certain embodiments, provided herein are methods of making the Janus kinase inhibitor compounds described herein. In certain embodiments, compounds described herein are synthesized using the following synthetic schemes. In other embodiments, compounds are synthesized using methodologies analogous to those described below by the use of appropriate alterative starting materials. All key intermediates were prepared according to the following methods.

Example 1: 2-fluoro-4-(6-(methyl(7H-pyrrolo[2,3-d]pyrimidin-4-yl)amino)-2-azaspiro[3.3]heptane-2-carbonyl)benzonitrile

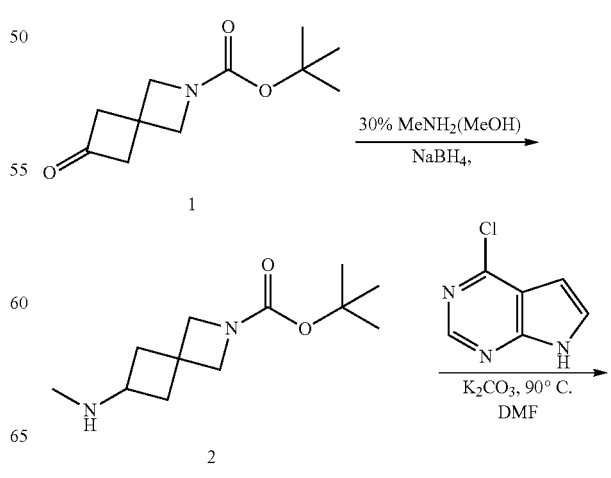

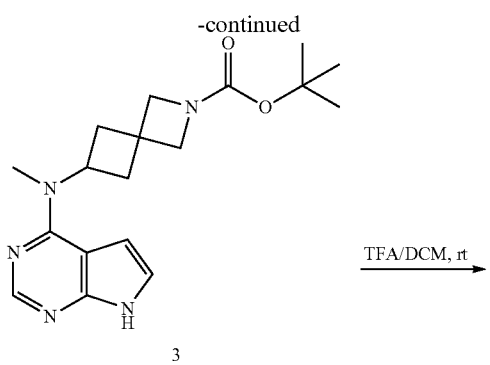

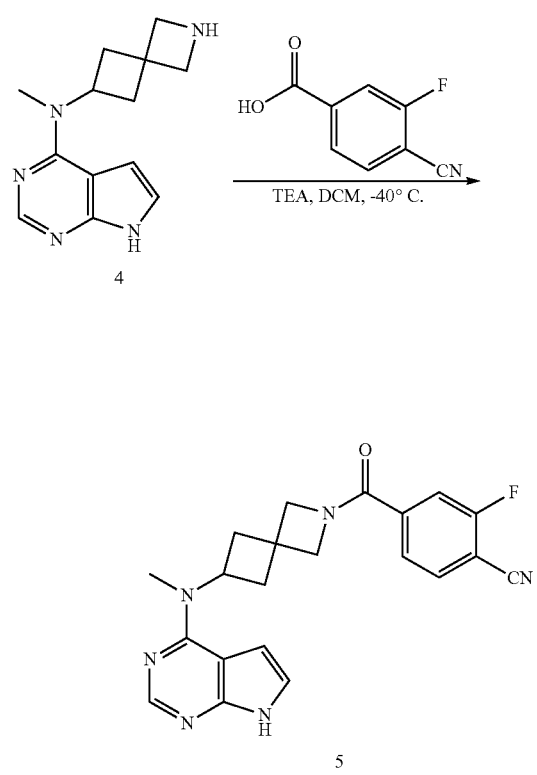

bined organic phases were washed with saturates brine, the organic layers was concentrated under reduced pressure, the residue was purified by column chromatography to give 2 (9.5 g, yield: 88%) as an colourless oil. MS: m/z [M+H]+ 227.3.

Step B. tert-butyl 6-(methyl(7H-pyrrolo[2,3-d]pyrimidin-4-yl)amino)-2-azaspiro[3.3]heptane-2-carboxylate (3)

A mixture of 2 (9.5 g, 0.042 mol), $K_2CO_3$ (11.6 g, 0.084 mol) and 4-chloro-7H-pyrrolo[2,3-d]pyrimidine (6.4 g, 0.042 mol) in DMF (100 mL) was heated to 90° C. for 15 hrs. At that moment, TLC monitored the reaction showed that the reaction mixture was gone to completely. Then the reaction mixture was poured into water (200 mL), extracted with ethyl acetate (3×100 mL), the combined organic phases were washed with saturates brine, the organic layers was concentrated under reduced pressure, the residue was purified by column chromatography to give 3 (9.8 g, yield: 68%) as a yellow solid. MS: m/z [M+H]+ 344.3.

Step C: N-methyl-N-(2-azaspiro[3.3]heptan-6-yl)-7H-pyrrolo[2,3-d]pyrimidin-4-amine (4)

To a suspension of 3 (9.8 g, 0.029 mol) in MeOH (50 mL) was added hydrochloride in EtOAc (4M, 50 mL) dropwise with stirring for 15 hrs. At that moment, the reaction mixture was concentrated, residue was dissolved in EtOH and water, then it was adjust to pH=8 with saturated sodium carbonate aqueous, then it was concentrated under reduced pressure, the residue was purified by column chromatography (DCM: MeOH=20:1 to 2:1) to give 4 (4.0 g, yield: 57%) as a yellow solid. 1H NMR (600 MHz, DMSO) δ 11.69 (s, 1H), 8.10 (s, 1H), 7.15 (s, 1H), 6.61 (s, 1H), 5.12 (m, 1H), 4.08 (s, 2H), 3.92 (s, 2H), 3.21 (s, 3H), 2.48 (d, J=11.4 Hz, 4H). MS: m/z [M+H]+ 244.3.

Step D: 2-fluoro-4-(6-(methyl(7H-pyrrolo[2,3-d]pyrimidin-4-yl)amino)-2-azaspiro[3.3]heptane-2-carbonyl)benzonitrile (5)

To a solution of 4 (2 g, 8 mmol), 4-cyano-3-fluorobenzoic acid (1.32 g, 8 mmol) and TEA (1.7 g, 16 mmol) in DCM (200 mL) was added HATU (3.65 g, 9.6 mmol) in small portions at 25° C. with stirring 16 hours. At which time TLC monitored that the reaction had completed. Then it was washed with water (100 mL), the organic layer was concentrated under reduced pressure, the residue was purified by column chromatography (DCM:MeOH=50:1) to give target compound 5 (800 mg, yield 25%) as white solid. 1H NMR (600 MHz, DMSO) δ 11.67 (s, 1H), 8.08 (m, 2H), 7.74 (t, J=8.6 Hz, 1H), 7.64 (dd, J=12.1, 8.5 Hz, 1H), 7.15 (m, 1H), 6.60 (d, J=7.7 Hz, 1H), 5.14 (ddt, J=53.9, 16.9, 8.4 Hz, 1H), 4.49 (s, 1H), 4.32 (s, 1H), 4.23 (s, 1H), 4.08 (s, 1H), 3.22 (d, J=8.9 Hz, 3H), 2.47 (s, 5H). MS m/z [M+1]+ 391.1.

The following additional Examples 2-71 shown in the Table below were prepared the following procedures outlined in the general methods above and detailed in Example 1.

Step A: tert-butyl 6-(methylamino)-2-azaspiro[3.3]heptane-2-carboxylate (2)

To a solution of 1 (10 g, 0.048 mol) in MeOH (100 mL) was added methylamine alcohol solution (9.8 g, 0.095 mol) at 25° C. The reaction mixture was stirred at the same temperature for 15 hrs, then NaBH4 (3.6 g, 0.095 mol) was added in small portions, the mixture was stirred at 25° C. for 2 hours, at that moment TLC monitored the reaction showed that it had gone to completely. So it was poured into ammonium chloride aqueous (100 mL), then it was concentrated, then extracted with EtOAc (3×100 mL), the com-

| Entry | Structure | MS (cald) [M + H]+/ MS (found) | Name |
|---|---|---|---|
| 2 | 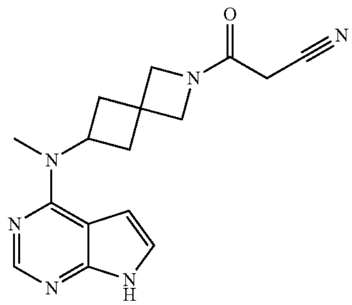 [SMILES: CN(c1ncnc2[nH]ccc12)C1CC2(C1)CN(C(=O)CC#N)C2] | 310.3/311.1 | 3-(6-(methyl(7H-pyrrolo[2,3-d]pyrimidin-4-yl)amino)-2-azaspiro[3.3]heptan-2-yl)-3-oxopropanenitrile |
| 3 | 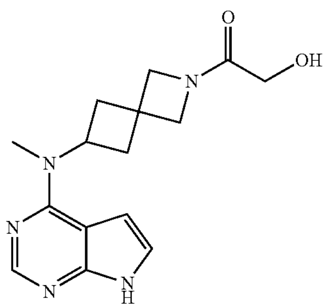 [SMILES: CN(c1ncnc2[nH]ccc12)C1CC2(C1)CN(C(=O)CO)C2] | 301.1/302.1 | 2-hydroxy-1-(6-(methyl(7H-pyrrolo[2,3-d]pyrimidin-4-yl)amino)-2-azaspiro[3.3]heptan-2-yl)ethanone |
| 4 | 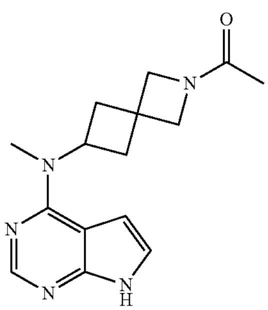 [SMILES: CC(=O)N1CC2(CC(N(C)c3ncnc4[nH]ccc34)C2)C1] | 285.1/286.1 | 1-(6-(methyl(7H-pyrrolo[2,3-d]pyrimidin-4-yl)amino)-2-azaspiro[3.3]heptan-2-yl)ethanone |
| 5 | 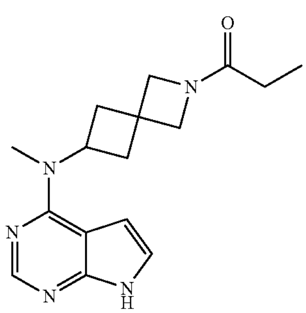 [SMILES: CCC(=O)N1CC2(CC(N(C)c3ncnc4[nH]ccc34)C2)C1] | 299.1/300.1 | 1-(6-(methyl(7H-pyrrolo[2,3-d]pyrimidin-4-yl)amino)-2-azaspiro[3.3]heptan-2-yl)propan-1-one |
| 6 | 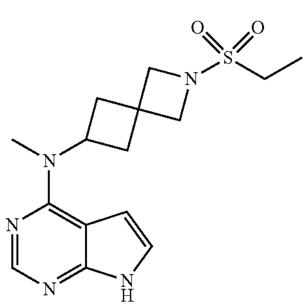 [SMILES: CCS(=O)(=O)N1CC2(CC(N(C)c3ncnc4[nH]ccc34)C2)C1] | 335.1/336.1 | N-(2-(ethylsulfonyl)-2-azaspiro[3.3]heptan-6-yl)-N-methyl-7H-pyrrolo[2,3-d]pyrimidin-4-amine |

-continued

| Entry | Structure | MS (cald) [M + H]+/ MS (found) | Name |
|---|---|---|---|
| 7 | 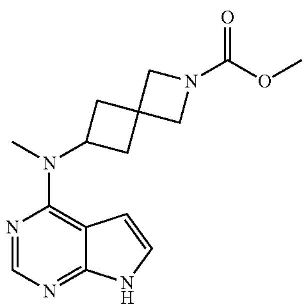 [SMILES: COC(=O)N1CC2(CC(N(C)c3ncnc4[nH]ccc34)C2)C1] | 301.1/302.1 | methyl 6-(methyl(7H-pyrrolo[2,3-d]pyrimidin-4-yl)amino)-2-azaspiro[3.3]heptan-2-carboxylate |
| 8 | 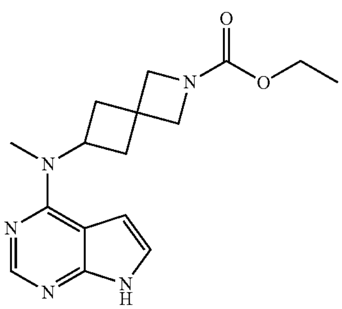 [SMILES: CCOC(=O)N1CC2(CC(N(C)c3ncnc4[nH]ccc34)C2)C1] | 315.1/316.1 | ethyl 6-(methyl(7H-pyrrolo[2,3-d]pyrimidin-4-yl)amino)-2-azaspiro[3.3]heptane-2-carboxylate |
| 9 | 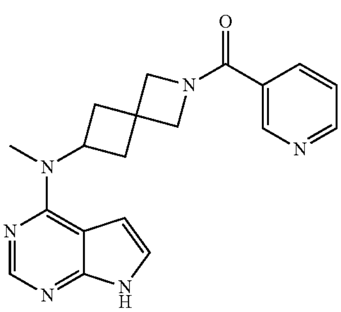 [SMILES: CN(c1ncnc2[nH]ccc12)C1CC2(C1)CN(C(=O)c1cccnc1)C2] | 348.1/349.1 | (6-(methyl(7H-pyrrolo[2,3-d]pyrimidin-4-yl)amino)-2-azaspiro[3.3]heptan-2-yl)(pyridin-3-yl)methanone |
| 10 | 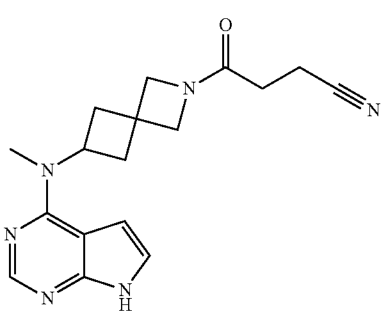 [SMILES: CN(c1ncnc2[nH]ccc12)C1CC2(C1)CN(C(=O)CCC#N)C2] | 324.1/325.1 | 4-(6-(methyl(7H-pyrrolo[2,3-d]pyrimidin-4-yl)amino)-2-azaspiro[3.3]heptan-2-yl)-4-oxobutanenitrile |
| 11 | 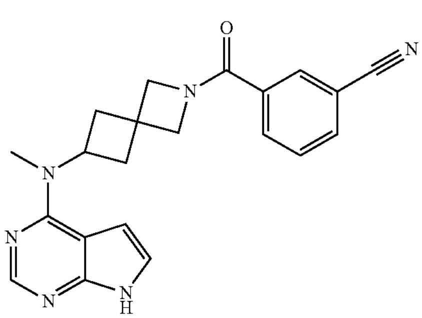 [SMILES: CN(c1ncnc2[nH]ccc12)C1CC2(C1)CN(C(=O)c1cccc(C#N)c1)C2] | 372.1/373.1 | 3-(6-(methyl(7H-pyrrolo[2,3-d]pyrimidin-4-yl)amino)-2-azaspiro[3.3]heptane-2-carbonyl)benzonitrile |

-continued

| Entry | Structure | MS (cald) [M + H]⁺/ MS (found) | Name |
|---|---|---|---|
| 12 | 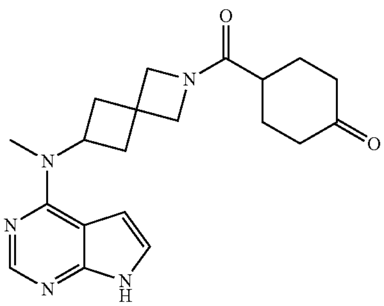 [SMILES: CN(c1ncnc2[nH]ccc12)C1CC2(C1)CN(C(=O)C1CCC(=O)CC1)C2] | 368.2/368.2 | 4-(6-(methyl(7H-pyrrolo[2,3-d]pyrimidin-4-yl)amino)-2-azaspiro[3.3]heptane-2-carbonyl)cyclohexanone |
| 13 | 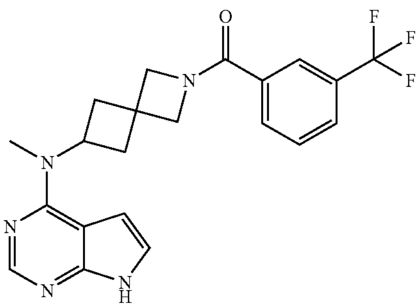 [SMILES: CN(c1ncnc2[nH]ccc12)C1CC2(C1)CN(C(=O)c1cccc(C(F)(F)F)c1)C2] | 415.1/416.1 | (6-(methyl(7H-pyrrolo[2,3-d]pyrimidin-4-yl)amino)-2-azasprio[3.3]heptan-2-yl)(3-(trifluoromethyl)phenyl)methanone |
| 14 | 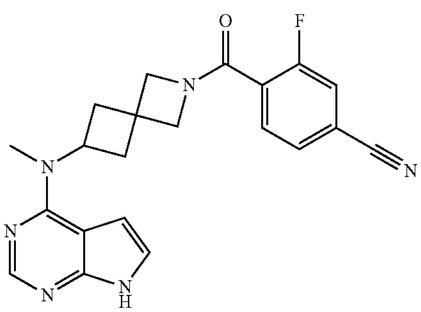 | 390.1/391.1 | 3-fluoro-4-(6-(methyl(7H-pyrrolo[2,3-d]pyrimidin-4-yl)amino)-2-azaspiro[3.3]heptane-2-carbonyl)benzonitrile |
| 15 | 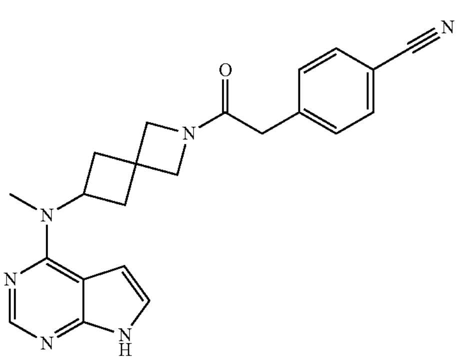 [SMILES: CN(c1ncnc2[nH]ccc12)C1CC2(C1)CN(C(=O)Cc1ccc(C#N)cc1)C2] | 387.1/387.1 | 4-(2-(6-(methyl(7H-pyrrolo[2,3-d]pyrimidin-4-yl)amino)-2-azaspiro[3.3]heptan-2-yl)-2-oxoethyl)benzonitrile |

-continued

| Entry | Structure | MS (cald) [M + H]+/ MS (found) | Name |
|---|---|---|---|
| 16 | 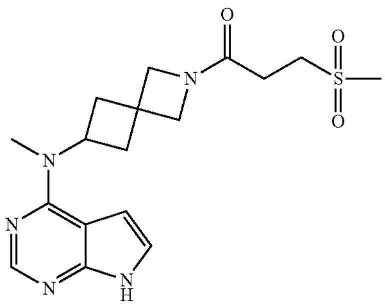 [SMILES: CN(c1ncnc2[nH]ccc12)C1CC2(C1)CN(C(=O)CCS(C)(=O)=O)C2] | 378.1378.13 | 1-(6-(methyl(7H-pyrrolo[2,3-d]pyrimidin-4-yl)amino)-2-azaspiro[3.3]heptan-2-yl)-3-(methylsulfonyl)propan-1-one |
| 17 | 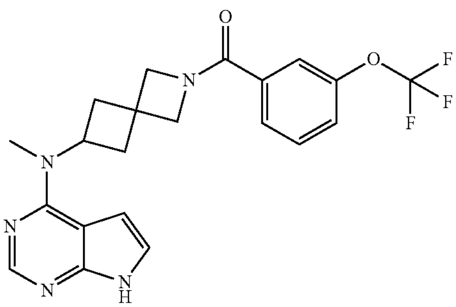 [SMILES: CN(c1ncnc2[nH]ccc12)C1CC2(C1)CN(C(=O)c1cccc(OC(F)(F)F)c1)C2] | 431.1/432.1 | (6-(methyl(7H-pyrrolo[2,3-d]pyrimidin-4-yl)amino)-2-azaspiro[3.3]heptan-2-yl)(3-(trifluoromethoxy)phenyl)methanone |
| 18 | 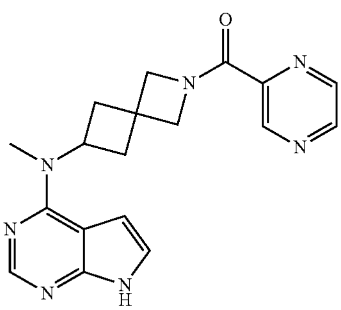 [SMILES: CN(c1ncnc2[nH]ccc12)C1CC2(C1)CN(C(=O)c1cnccn1)C2] | 349.1/350.1 | (6-(methyl(7H-pyrrolo[2,3-d]pyrimidin-4-yl)amino)-2-azaspiro[3.3]heptan-2-yl)(pyrazin-2-yl)methanone |
| 19 | 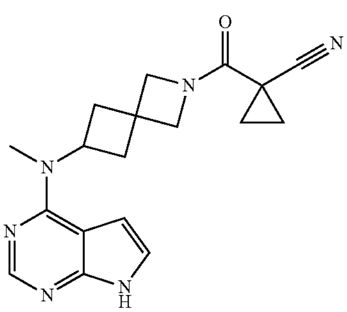 [SMILES: CN(c1ncnc2[nH]ccc12)C1CC2(C1)CN(C(=O)C1(C#N)CC1)C2] | 336.1/337.1 | 1-(6-(methyl(7H-pyrrolo[2,3-d]pyrimidin-4-yl)amino)-2-azaspiro[3.3]heptane-2-carbonyl)cyclopropanecarbonitrile |
| 20 | 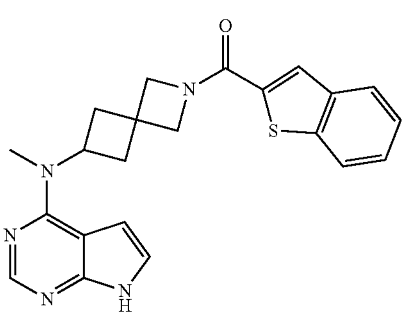 [SMILES: CN(c1ncnc2[nH]ccc12)C1CC2(C1)CN(C(=O)c1cc3ccccc3s1)C2] | 403.1/404.1 | benzo[b]thiophen-2-yl(6-(methyl(7H-pyrrolo[2,3-d]pyrimidin-4-yl)amino)-2-azaspiro[3.3]heptan-2-yl)methanone |

-continued

| Entry | Structure | MS (cald) [M + H]+/ MS (found) | Name |
|---|---|---|---|
| 21 | 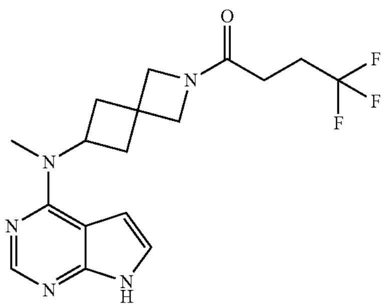 [SMILES: CN(c1ncnc2[nH]ccc12)C1CC2(C1)CN(C(=O)CCC(F)(F)F)C2] | 367.1/368.1 | 4,4,4-trifluoro-1-(6-(methyl(7H-pyrrolo[2,3-d]pyrimidin-4-yl)amino)-2-azaspiro[3.3]heptan-2-yl)butan-1-one |
| 22 | 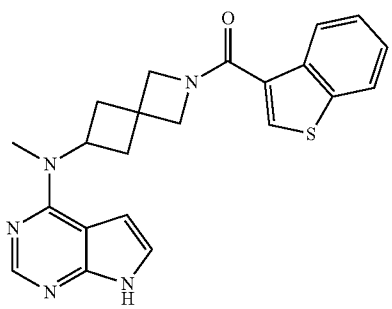 [SMILES: CN(c1ncnc2[nH]ccc12)C1CC2(C1)CN(C(=O)c1csc3ccccc13)C2] | 403.1/404.1 | benzo[b]thiophen-3-yl(6-(methyl(7H-pyrrolo[2,3-d]pyrimidin-4-yl)amino)-2-azaspiro[3.3]heptan-2-yl)methanone |
| 23 | 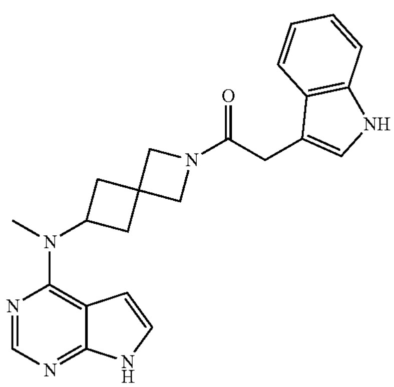 [SMILES: CN(c1ncnc2[nH]ccc12)C1CC2(C1)CN(C(=O)Cc1c[nH]c3ccccc13)C2] | 400.1/401.1 | 2-(1H-indol-3-yl)-1-(6-(methyl(7H-pyrrolo[2,3-d]pyrimidin-4-yl)amino)-2-azaspiro[3.3]heptan-2-yl)ethanone |
| 24 | 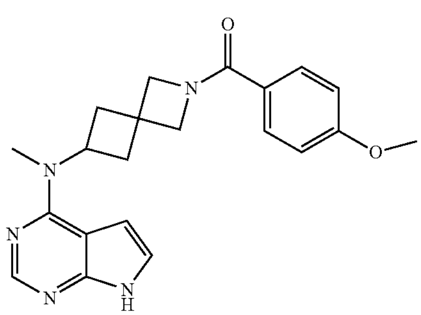 [SMILES: COc1ccc(C(=O)N2CC3(CC(N(C)c4ncnc5[nH]ccc45)C3)C2)cc1] | 377.1/378.1 | (4-methoxyphenyl)(6-(methyl(7H-pyrrolo[2,3-d]pyrimidin-4-yl)amino)-2-azaspiro[3.3]heptan-2-yl)methanone |

-continued

| Entry | Structure | MS (cald) [M + H]+/ MS (found) | Name |
|---|---|---|---|
| 25 | 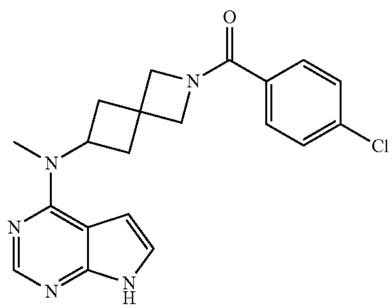 [SMILES: CN(c1ncnc2[nH]ccc12)C1CC2(C1)CN(C(=O)c1ccc(Cl)cc1)C2] | 381.1/382.1 | (4-chlorophenyl)(6-(methyl(7H-pyrrolo[2,3-d]pyrimidin-4-yl)amino)-2-azaspiro[3.3]heptan-2-yl)methanone |
| 26 | 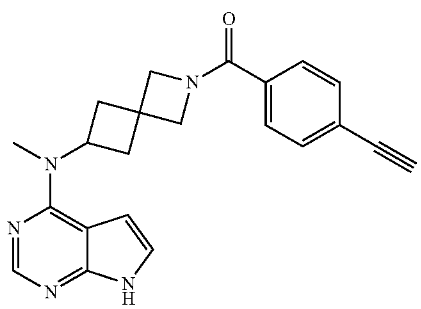 [SMILES: C#Cc1ccc(C(=O)N2CC3(CC(N(C)c4ncnc5[nH]ccc45)C3)C2)cc1] | 371.1/372.1 | (4-ethynylphenyl)(6-(methyl(7H-pyrrolo[2,3-d]pyrimidin-4-yl)amino)-2-azaspiro[3.3]heptan-2-yl)methanone |
| 27 | 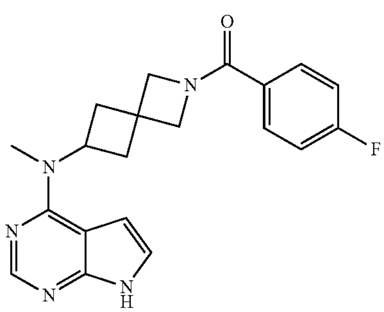 [SMILES: CN(c1ncnc2[nH]ccc12)C1CC2(C1)CN(C(=O)c1ccc(F)cc1)C2] | 365.1/366.1 | (4-fluorophenyl)(6-(methyl(7H-pyrrolo[2,3-d]pyrimidin-4-yl)amino)-2-azaspiro[3.3]heptan-2-yl)methanone |
| 28 | 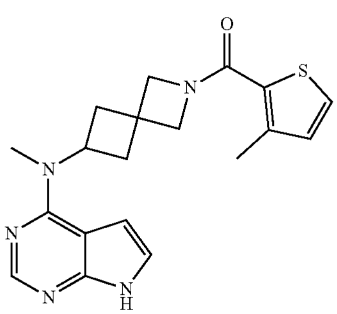 [SMILES: Cc1ccsc1C(=O)N1CC2(CC(N(C)c3ncnc4[nH]ccc34)C2)C1] | 367.1/368.1 | (6-(methyl(7H-pyrrolo[2,3-d]pyrimidin-4-yl)amino)-2-azaspiro[3.3]heptan-2-yl)(3-methylthiophen-2-yl)methanone |
| 29 | 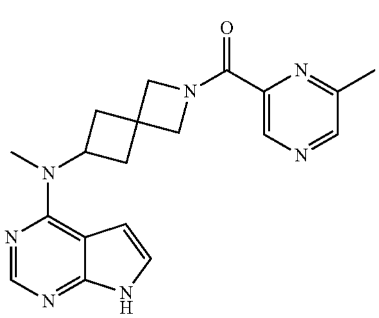 [SMILES: Cc1cncc(C(=O)N2CC3(CC(N(C)c4ncnc5[nH]ccc45)C3)C2)n1] | 363.1/364.1 | (6-(methyl(7H-pyrrolo[2,3-d]pyrimidin-4-yl)amino)-2-azaspiro[3.3]heptan-2-yl)(6-methylpyrazin-2-yl)methanone |

-continued

| Entry | Structure | MS (cald) [M + H]+/ MS (found) | Name |
|---|---|---|---|
| 30 | 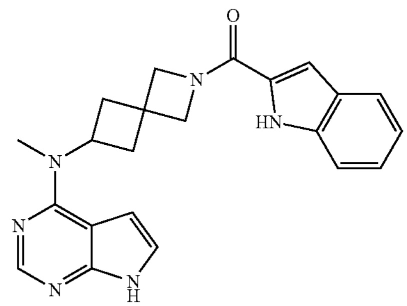 [SMILES: CN(c1ncnc2[nH]ccc12)C1CC2(C1)CN(C(=O)c1cc3ccccc3[nH]1)C2] | 386.1/387.1 | (1H-indol-2-yl)(6-(methyl(7H-pyrrolo[2,3-d]pyrimidin-4-yl)amino)-2-azaspiro[3.3]heptan-2-yl)methanone |
| 31 | 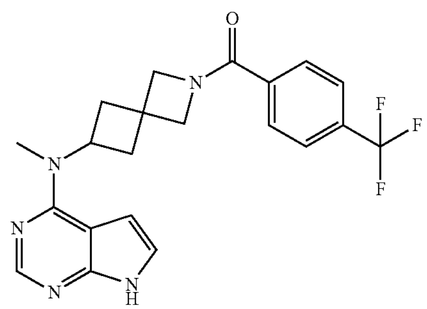 [SMILES: CN(c1ncnc2[nH]ccc12)C1CC2(C1)CN(C(=O)c1ccc(C(F)(F)F)cc1)C2] | 415.1/416.1 | (6-(methyl(7H-pyrrolo[2,3-d]pyrimidin-4-yl)amino)-2-azaspiro[3.3]heptan-2-yl)(4-(trifluoromethyl)phenyl)methanone |
| 32 | 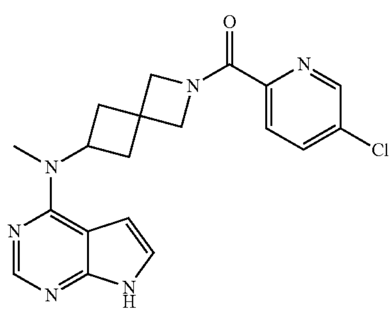 [SMILES: CN(c1ncnc2[nH]ccc12)C1CC2(C1)CN(C(=O)c1ccc(Cl)cn1)C2] | 382.1/383.1 | (5-chloropyridin-2-yl)(6-(methyl(7H-pyrrolo[2,3-d]pyrimidin-4-yl)amino)-2-azaspiro[3.3]heptan-2-yl)methanone |
| 33 | 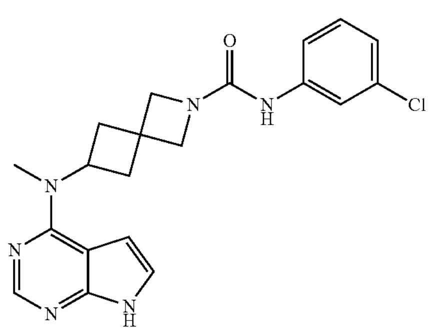 [SMILES: CN(c1ncnc2[nH]ccc12)C1CC2(C1)CN(C(=O)Nc1cccc(Cl)c1)C2] | 396.1/397.1 | N-(3-chlorophenyl)-6-(methyl(7H-pyrrolo[2,3-d]pyrimidin-4-yl)amino)-2-azaspiro[3.3]heptane-2-carboxamide |
| 34 | 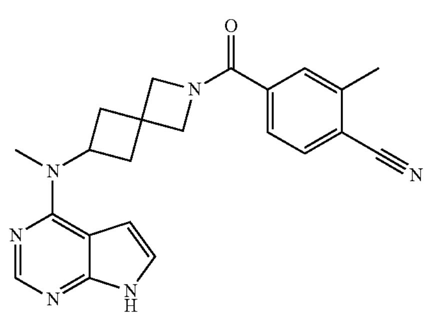 [SMILES: Cc1cc(C(=O)N2CC3(CC(N(C)c4ncnc5[nH]ccc45)C3)C2)ccc1C#N] | 386.1/387.1 | 2-methyl-4-(6-(methyl(7H-pyrrolo[2,3-d]pyrimidin-4-yl)amino)-2-azaspiro[3.3]heptane-2-carbonyl)benzonitrile |

-continued

| Entry | Structure | MS (cald) [M + H]⁺/ MS (found) | Name |
|---|---|---|---|
| 35 | 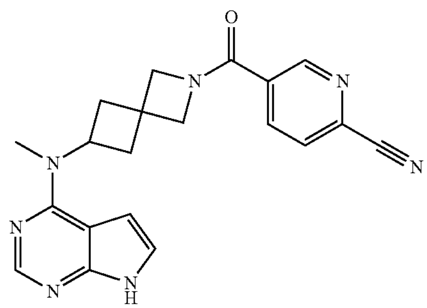 [SMILES: CN(c1ncnc2[nH]ccc12)C1CC2(C1)CN(C(=O)c1ccc(C#N)nc1)C2] | 373.1/374.1 | 5-(6-(methyl(7H-pyrrolo[2,3-d]pyrimidin-4-yl)amino)-2-azaspiro[3.3]heptane-2-carbonyl)picolinonitrile |
| 36 | 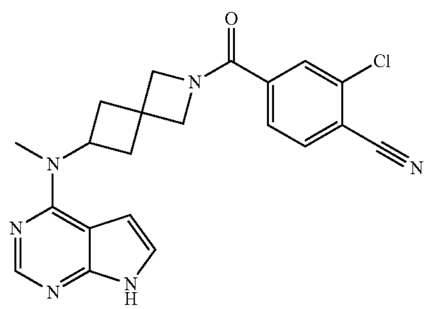 [SMILES: CN(c1ncnc2[nH]ccc12)C1CC2(C1)CN(C(=O)c1ccc(C#N)c(Cl)c1)C2] | 406.1/407.1 | 2-chloro-4-(6-(methyl(7H-pyrrolo[2,3-d]pyrimidin-4-yl)amino)-2-azaspiro[3.3]heptane-2-carbonyl)benzonitrile |
| 37 | 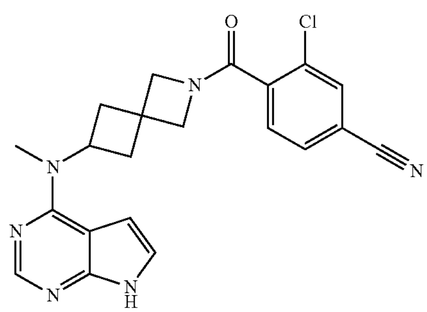 | 406.1/407.1 | 3-chloro-4-(6-(methyl(7H-pyrrolo[2,3-d]pyrimidin-4-yl)amino)-2-azaspiro[3.3]heptane-2-carbonyl)benzonitrile |
| 38 | 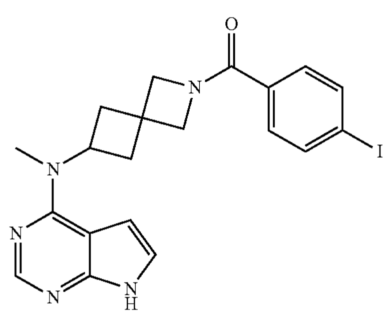 [SMILES: CN(c1ncnc2[nH]ccc12)C1CC2(C1)CN(C(=O)c1ccc(I)cc1)C2] | 473.1/474.1 | (4-iodophenyl)(6-(methyl(7H-pyrrolo[2,3-d]pyrimidin-4-yl)amino)-2-azaspiro[3.3]heptan-2-yl)methanone |
| 39 | 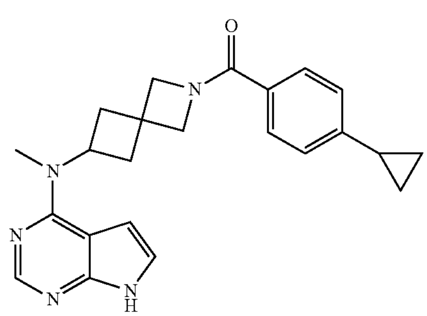 [SMILES: CN(c1ncnc2[nH]ccc12)C1CC2(C1)CN(C(=O)c1ccc(C3CC3)cc1)C2] | 387.2/388.2 | (4-cyclopropylphenyl)(6-(methyl(7H-pyrrolo[2,3-d]pyrimidin-4-yl)amino)-2-azaspiro[3.3]heptan-2-yl)methanone |

-continued

| Entry | Structure | MS (cald) [M + H]+/ MS (found) | Name |
|---|---|---|---|
| 40 | 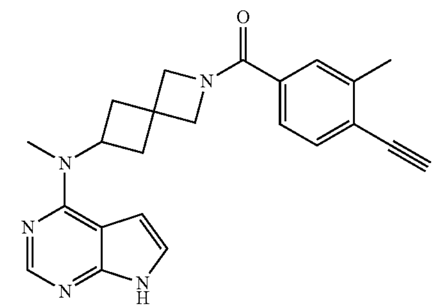 [SMILES: C#Cc1ccc(C(=O)N2CC3(CC(N(C)c4ncnc5[nH]ccc45)C3)C2)cc1C] | 356.1/357.1 | (4-ethynyl-3-methylphenyl)(6-(methyl(7H-pyrrolo[2,3-d]pyrimidin-4-yl)amino)-2-azaspiro[3.3]heptan-2-yl)methanone |
| 41 | 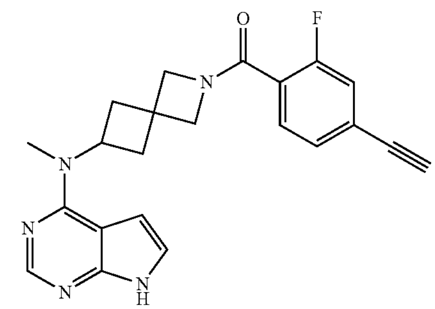 [SMILES: C#Cc1ccc(C(=O)N2CC3(CC(N(C)c4ncnc5[nH]ccc45)C3)C2)c(F)c1] | 389.2/390.2 | (4-ethynyl-2-fluorophenyl)(6-(methyl(7H-pyrrolo[2,3-d]pyrimidin-4-yl)amino)-2-azaspiro[3.3]heptan-2-yl)methanone |
| 42 | 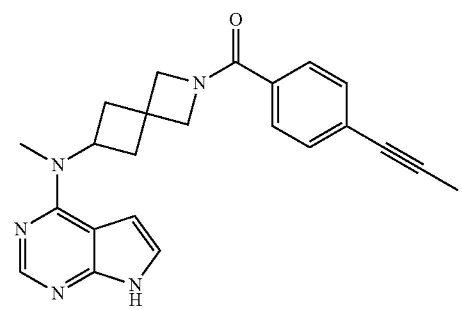 [SMILES: CC#Cc1ccc(C(=O)N2CC3(CC(N(C)c4ncnc5[nH]ccc45)C3)C2)cc1] | 356.1/357.1 | (6-(methyl(7H-pyrrolo[2,3-d]pyrimidin-4-yl)amino)-2-azaspiro[3.3]heptan-2-yl)(4-(prop-1-yn-1-yl)phenyl)methanone |
| 43 | 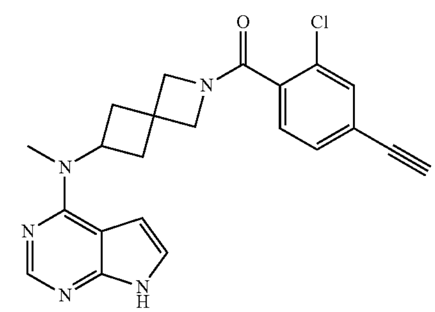 | 405.1/406.1 | (2-chloro-4-ethynylphenyl)(6-(methyl(7H-pyrrolo[2,3-d]pyrimidin-4-yl)amino)-2-azaspiro[3.3]heptan-2-yl)methanone |
| 44 | 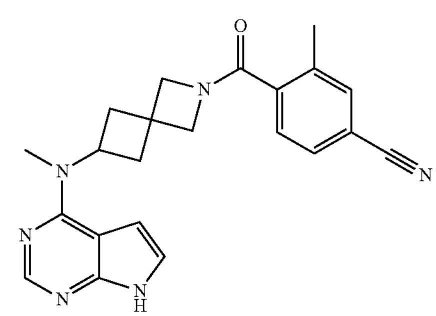 [SMILES: Cc1cc(C#N)ccc1C(=O)N1CC2(CC(N(C)c3ncnc4[nH]ccc34)C2)C1] | 386.1/387.1 | 3-methyl-4-(6-(methyl(7H-pyrrolo[2,3-d]pyrimidin-4-yl)amino)-2-azaspiro[3.3]heptane-2-carbonyl)benzonitrile |

-continued

| Entry | Structure | MS (cald) [M + H]+/ MS (found) | Name |
|---|---|---|---|
| 45 | 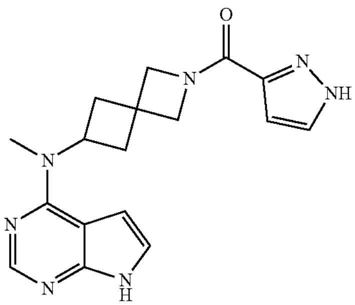 [SMILES: CN(c1ncnc2[nH]ccc12)C1CC2(C1)CN(C(=O)c1cc[nH]n1)C2] | 337.1/338.1 | (6-(methyl(7H-pyrrolo[2,3-d]pyrimidin-4-yl)amino)-2-azaspiro[3.3]heptan-2-yl)(1H-pyrazol-3-yl)methanone |
| 46 | 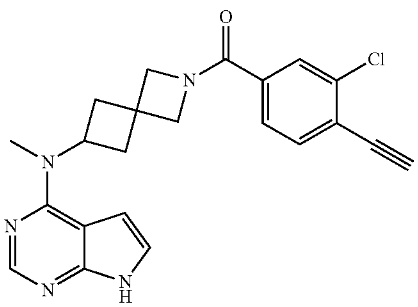 [SMILES: C#Cc1ccc(C(=O)N2CC3(CC(N(C)c4ncnc5[nH]ccc45)C3)C2)cc1Cl] | 405.1/406.1 | (3-chloro-4-ethynylphenyl)(6-(methyl(7H-pyrrolo[2,3-d]pyrimidin-4-yl)amino)-2-azaspiro[3.3]heptan-2-yl)methanone |
| 47 | 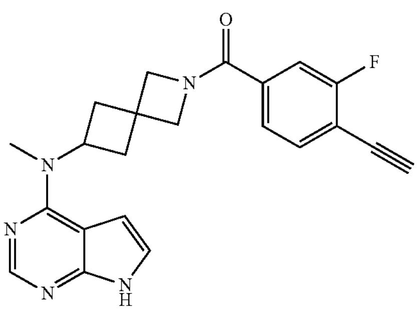 [SMILES: C#Cc1ccc(C(=O)N2CC3(CC(N(C)c4ncnc5[nH]ccc45)C3)C2)cc1F] | 389.1/390.1 | (4-ethynyl-3-fluorophenyl)(6-(methyl(7H-pyrrolo[2,3-d]pyrimidin-4-yl)amino)-2-azaspiro[3.3]heptan-2-yl)methanone |
| 48 | 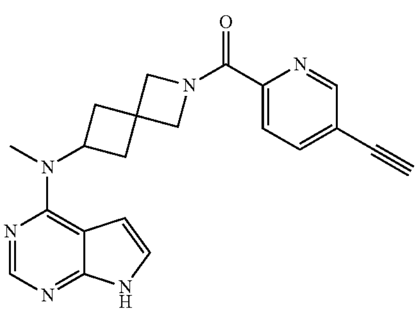 [SMILES: C#Cc1ccc(C(=O)N2CC3(CC(N(C)c4ncnc5[nH]ccc45)C3)C2)nc1] | 372.1/373.1 | (5-ethynylpyridin-2-yl)(6-(methyl(7H-pyrrolo[2,3-d]pyrimidin-4-yl)amino)-2-azaspiro[3.3]heptan-2-yl)methanon |
| 49 | 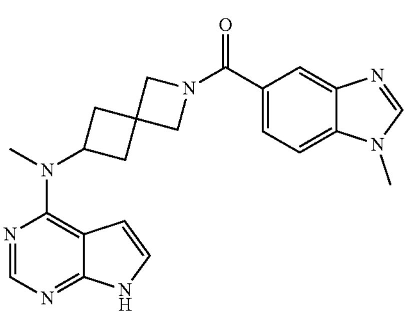 [SMILES: CN(c1ncnc2[nH]ccc12)C1CC2(C1)CN(C(=O)c1ccc3c(c1)ncn3C)C2] | 401.2/402.2 | (6-(methyl(7H-pyrrolo[2,3-d]pyrimidin-4-yl)amino)-2-azaspiro[3.3]heptan-2-yl)(1-methyl-1H-benzo[d]imidazol-5-yl)methanone |

-continued

| Entry | Structure | MS (cald) [M + H]+/ MS (found) | Name |
|---|---|---|---|
| 50 | 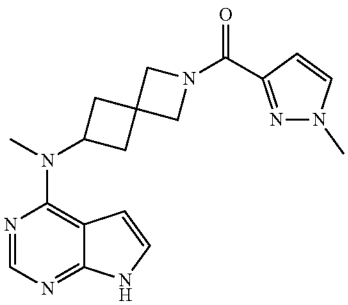 [SMILES: CN(c1ncnc2[nH]ccc12)C1CC2(C1)CN(C(=O)c1ccn(C)n1)C2] | 351.1/352.1 | (6-(methyl(7H-pyrrolo[2,3-d]pyrimidin-4-yl)amino)-2-azaspiro[3.3]heptan-2-yl)(1-methyl-1H-pyrazol-3-yl)methanone |
| 51 | 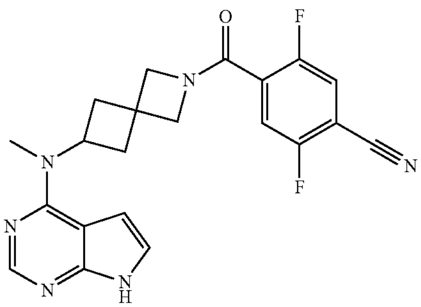 [SMILES: CN(c1ncnc2[nH]ccc12)C1CC2(C1)CN(C(=O)c1cc(F)c(C#N)cc1F)C2] | 408.2/409.2 | 2,5-difluoro-4-(6-(methyl(7H-pyrrolo[2,3-d]pyrimidin-4-yl)amino)-2-azaspiro[3.3]heptane-2-carbonyl)benzonitrile |
| 52 | 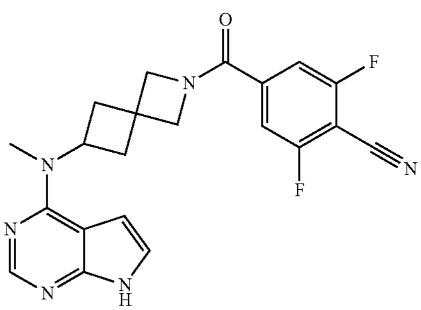 [SMILES: CN(c1ncnc2[nH]ccc12)C1CC2(C1)CN(C(=O)c1cc(F)c(C#N)c(F)c1)C2] | 408.2/409.1 | 2,6-difluoro-4-(6-(methyl(7H-pyrrolo[2,3-d]pyrimidin-4-yl)amino)-2-azaspiro[3.3]heptane-2-carbonyl)benzonitrile |
| 53 | 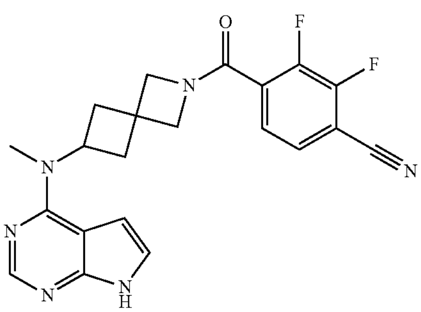 [SMILES: CN(c1ncnc2[nH]ccc12)C1CC2(C1)CN(C(=O)c1ccc(C#N)c(F)c1F)C2] | 408.2/409.2 | 2,3-difluoro-4-(6-(methyl(7H-pyrrolo[2,3-d]pyrimidin-4-yl)amino)-2-azaspiro[3.3]heptane-2-carbonyl)benzonitrile |
| 54 | 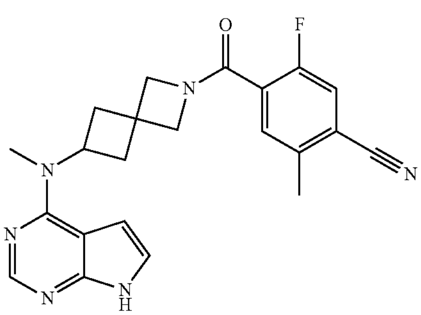 [SMILES: Cc1cc(C(=O)N2CC3(CC(N(C)c4ncnc5[nH]ccc45)C3)C2)c(F)cc1C#N] | 404.2/405.1 | 5-fluoro-2-methyl-4-(6-(methyl(7H-pyrrolo[2,3-d]pyrimidin-4-yl)amino)-2-azaspiro[3.3]heptane-2-carbonyl)benzonitrile |

-continued

| Entry | Structure | MS (cald) [M + H]+/ MS (found) | Name |
|---|---|---|---|
| 55 | 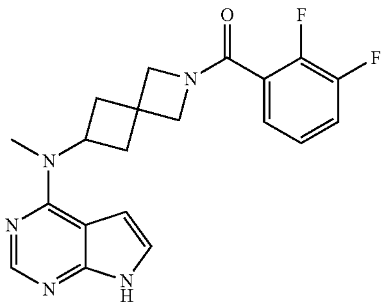 [SMILES: CN(c1ncnc2[nH]ccc12)C1CC2(C1)CN(C(=O)c1cccc(F)c1F)C2] | 383.2/384.2 | (2,3-difluorophenyl)(6-(methyl(7H-pyrrolo[2,3-d]pyrimidin-4-yl)amino)-2-azaspiro[3.3]heptan-2-yl)methanone |
| 56 | 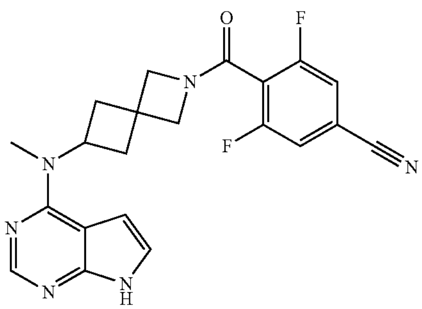 [SMILES: CN(c1ncnc2[nH]ccc12)C1CC2(C1)CN(C(=O)c1c(F)cc(C#N)cc1F)C2] | 408.2/409.2 | 3,5-difluoro-4-(6-(methyl(7H-pyrrolo[2,3-d]pyrimidin-4-yl)amino)-2-azaspiro[3.3]heptane-2-carbonyl)benzonitrile |
| 57 | 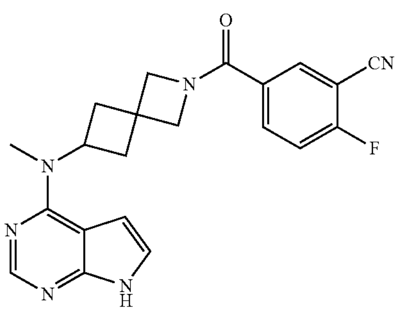 [SMILES: CN(c1ncnc2[nH]ccc12)C1CC2(C1)CN(C(=O)c1ccc(F)c(C#N)c1)C2] | 390.1/391.1 | 2-Fluoro-5-{6-[methyl-(7H-pyrrolo[2,3-d]pyrimidin-4-yl)-amino]-2-aza-spiro[3.3]heptane-2-carbonyl}-benzonitrile |
| 58 | 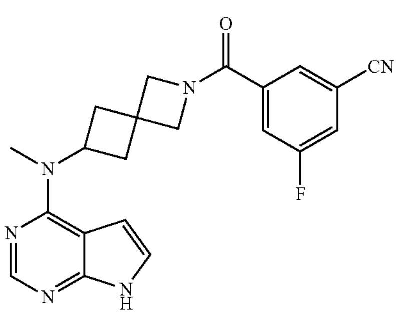 [SMILES: CN(c1ncnc2[nH]ccc12)C1CC2(C1)CN(C(=O)c1cc(F)cc(C#N)c1)C2] | 390.1/391.1 | 3-Fluoro-5-{6-[methyl-(7H-pyrrolo[2,3-d]pyrimidin-4-yl)-amino]-2-aza-spiro[3.3]heptane-2-carbonyl}-benzonitrile |
| 59 | 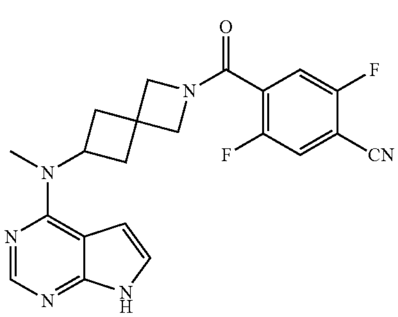 [SMILES: CN(c1ncnc2[nH]ccc12)C1CC2(C1)CN(C(=O)c1cc(F)c(C#N)cc1F)C2] | 408.1/409.1 | 2,5-Difluoro-4-{6-[methyl-(7H-pyrrolo[2,3-d]pyrimidin-4-yl)-amino]-2-aza-spiro[3.3]heptane-2-carbonyl}-benzonitrile |

-continued

| Entry | Structure | MS (cald) [M + H]+/ MS (found) | Name |
|---|---|---|---|
| 60 | 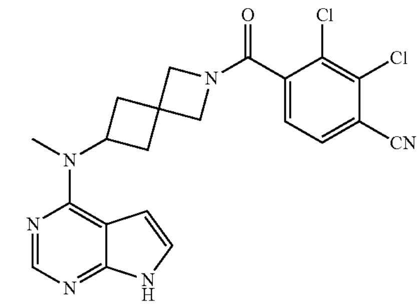 [SMILES: CN(c1ncnc2[nH]ccc12)C1CC2(C1)CN(C(=O)c1ccc(C#N)c(Cl)c1Cl)C2] | 440.1/441.1, 443.1 | 2,3-Dichloro-4-{6-[methyl-(7H-pyrrolo[2,3-d]pyrimidin-4-yl)-amino]-2-aza-spiro[3.3]heptane-2-carbonyl}-benzonitrile |
| 61 | 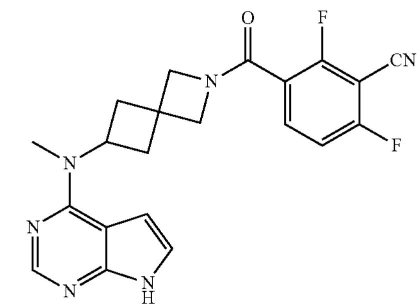 [SMILES: CN(c1ncnc2[nH]ccc12)C1CC2(C1)CN(C(=O)c1ccc(F)c(C#N)c1F)C2] | 408.2/409.2, 410.2 | 2,6-Difluoro-3-{6-[methyl-(7H-pyrrolo[2,3-d]pyrimidin-4-yl)-amino]-2-aza-spiro[3.3]heptane-2-carbonyl}-benzonitrile |
| 62 | 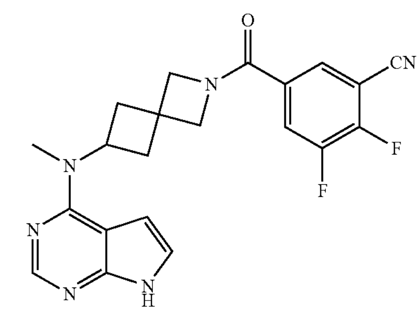 [SMILES: CN(c1ncnc2[nH]ccc12)C1CC2(C1)CN(C(=O)c1cc(F)c(F)c(C#N)c1)C2] | 408.1/409.2, 410.2 | 2,3-Difluoro-5-{6-[methyl-(7H-pyrrolo[2,3-d]pyrimidin-4-yl)-amino]-2-aza-spiro[3.3]heptane-2-carbonyl}-benzonitrile |
| 63 | 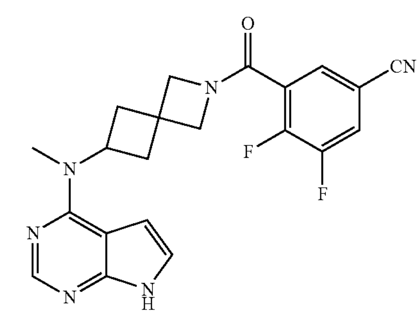 [SMILES: CN(c1ncnc2[nH]ccc12)C1CC2(C1)CN(C(=O)c1cc(C#N)cc(F)c1F)C2] | 408.1/409.2, 410.2 | 3,4-Difluoro-5-{6-[methyl-(7H-pyrrolo[2,3-d]pyrimidin-4-yl)-amino]-2-aza-spiro[3.3]heptane-2-carbonyl}-benzonitrile |
| 64 | 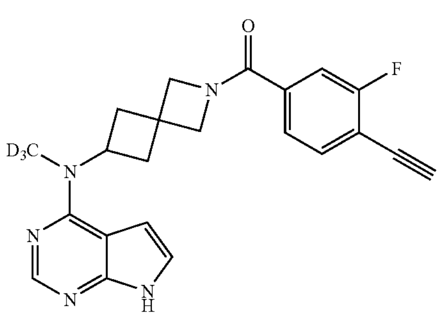 [SMILES: [2H]C([2H])([2H])N(c1ncnc2[nH]ccc12)C1CC2(C1)CN(C(=O)c1ccc(C#C)c(F)c1)C2] | 392.2/393.2, 394.2 | (4-Ethynyl-3-fluoro-phenyl)-{6-[(methyl-d3)-(7H-pyrrolo[2,3-d]pyrimidin-4-yl)-amino]-2-aza-spiro[3.3]hept-2-yl}-methanone |

-continued

| Entry | Structure | MS (cald) [M + H]+/ MS (found) | Name |
|---|---|---|---|
| 65 | 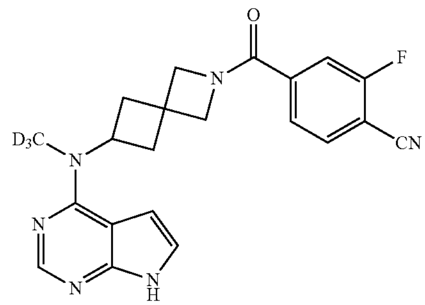 [SMILES: [2H]C([2H])([2H])N(c1ncnc2[nH]ccc12)C1CC2(C1)CN(C(=O)c1ccc(C#N)c(F)c1)C2] | 393.2/394.3, 395.2 | 2-Fluoro-4-{6-[-[(methyl-d3)-(7H-pyrrolo[2,3-d]pyrimidin-4-yl)-amino]-2-aza-spiro[3.3]heptane-2-carbonyl}-benzonitrile |
| 66 | 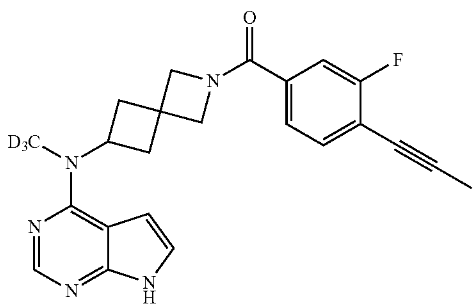 [SMILES: [2H]C([2H])([2H])N(c1ncnc2[nH]ccc12)C1CC2(C1)CN(C(=O)c1ccc(C#CC)c(F)c1)C2] | 406.2/407.3, 408.3 | (3-Fluoro-4-prop-1-ynyl-phenyl)-{6-[-[(methyl-d3)-(7H-pyrrolo[2,3-d]pyrimidin-4-yl)-amino]-2-aza-spiro[3.3]hept-2-yl}-methanone |
| 67 | 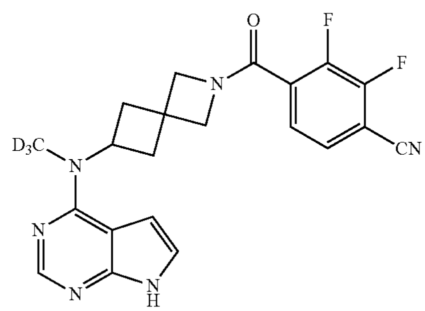 [SMILES: [2H]C([2H])([2H])N(c1ncnc2[nH]ccc12)C1CC2(C1)CN(C(=O)c1ccc(C#N)c(F)c1F)C2] | 411.2/412.2, 413.2, 414.2 | 2,3-Difluoro-4-{6-[(methyl-d3)-(7H-pyrrolo[2,3-d]pyrimidin-4-yl)-amino]-2-aza-spiro[3.3]heptane-2-carbonyl}-benzonitrile |
| 68 | 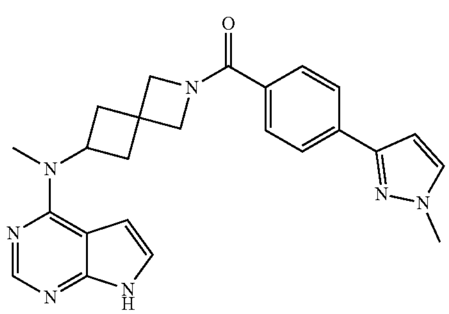 [SMILES: CN(c1ncnc2[nH]ccc12)C1CC2(C1)CN(C(=O)c1ccc(-c3ccn(C)n3)cc1)C2] | 427.2/428.2 | [4-(1-Methyl-1H-pyrazol-3-yl)-phenyl-{6-[methyl-(7H-pyrrolo[2,3-d]pyrimidin-4-yl)-amino]-2-aza-spiro[3.3]hept-2-yl}-methanone |
| 69 | 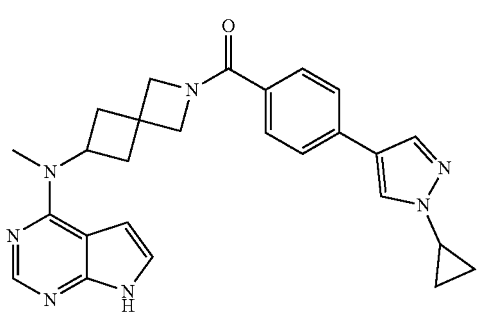 [SMILES: CN(c1ncnc2[nH]ccc12)C1CC2(C1)CN(C(=O)c1ccc(-c3cnn(C4CC4)c3)cc1)C2] | 377.2/378.2 | (1-Cyclopropyl-1H-pyrazol-4-yl)-{6-[methyl-(7H-pyrrolo[2,3-d]pyrimidin-4-yl)-amino]-2-aza-spiro[3.3]hept-2-yl}-methanone |

| Entry | Structure | MS (cald) [M + H]+/ MS (found) | Name |
|---|---|---|---|
| 70 | 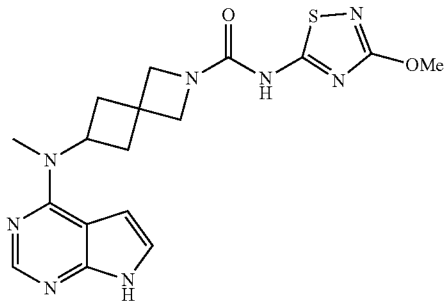 [SMILES: COc1nsc(NC(=O)N2CC3(CC(N(C)c4ncnc5[nH]ccc45)C3)C2)n1] | 400.1/401.2, 402.2 | N-(3-methoxy-1,2,4-thiadiazol-5-yl)-6-(methyl(7H-pyrrolo[2,3-d]pyrimidin-4-yl)amino)-2-azaspiro[3.3]heptane-2-carboxamide |
| 71 | 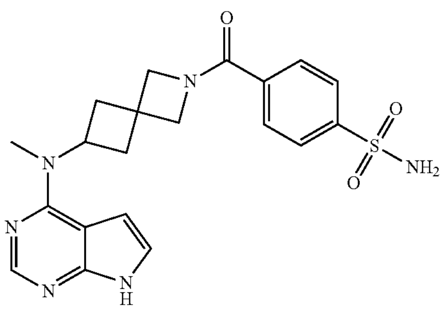 [SMILES: CN(c1ncnc2[nH]ccc12)C1CC2(C1)CN(C(=O)c1ccc(S(N)(=O)=O)cc1)C2] | 426.1/427.2 | 4-(6-(methyl(7H-pyrrolo[2,3-d]pyrimidin-4-yl)amino)-2-azaspiro[3.3]heptane-2-carbonyl)benzenesulfonamide |
Example 72: 2-methoxy-1-(9-(methyl(7H-pyrrolo[2,3-d]pyrimidin-4-yl)amino)-3-azaspiro[5.5]undecan-3-yl)ethan-1-one
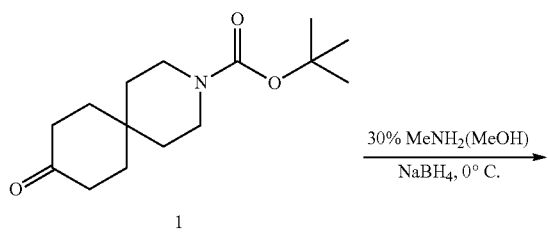
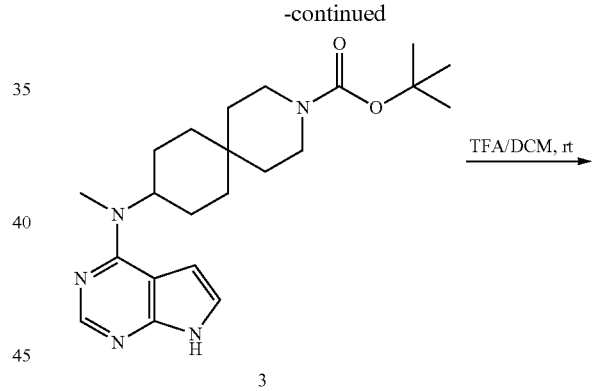
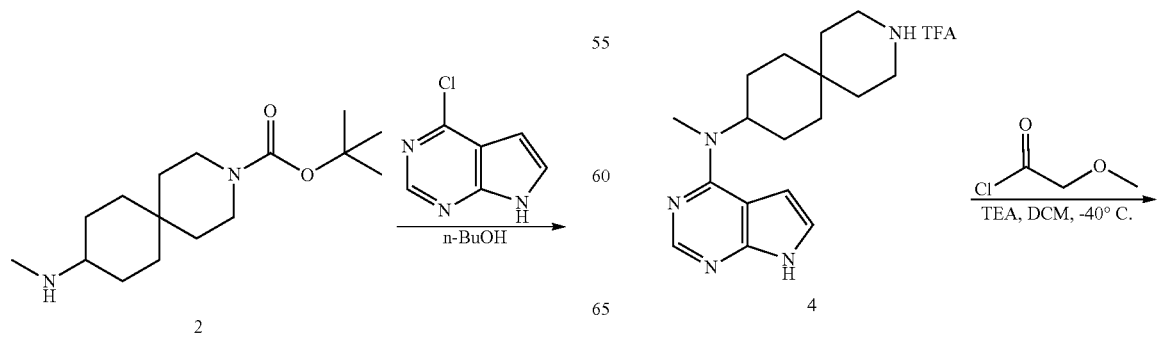

-continued

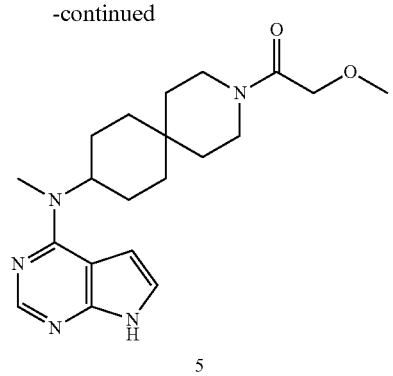

5

Step A: tert-butyl 9-(methyl amino)-3-azaspiro[5.5]undecane-3-carboxylate (2)

To a mixture of tert-butyl 6-oxo-2-azaspiro[3.3]heptane-2-carboxylate (1, 3.0 g, 11.22 mmol) in MeOH (40 mL) was added 30% MeNH$_2$ in MeOH (5.8 g, 56.10 mmol) under ice cooling. The resulting mixture was stirred for 5 hours at 25° C. under N$_2$, and cooled to −10° C., followed by careful addition of NaBH$_4$ (0.85 g, 22.40 mmol) in small portions. The reaction mixture was stirred for 3 hours at rt. TLC showed starting mixture was consumed. The reaction mixture was quenched with sat. NH$_4$Cl (25 mL) and the solvent was removed under reduced pressure. The residue was adjusted pH to 3 with citrate solution (50 mL). Then the aqueous layer was washed with EA (20 mL×2), basified to pH=10 by 30% NaOH, and extracted with EA (50 mL×3). The organic phase was washed with brine, dried over Na$_2$SO$_4$ and filtered. The filtrate was concentrated to afford the desired product 2 (3.1 g, 95.7%) as colorless oil. $^1$H NMR (400 MHz, CDCl$_3$): δ 3.40-3.30 (m, 4H), 2.42 (s, 3H), 2.33 (dd, J=11.7, 7.9 Hz, 1H), 1.80-1.64 (m, 4H), 1.47 (d, J=11.9 Hz, 12H), 1.33-1.28 (m, 2H), 1.19 (dd, J=24.5, 13.3 Hz, 4H).

Step B: tert-butyl 9-(methyl(7H-pyrrolo[2,3-d]pyrimidin-4-yl)amino)-3-azaspiro[5.5]undecane-3-carboxylate (3)

The mixture of 2 (1.55 g, 5.50 mmol), 4-chloro-7H-pyrrolo[2,3-d]pyrimidine (0.85 g, 5.50 mmol) and sodium carbonate (1.20 g, 11.0 mol) in n-BnOH (30 mL) was stirred at 120° C. for 16 hours under N$_2$. The reaction mixture was cooled to rt and dichloromethane (150 mL) was added. The organic phase was washed with brine (50 mL×2), dried over Na$_2$SO$_4$ and filtered. The filtrate was concentrated. The residue was recrystallization with EA to afford the desired product 3 (1.5 g, 68.3%) as white solid. $^1$H NMR (400 MHz, CDCl$_3$): δ 8.07 (s, 1H), 7.07 (d, J=3.6 Hz, 1H), 6.60 (d, J=3.6 Hz, 1H), 4.66 (d, J=11.6 Hz, 1H), 3.42 (d, J=4.6 Hz, 4H), 3.28 (d, J=19.4 Hz, 3H), 1.88 (d, J=12.1 Hz, 4H), 1.70-1.57 (m, 4H), 1.46 (s, 9H), 1.42-1.29 (m, 4H). LC-MS: (ES$^+$): m/z 400.3 [M+H]$^+$. t$_R$=1.92 min

Step C: N-methyl-N-(7H-pyrrolo[2,3-d]pyrimidin-4-yl)-3-azaspiro[5.5]undecan-9-amine 2,2,2-trifluoroacetate salt (4)

To a mixture of tert-butyl 9-(methyl(7H-pyrrolo[2,3-d]pyrimidin-4-yl)amino)-3-azaspiro[5.5]undecane-3-carboxylate (3, 50 mg, 0.125 mmol) in DCM (2.0 mL) was added TFA (1.0 mL) and the resulting mixture was stirred for 1 hours at rt. The reaction mixture was concentrated to afford the crude product 4 (60 mg). LC-MS: (ES$^+$): m/z 300.2 [M+H]$^+$. t$_R$=0.92 min.

Step D: 2-methoxy-1-(9-(methyl(7H-pyrrolo[2,3-d]pyrimidin-4-yl)amino)-3-azaspiro[5.5]undecan-3-yl)ethan-1-one (5)

To a mixture of crude 4 (0.125 mmol) and triethylamine (36 mg, 0.36 mmol) in dichloromethane (2.0 mL) was added the solution of 2-methoxyacetyl chloride (13 mg, 0.125 mmol) in dichloromethane (1.0 mL) dropwise at −40° C. The reaction mixture was stirred at rt for 1 hour. Dichloromethane (50 mL) was added and the organic phase was washed with 5% sodium bicarbonate solution (20 mL), brine (20 mL), dried over sodium sulfate and filtered. The filtrate was concentrated and purified by Prep-TLC (DCM/MeOH=20/1) to afford the desired product 5 (15 mg, 32.2%). $^1$H NMR (400 MHz, CDCl$_3$): δ 11.45 (s, 1H), 8.32 (s, 1H), 7.06 (d, J=3.0 Hz, 1H), 6.47 (s, 1H), 4.77 (s, 1H), 4.11 (d, J=3.3 Hz, 2H), 3.60 (s, 2H), 3.44 (s, 5H), 3.27 (s, 3H), 1.93-1.61 (m, 8H), 1.41 (s, 4H). LC-MS: (ES$^+$): m/z 372.3 [M+H]$^+$. t$_R$=0.37 min.

Example 73: Methyl 9-(methyl(7H-pyrrolo[2,3-d]pyrimidin-4-yl)amino)-3-azaspiro[5.5]undecane-3-carboxylate

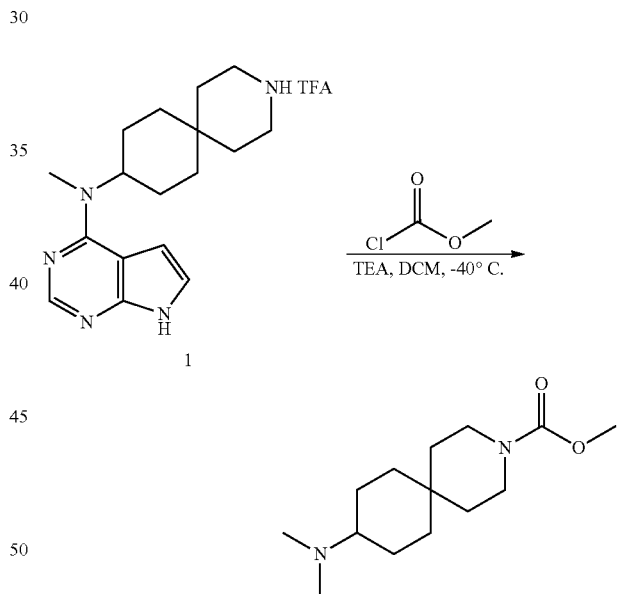

To a solution of 1 (0.2 g, 0.67 mmol), which was made through the same route as Example 72 and TEA (0.135 g, 1.3 L) in DCM (30 mL) at room temperature was added methyl carbonochloridate (0.06 g 0.67 μL) with stirring for 15 hrs. TLC monitored till the reaction showed that the reaction had gone to complete, the reaction mixture was washed with water (10 mL), the organic layer was concentrated under reduced pressure, the residue was purified by column chromatography (DCM:MeOH=50:1) to give target compound (50 mg, yield: 25%) as a white solid. 1H NMR (600 MHz, DMSO) δ 11.60 (s, 1H), 8.09 (s, 1H), 7.11 (m, 1H), 6.53 (s, 1H), 4.67 (s, 1H), 3.58 (s, 3H), 3.35 (dd, J=8.4, 4.5 Hz, 4H), 3.18 (s, 3H), 1.77 (dd, J=25.7, 12.8 Hz, 4H), 1.50 (m, 4H), 1.28 (dd, J=16.9, 9.8 Hz, 4H). MS: m/z [M+H]⁺ 357.1.

Example 74: N-(3-methoxy-1,2,4-thiadiazol-5-yl)-9-(methyl(7H-pyrrolo[2,3-d]pyrimidin-4-yl)amino)-3-azaspiro[5.5]undecane-3-carboxamide

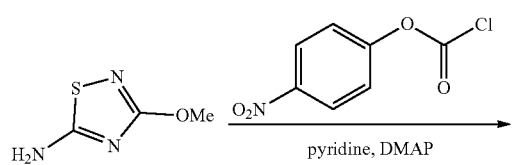

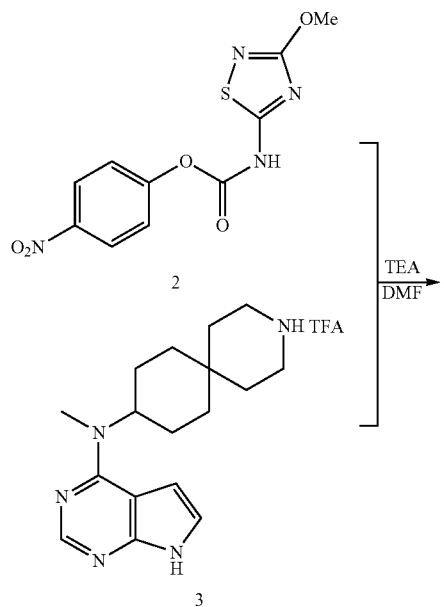

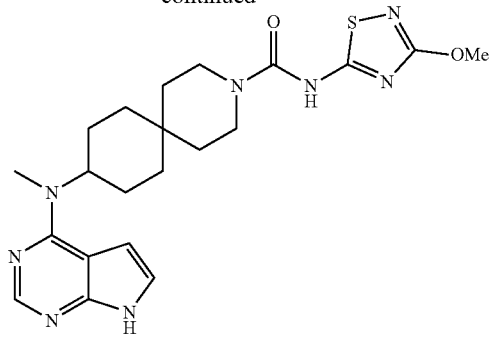

Step A: 4-nitrophenyl (3-methoxy-1,2,4-thiadiazol-5-yl)carbamate (2)

To a solution of 3-methoxy-1,2,4-thiadiazol-5-amine (1) (104 mg, 0.8 mmol), DMAP (10 mg, 0.8 mmol) in pyridine (5 mL). The mixture was cooled to 0° C. followed by 4-nitrophenyl carbonochloridate (160 mg, 0.8 mmol). The mixture was stirred at 0° C. for 0.5 h. The reaction mixture was allowed to warm to RT and further stirred for 20 h. TLC showed little SM remained. Water (10 mL) was added and the resulting suspension was filtered. The filter cake was washed with water and Et₂O. The white solid was dried to afford 2 (100 mg).

Step B: N-(3-methoxy-1,2,4-thiadiazol-5-yl)-9-(methyl(7H-pyrrolo[2,3-d]pyrimidin-4-yl)amino)-3-azaspiro[5.5]undecane-3-carboxamide (4)

To a solution of 3 (45 mg, 0.15 mmol), TEA (45 mg, 0.45 mmol) in DMF (2 mL) was added 2 (44 mg, 0.15 mmol). The mixture was stirred for 16 h. The reaction mixture was concentrated and residue was purified by Pre-HPLC to afford 4 (14 mg) as a white solid. ¹HNMR (400 MHz, DMSO-d₆): δ12.62 (s, 1H), 11.69 (s, 1H), 8.34 (s, 1H), 7.43 (s, 1H), 6.84 (s, 1H), 4.43 (s, 1H), 3.90 (s, 3H), 3.53 (s, 4H), 3.32 (s, 3H), 1.87-1.84 (m, 4H), 1.64-1.59 (m, 4H), 1.36-1.31 (m, 4H). LCMS: (ES⁺): m/z 457.2 [M]⁺, $t_R$=1.50 min.

The following additional Examples 75-135 shown in the Table below were prepared the following procedures outlined in the general methods above and detailed in Example 1, 72, 73 and 74.

| Entry | Structure | MS (cald) [M + H]⁺/ MS (found) | Name |
|---|---|---|---|
| 75 | 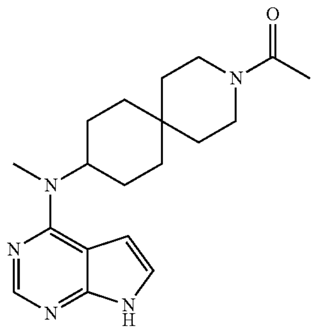 [SMILES: CC(=O)N1CCC2(CCC(N(C)c3ncnc4[nH]ccc34)CC2)CC1] | 341.2/342.2 | 1-{9-[Methyl-(7H-pyrrolo[2,3-d]pyrimidin-4-yl)-amino]-3-aza-spiro[5.5]undec-3-yl}-ethanone |
| 76 | 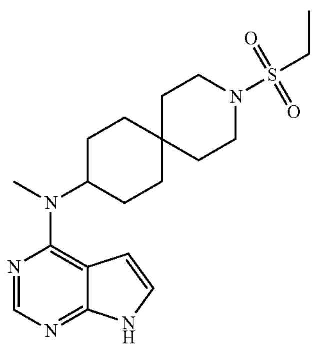 [SMILES: CCS(=O)(=O)N1CCC2(CCC(N(C)c3ncnc4[nH]ccc34)CC2)CC1] | 391.2/392.2 | (3-Ethanesulfonyl-3-aza-spiro[5.5]undec-9-yl)-methyl-(7H-pyrrolo[2,3-d]pyrimidin-4-yl)-amine |
| 77 | 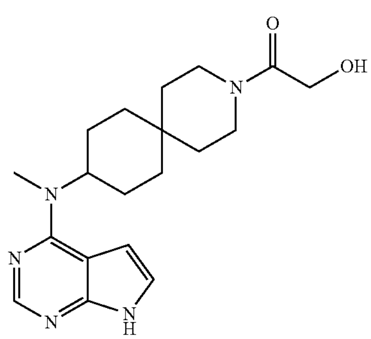 [SMILES: CN(c1ncnc2[nH]ccc12)C1CCC2(CC1)CCN(C(=O)CO)CC2] | 357.2/358.2 | 2-Hydroxy-1-{9-[methyl-(7H-pyrrolo[2,3-d]pyrimidin-4-yl)-amino]-3-aza-spiro[5.5]undec-3-yl}-ethanone |
| 78 | 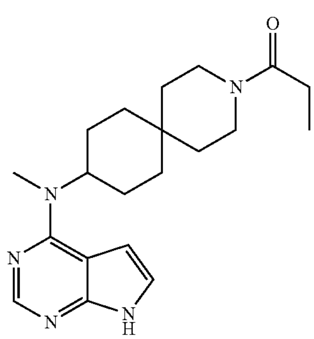 [SMILES: CCC(=O)N1CCC2(CCC(N(C)c3ncnc4[nH]ccc34)CC2)CC1] | 355.2/356.2 | 1-{9-[Methyl-(7H-pyrrolo[2,3-d]pyrimidin-4-yl)-amino]-3-aza-spiro[5.5]undec-3-yl}-propan-1-one |

-continued

| Entry | Structure | MS (cald) [M + H]+/ MS (found) | Name |
|---|---|---|---|
| 79 | 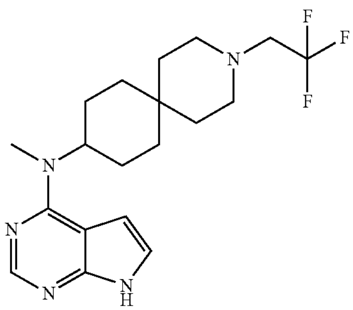 [SMILES: CN(c1ncnc2[nH]ccc12)C1CCC2(CC1)CCN(CC(F)(F)F)CC2] | 381.2/382.2 | Methyl-(7H-pyrrolo[2,3-d]pyrimidin-4-yl)-[3-(2,2,2-trifluoro-ethyl)-3-aza-spiro[5.5]undec-9-yl]-amine |
| 80 | 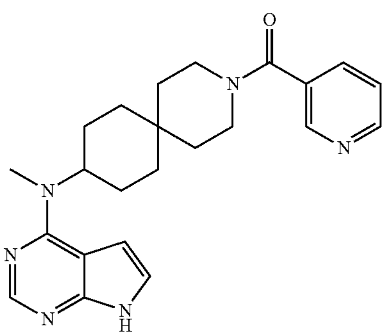 [SMILES: CN(c1ncnc2[nH]ccc12)C1CCC2(CC1)CCN(C(=O)c1cccnc1)CC2] | 404.2/405.2 | {9-[Methyl-(7H-pyrrolo[2,3-d]pyrimidin-4-yl)-amino]-3-aza-spiro[5.5]undec-3-yl}-pyridin-3-yl-methanone |
| 81 | 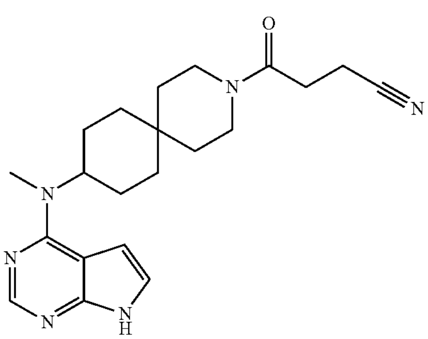 [SMILES: CN(c1ncnc2[nH]ccc12)C1CCC2(CC1)CCN(C(=O)CCC#N)CC2] | 380.2/381.2 | 4-{9-[Methyl-(7H-pyrrolo[2,3-d]pyrimidin-4-yl)-amino]-3-aza-spiro[5.5]undec-3-yl}-4-oxo-butyronitrile |
| 82 | 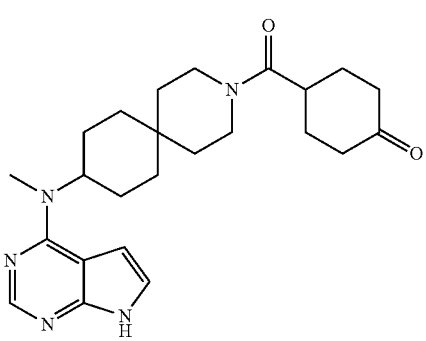 [SMILES: CN(c1ncnc2[nH]ccc12)C1CCC2(CC1)CCN(C(=O)C1CCC(=O)CC1)CC2] | 423.2/424.2 | 4-{9-[Methyl-(7H-pyrrolo[2,3-d]pyrimidin-4-yl)-amino]-3-aza-spiro[5.5]undecane-3-carbonyl}-cyclohexanone |

-continued

| Entry | Structure | MS (cald) [M + H]⁺/ MS (found) | Name |
|---|---|---|---|
| 83 | 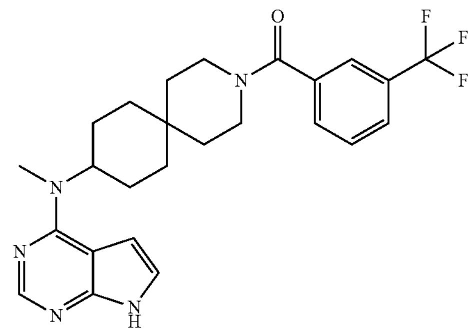 [SMILES: CN(c1ncnc2[nH]ccc12)C1CCC2(CC1)CCN(C(=O)c1cccc(C(F)(F)F)c1)CC2] | 471.2/472.2 | {9-[Methyl-(7H-pyrrolo[2,3-d]pyrimidin-4-yl)-amino]-3-aza-spiro[5.5]undec-3-yl}-(3-trifluoromethyl-phenyl)-methanone |
| 84 | 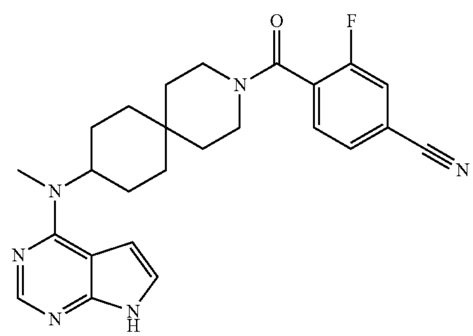 [SMILES: CN(c1ncnc2[nH]ccc12)C1CCC2(CC1)CCN(C(=O)c1ccc(C#N)cc1F)CC2] | 446.2/447.2 | 3-Fluoro-4-{9-[methyl-(7H-pyrrolo[2,3-d]pyrimidin-4-yl)-amino]-3-aza-spiro[5.5]undecane-3-carbonyl}-benzonitrile |
| 85 | 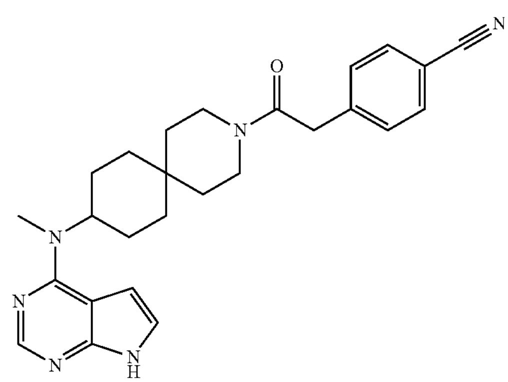 [SMILES: CN(c1ncnc2[nH]ccc12)C1CCC2(CC1)CCN(C(=O)Cc1ccc(C#N)cc1)CC2] | 442.2/443.2 | 4-(2-{9-[Methyl-(7H-pyrrolo[2,3-d]pyrimidin-4-yl)-amino]-3-aza-spiro[5.5]undec-3-yl}-2-oxo-ethyl)-benzonitrile |
| 86 | 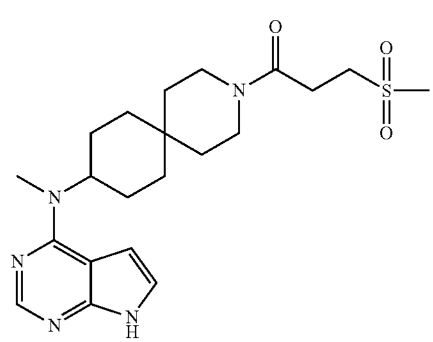 [SMILES: CN(c1ncnc2[nH]ccc12)C1CCC2(CC1)CCN(C(=O)CCS(C)(=O)=O)CC2] | 443.2/444.2 | 3-Methanesulfonyl-1-{9-[methyl-(7H-pyrrolo[2,3-d]pyrimidin-4-yl)-amino]-3-aza-spiro[5.5]undec-3-yl}-propan-1-one |

-continued

| Entry | Structure | MS (cald) [M + H]+/ MS (found) | Name |
|---|---|---|---|
| 87 | 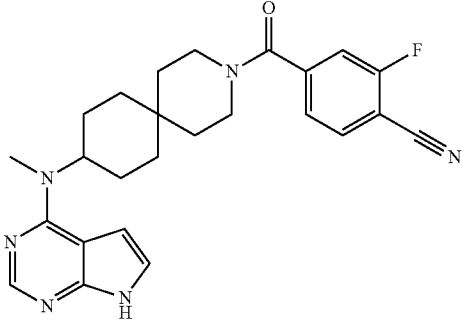 [SMILES: CN(c1ncnc2[nH]ccc12)C1CCC2(CC1)CCN(C(=O)c1ccc(C#N)c(F)c1)CC2] | 446.2/447.2 | 2-Fluoro-4-{9-[methyl-(7H-pyrrolo[2,3-d]pyrimidin-4-yl)-amino]-3-aza-spiro[5.5]undecane-3-carbonyl}-benzonitrile |
| 88 | 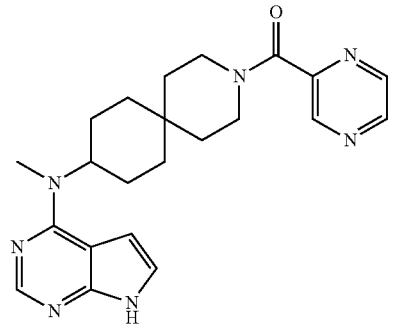 | 405.2/406.2 | {9-[Methyl-(7H-pyrrolo[2,3-d]pyrimidin-4-yl)-amino]-3-aza-spiro[5.5]undec-3-yl}-pyrazin-2-yl-methanone |
| 89 | 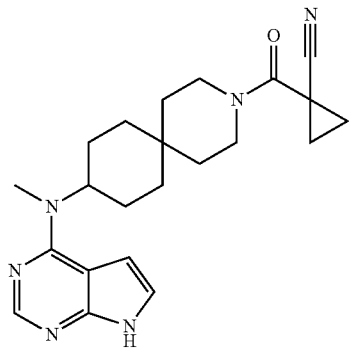 [SMILES: CN(c1ncnc2[nH]ccc12)C1CCC2(CC1)CCN(C(=O)C1(C#N)CC1)CC2] | 392.2/393.2 | 1-{9-[Methyl-(7H-pyrrolo[2,3-d]pyrimidin-4-yl)-amino]-3-aza-spiro[5.5]undecane-3-carbonyl}-cyclopropanecarbonitrile |
| 90 | 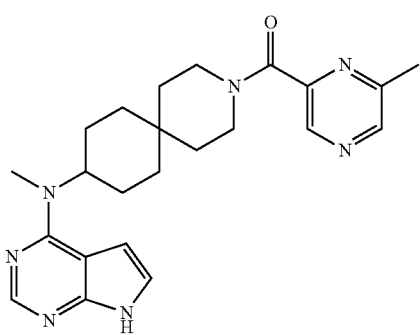 [SMILES: Cc1cncc(C(=O)N2CCC3(CCC(N(C)c4ncnc5[nH]ccc45)CC3)CC2)n1] | 419.2/420.2 | (6-Methyl-pyrazin-2-yl)-{9-[methyl-(7H-pyrrolo[2,3-d]pyrimidin-4-yl)-amino]-3-aza-spiro[5.5]undec-3-yl}-methanone |

| Entry | Structure | MS (calcd) [M + H]+/ MS (found) | Name |
|---|---|---|---|
| 91 | 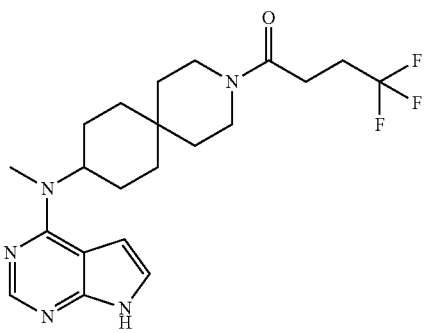 [SMILES: CN(c1ncnc2[nH]ccc12)C1CCC2(CC1)CCN(C(=O)CCC(F)(F)F)CC2] | 423.2/424.2 | 4,4,4-Trifluoro-1-{9-[methyl-(7H-pyrrolo[2,3-d]pyrimidin-4-yl)-amino]-3-aza-spiro[5.5]undec-3-yl}-butan-1-one |
| 92 | 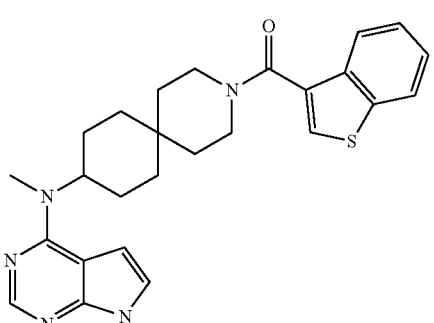 | 459.2/459.2 | Benzo[b]thiophen-3-yl-{9-[methyl-(7H-pyrrolo[2,3-d]pyrimidin-4-yl)-amino]-3-aza-spiro[5.5]undec-3-yl}-methanone |
| 93 | 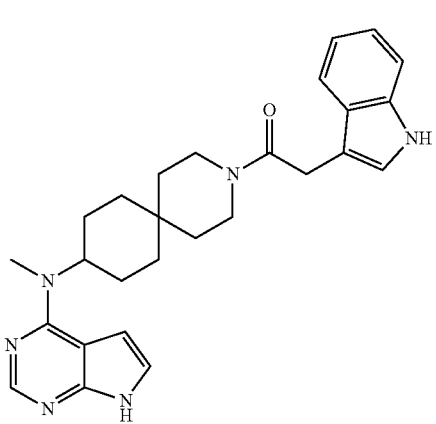 [SMILES: CN(c1ncnc2[nH]ccc12)C1CCC2(CC1)CCN(C(=O)Cc1c[nH]c3ccccc13)CC2] | 456.2/457.2 | 2-(1H-Indol-3-yl)-1-{9-[methyl-(7H-pyrrolo[2,3-d]pyrimidin-4-yl)-amino]-3-aza-spiro[5.5]undec-3-yl}-ethanone |
| 94 | 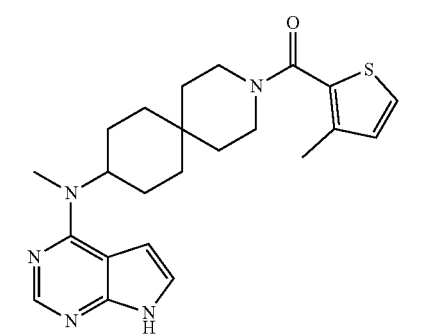 [SMILES: Cc1ccsc1C(=O)N1CCC2(CCC(N(C)c3ncnc4[nH]ccc34)CC2)CC1] | 423.2/424.2 | {9-[Methyl-(7H-pyrrolo[2,3-d]pyrimidin-4-yl)-amino]-3-aza-spiro[5.5]undec-3-yl}-(3-methyl-thiophen-2-yl)-methanone |

-continued

| Entry | Structure | MS (cald) [M + H]+/ MS (found) | Name |
|---|---|---|---|
| 95 | 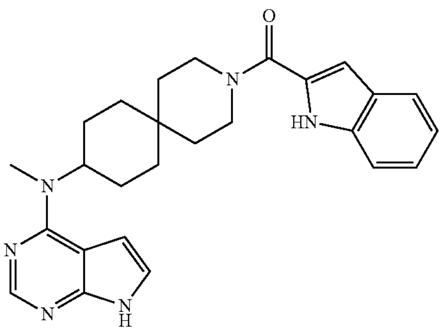 [SMILES: CN(c1ncnc2[nH]ccc12)C1CCC2(CC1)CCN(C(=O)c1cc3ccccc3[nH]1)CC2] | 442.2/443.2 | (1H-Indol-2-yl)-{9-[methyl-(7H-pyrrolo[2,3-d]pyrimidin-4-yl)-amino]-3-aza-spiro[5.5]undec-3-yl}-methanone |
| 96 | 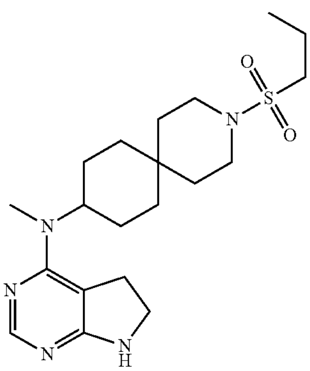 [SMILES: CCCS(=O)(=O)N1CCC2(CCC(N(C)c3ncnc4c3CCN4)CC2)CC1] | 407.2/408.2 | (6,7-Dihydro-5H-pyrrolo[2,3-d]pyrimidin-4-yl)-methyl-[3-(propane-1-sulfonyl)-3-aza-spiro[5.5]undec-9-yl]-amine |
| 97 | 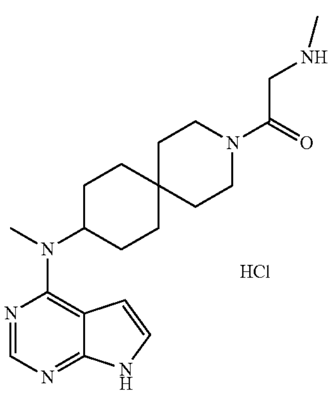 [SMILES: CNCC(=O)N1CCC2(CCC(N(C)c3ncnc4[nH]ccc34)CC2)CC1 ; Cl] | 370.2/371.2 | 2-Methylamino-1-{9-[methyl-(7H-pyrrolo[2,3-d]pyrimidin-4-yl)-amino]-3-aza-spiro[5.5]undec-3-yl}-ethanone HCl salt |
| 98 | 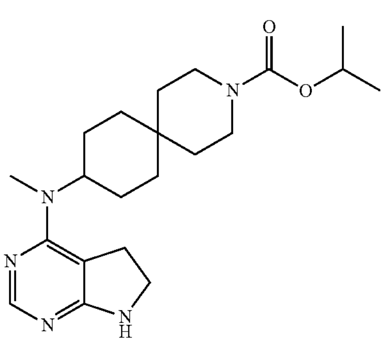 [SMILES: CC(C)OC(=O)N1CCC2(CCC(N(C)c3ncnc4c3CCN4)CC2)CC1] | 387.2/388.2 | 9-[(6,7-Dihydro-5H-pyrrolo[2,3-d]pyrimidin-4-yl)-methyl-amino]-3-aza-spiro[5.5]undecane-3-carboxylic acid isopropyl ester |

-continued

| Entry | Structure | MS (cald) [M + H]+/ MS (found) | Name |
|---|---|---|---|
| 99 | 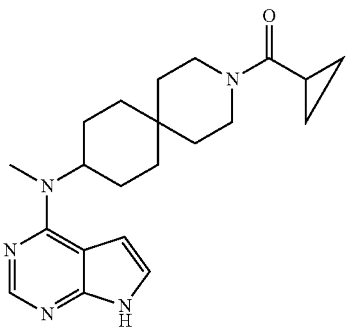 [SMILES: CN(c1ncnc2[nH]ccc12)C1CCC2(CC1)CCN(C(=O)C1CC1)CC2] | 367.2/368.2 | Cyclopropyl-{9-[methyl-(7H-pyrrolo[2,3-d]pyrimidin-4-yl)-amino]-3-aza-spiro[5.5]undec-3-yl}-methanone |
| 100 | 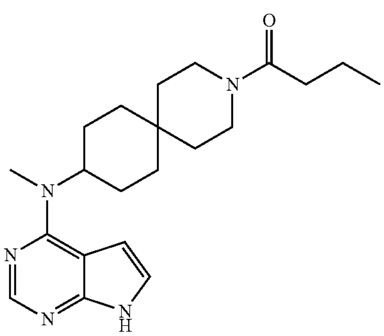 [SMILES: CCCC(=O)N1CCC2(CCC(N(C)c3ncnc4[nH]ccc34)CC2)CC1] | 369.2/370.2 | 1-{9-[Methyl-(7H-pyrrolo[2,3-d]pyrimidin-4-yl)-amino]-3-aza-spiro[5.5]undec-3-yl}-butan-1-one |
| 101 | 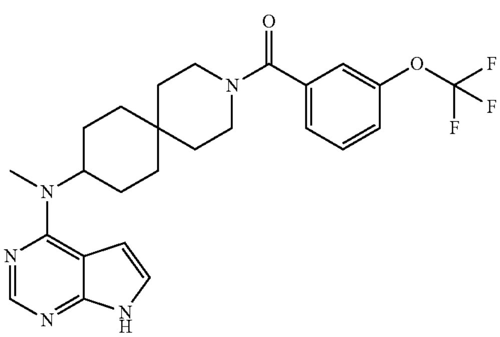 [SMILES: CN(c1ncnc2[nH]ccc12)C1CCC2(CC1)CCN(C(=O)c1cccc(OC(F)(F)F)c1)CC2] | 487.2/488.2 | {9-[Methyl-(7H-pyrrolo[2,3-d]pyrimidin-4-yl)-amino]-3-aza-spiro[5.5]undec-3-yl}-(3-trifluoromethoxy-phenyl)-methanone |
| 102 | 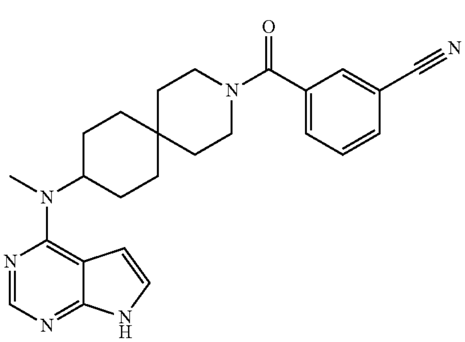 [SMILES: CN(c1ncnc2[nH]ccc12)C1CCC2(CC1)CCN(C(=O)c1cccc(C#N)c1)CC2] | 428.2/429.2 | 3-{9-[Methyl-(7H-pyrrolo[2,3-d]pyrimidin-4-yl)-amino]-3-aza-spiro[5.5]undecane-3-carbonyl}-benzonitrile |

-continued

| Entry | Structure | MS (cald) [M + H]+/ MS (found) | Name |
|---|---|---|---|
| 103 | 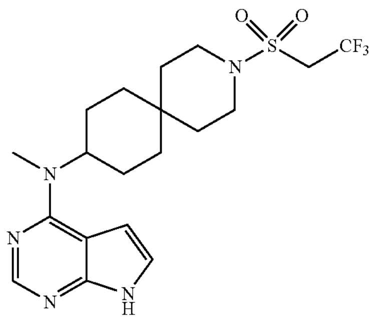 [SMILES: CN(c1ncnc2[nH]ccc12)C1CCC2(CC1)CCN(S(=O)(=O)CC(F)(F)F)CC2] | 445.1/446.1 | Methyl-(7H-pyrrolo[2,3-d]pyrimidin-4-yl)-[3-(2,2,2-trifluoro-ethanesulfonyl)-3-aza-spiro[5.5]undec-9-yl]-amine |
| 104 | 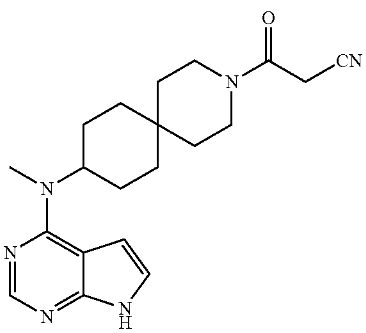 | 366.2/367.2 | 3-{9-[Methyl-(7H-pyrrolo[2,3-d]pyrimidin-4-yl)-amino]-3-aza-spiro[5.5]undec-3-yl}-3-oxo-propionitrile |
| 105 | 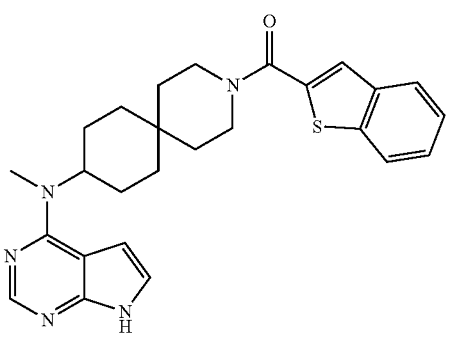 [SMILES: CN(c1ncnc2[nH]ccc12)C1CCC2(CC1)CCN(C(=O)c1cc3ccccc3s1)CC2] | 459.2/460.2 | Benzo[b]thiophen-2-yl-{9-[methyl-(7H-pyrrolo[2,3-d]pyrimidin-4-yl)-amino]-3-aza-spiro[5.5]undec-3-yl}-methanone |
| 106 | 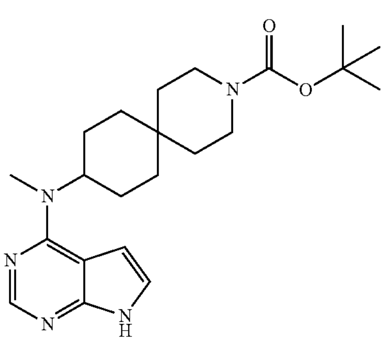 [SMILES: CN(c1ncnc2[nH]ccc12)C1CCC2(CC1)CCN(C(=O)OC(C)(C)C)CC2] | 399.2/400.3, 401.3 | tert-butyl 9-(methyl(7H-pyrrolo[2,3-d]pyrimidin-4-yl)amino)-3-azaspiro[5.5]undecane-3-carboxylate |

-continued

| Entry | Structure | MS (cald) [M + H]+/ MS (found) | Name |
|---|---|---|---|
| 107 | 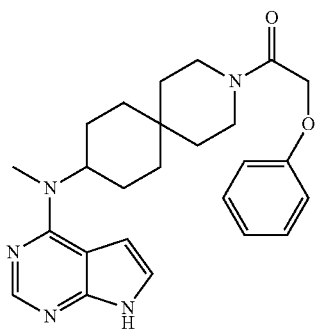 [SMILES: CN(c1ncnc2[nH]ccc12)C1CCC2(CC1)CCN(C(=O)COc1ccccc1)CC2] | 433.2/434.3 | 1-(9-(methyl(7H-pyrrolo[2,3-d]pyrimidin-4-yl)amino)-3-azaspiro[5.5]undecan-3-yl)-2-phenoxyethan-1-one |
| 108 | 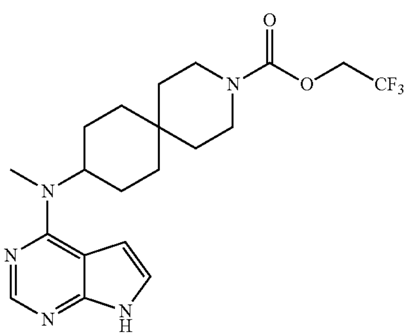 [SMILES: CN(c1ncnc2[nH]ccc12)C1CCC2(CC1)CCN(C(=O)OCC(F)(F)F)CC2] | 425.2/426.3 | 2,2,2-trifluoroethyl 9-(methyl(7H-pyrrolo[2,3-d]pyrimidin-4-yl)amino)-3-azaspiro[5.5]undecane-3-carboxylate |
| 109 | 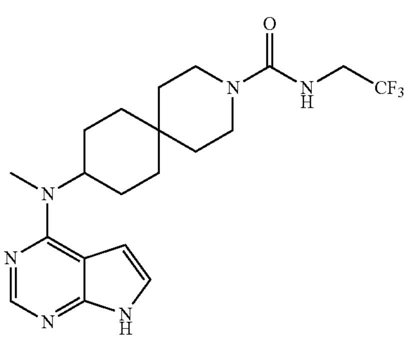 [SMILES: CN(c1ncnc2[nH]ccc12)C1CCC2(CC1)CCN(C(=O)NCC(F)(F)F)CC2] | 424.2/425.2 | 9-(methyl(7H-pyrrolo[2,3-d]pyrimidin-4-yl)amino)-N-(2,2,2-trifluoroethyl)-3-azaspiro[5.5]undecane-3-carboxamide |
| 110 | 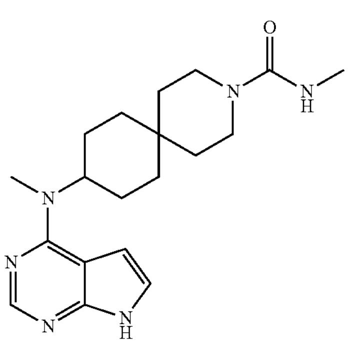 [SMILES: CNC(=O)N1CCC2(CCC(N(C)c3ncnc4[nH]ccc34)CC2)CC1] | 356.2/357.3 | N-methyl-9-(methyl(7H-pyrrolo[2,3-d]pyrimidin-4-yl)amino)-3-azaspiro[5.5]undecane-3-carboxamide |

| Entry | Structure | MS (cald) [M + H]⁺/ MS (found) | Name |
| --- | --- | --- | --- |
| 111 | 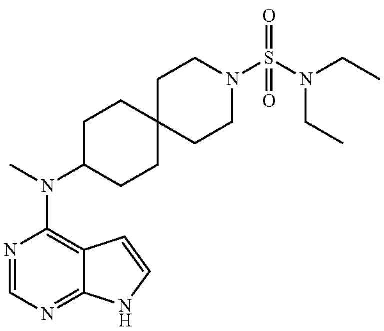 [SMILES: CCN(CC)S(=O)(=O)N1CCC2(CCC(N(C)c3ncnc4[nH]ccc34)CC2)CC1] | 434.2/435.3 | N,N-diethyl-9-(methyl(7H-pyrrolo[2,3-d]pyrimidin-4-yl)amino)-3-azaspiro[5.5]undecane-3-sulfonamide |
| 112 | 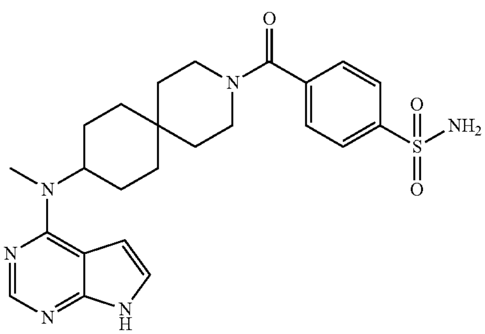 [SMILES: CN(c1ncnc2[nH]ccc12)C1CCC2(CC1)CCN(C(=O)c1ccc(S(N)(=O)=O)cc1)CC2] | 482.2/483.2 | 4-(9-(methyl(7H-pyrrolo[2,3-d]pyrimidin-4-yl)amino)-3-azaspiro[5.5]undecane-3-carbonyl)benzene-sulfonamide |
| 113 | 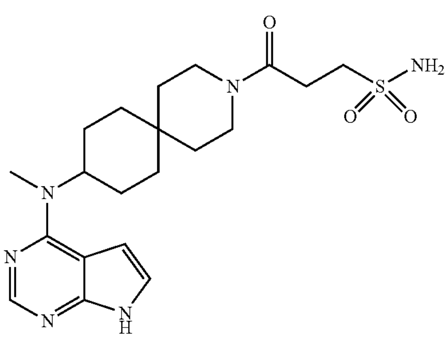 [SMILES: CN(c1ncnc2[nH]ccc12)C1CCC2(CC1)CCN(C(=O)CCS(N)(=O)=O)CC2] | 434.2/435.2, 436.2 | 3-(9-(methyl(7H-pyrrolo[2,3-d]pyrimidin-4-yl)amino)-3-azaspiro[5.5]undecan-3-yl)-3-oxopropane-1-sulfonamide |
| 114 | 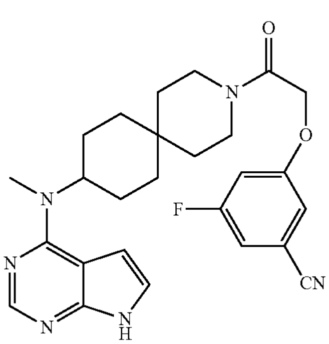 [SMILES: CN(c1ncnc2[nH]ccc12)C1CCC2(CC1)CCN(C(=O)COc1cc(F)cc(C#N)c1)CC2] | 476.2/477.2, 478.3 | 3-fluoro-5-(2-(9-(methyl(7H-pyrrolo[2,3-d]pyrimidin-4-yl)amino)-3-azaspiro[5.5]undecan-3-yl)-2-oxoethoxy)benzonitrile |

| Entry | Structure | MS (calcd) [M + H]+/ MS (found) | Name |
|---|---|---|---|
| 115 | 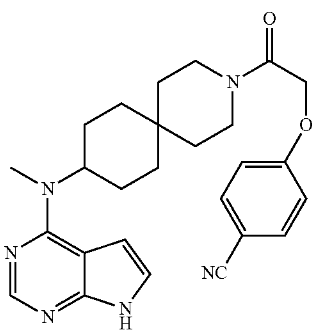 [SMILES: CN(c1ncnc2[nH]ccc12)C1CCC2(CC1)CCN(C(=O)COc1ccc(C#N)cc1)CC2] | 458.2/459.3, 460.3 | 4-(2-(9-(methyl(7H-pyrrolo[2,3-d]pyrimidin-4-yl)amino)-3-azaspiro[5.5]undecan-3-yl)-2-oxoethoxy)benzonitrile |
| 116 | 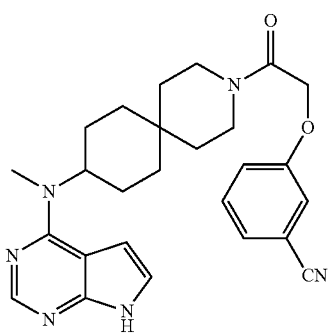 [SMILES: CN(c1ncnc2[nH]ccc12)C1CCC2(CC1)CCN(C(=O)COc1cccc(C#N)c1)CC2] | 458.2/459.3 | 3-(2-(9-(methyl(7H-pyrrolo[2,3-d]pyrimidin-4-yl)amino)-3-azaspiro[5.5]undecan-3-yl)-2-oxoethoxy)benzonitrile |
| 117 | 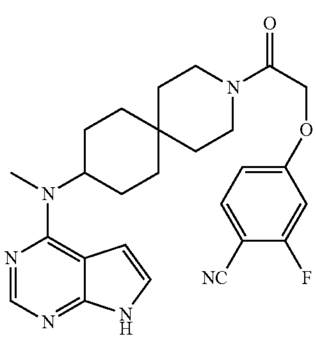 [SMILES: CN(c1ncnc2[nH]ccc12)C1CCC2(CC1)CCN(C(=O)COc1ccc(C#N)c(F)c1)CC2] | 476.2/477.3 | 2-fluoro-4-(2-(9-(methyl(7H-pyrrolo[2,3-d]pyrimidin-4-yl)amino)-3-azaspiro[5.5]undecan-3-yl)-2-oxoethoxy)benzonitrile |
| 118 | 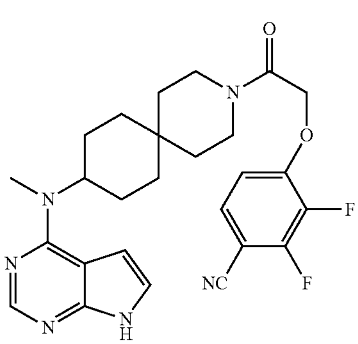 [SMILES: CN(c1ncnc2[nH]ccc12)C1CCC2(CC1)CCN(C(=O)COc1ccc(C#N)c(F)c1F)CC2] | 494.2/495.3, 496.3 | 2,3-difluoro-4-(2-(9-(methyl(7H-pyrrolo[2,3-d]pyrimidin-4-yl)amino)-3-azaspiro[5.5]undecan-3-yl)-2-oxoethoxy)benzonitrile |

-continued

| Entry | Structure | MS (cald) [M + H]+/ MS (found) | Name |
|---|---|---|---|
| 119 | 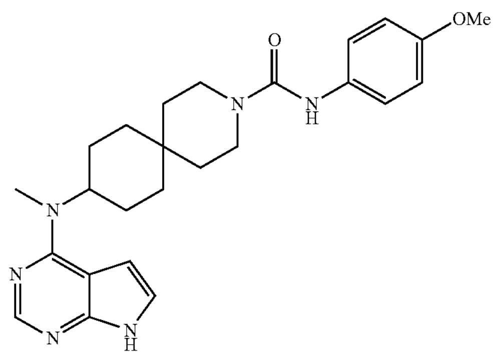 [SMILES: COc1ccc(NC(=O)N2CCC3(CCC(N(C)c4ncnc5[nH]ccc45)CC3)CC2)cc1] | 448.2/449.3, 450.3 | N-(4-methoxyphenyl)-9-(methyl(7H-pyrrolo[2,3-d]pyrimidin-4-yl)amino)-3-azaspiro[5.5]undecane-3-carboxamide |
| 120 | 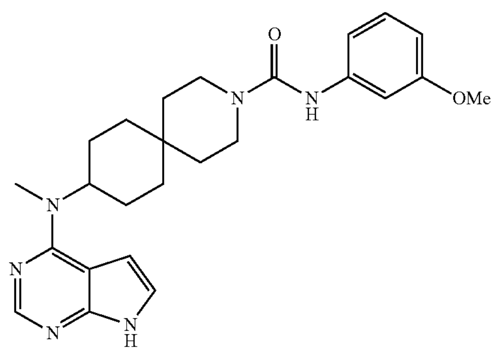 [SMILES: COc1cccc(NC(=O)N2CCC3(CCC(N(C)c4ncnc5[nH]ccc45)CC3)CC2)c1] | 448.2/449.2, 450.3 | N-(3-methoxyphenyl)-9-(methyl(7H-pyrrolo[2,3-d]pyrimidin-4-yl)amino)-3-azaspiro[5.5]undecane-3-carboxamide |
| 121 | 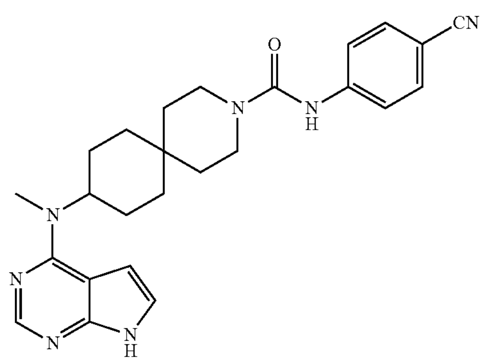 [SMILES: CN(c1ncnc2[nH]ccc12)C1CCC2(CC1)CCN(C(=O)Nc1ccc(C#N)cc1)CC2] | 443.2/444.3, 445.3 | N-(4-cyanophenyl)-9-(methyl(7H-pyrrolo[2,3-d]pyrimidin-4-yl)amino)-3-azaspiro[5.5]undecane-3-carboxamide |
| 122 | 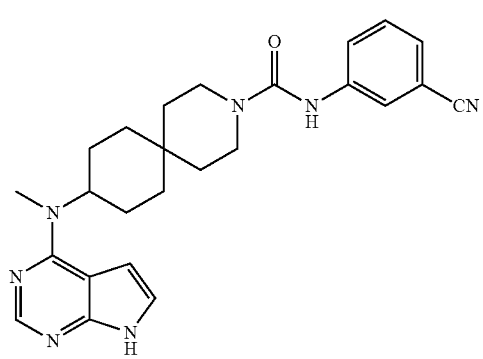 [SMILES: CN(c1ncnc2[nH]ccc12)C1CCC2(CC1)CCN(C(=O)Nc1cccc(C#N)c1)CC2] | 443.2/444.3, 445.3 | N-(3-cyanophenyl)-9-(methyl(7H-pyrrolo[2,3-d]pyrimidin-4-yl)amino)-3-azaspiro[5.5]undecane-3-carboxamide |

-continued

| Entry | Structure | MS (cald) [M + H]+/ MS (found) | Name |
|---|---|---|---|
| 123 | 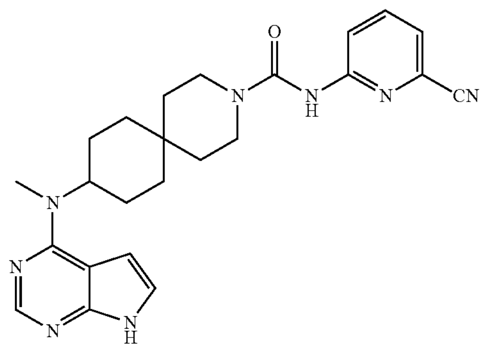 [SMILES: CN(c1ncnc2[nH]ccc12)C1CCC2(CC1)CCN(C(=O)Nc1cccc(C#N)n1)CC2] | 444.2/445.2, 446.2 | N-(6-cyanopyridin-2-yl)-9-(methyl(7H-pyrrolo[2,3-d]pyrimidin-4-yl)amino)-3-azaspiro[5.5]undecane-3-carboxamide |
| 124 | 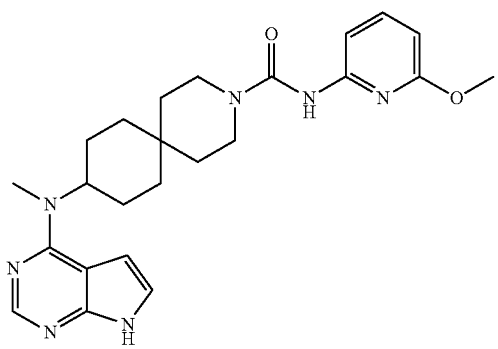 [SMILES: COc1cccc(NC(=O)N2CCC3(CCC(N(C)c4ncnc5[nH]ccc45)CC3)CC2)n1] | 449.2/450.3 | N-(6-methoxpyridin-2-yl)-9-(methyl(7H-pyrrolo[2,3-d]pyrimidin-4-yl)amino)-3-azaspiro[5.5]undecane-3-carboxamide |
| 125 | 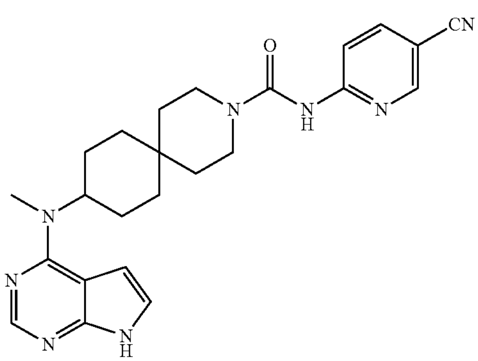 [SMILES: CN(c1ncnc2[nH]ccc12)C1CCC2(CC1)CCN(C(=O)Nc1ccc(C#N)cn1)CC2] | 444.2/445.2, 446.3 | N-(5-cyanopyridin-2-yl)-9-(methyl(7H-pyrrolo[2,3-d]pyrimidin-4-yl)amino)-3-azaspiro[5.5]undecane-3-carboxamide |
| 126 | 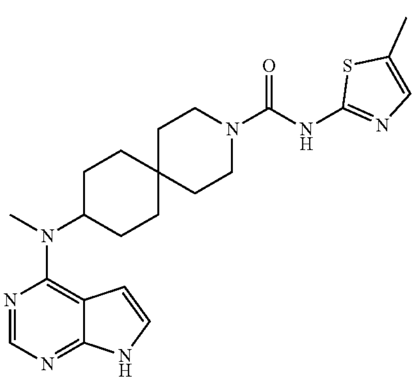 [SMILES: Cc1cnc(NC(=O)N2CCC3(CCC(N(C)c4ncnc5[nH]ccc45)CC3)CC2)s1] | 439.2/440.2 | 9-(methyl(7H-pyrrolo[2,3-d]pyrimidin-4-yl)amino)-N-(5-methylthiazol-2-yl)-3-azaspiro[5.5]undecane-3-carboxamide |

| Entry | Structure | MS (cald) [M + H]+/ MS (found) | Name |
|---|---|---|---|
| 127 | 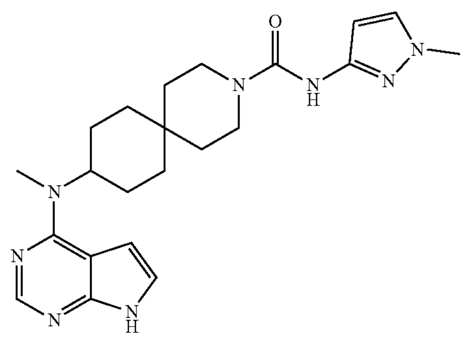 [SMILES: CN(c1ncnc2[nH]ccc12)C1CCC2(CC1)CCN(C(=O)Nc1ccn(C)n1)CC2] | 422.2/423.3 | 9-(methyl(7H-pyrrolo[2,3-d]pyrimidin-4-yl)amino)-N-(1-methyl-1H-pyrazol-3-yl)-3-azaspiro[5.5]undecane-3-carboxamide |
| 128 | 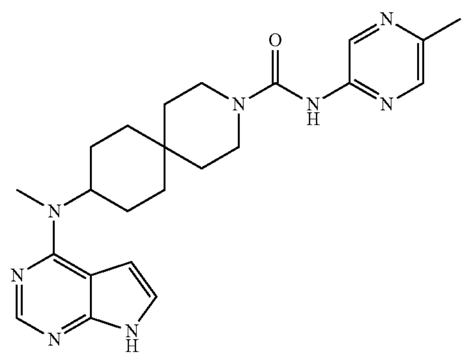 [SMILES: Cc1cnc(NC(=O)N2CCC3(CCC(N(C)c4ncnc5[nH]ccc45)CC3)CC2)cn1] | 434.2/435.3 | 9-(methyl(7H-pyrrolo[2,3-d]pyrimidin-4-yl)amino)-N-(5-methylpyrazin-2-yl)-3-azaspiro[5.5]undecane-3-carboxamide |
| 129 | 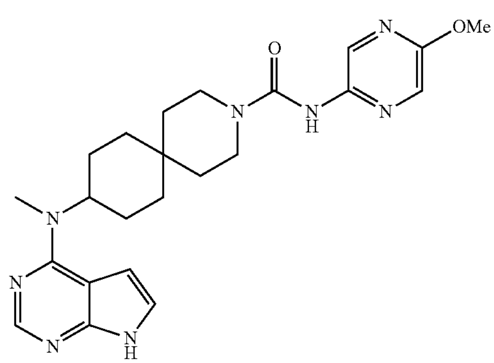 [SMILES: COc1cnc(NC(=O)N2CCC3(CCC(N(C)c4ncnc5[nH]ccc45)CC3)CC2)cn1] | 450.2/451.2, 452.3 | N-(5-methoxypyrazin-2-yl)-9-(methyl(7H-pyrrolo[2,3-d]pyrimidin-4-yl)amino)-3-azaspiro[5.5]undecane-3-carboxamide |
| 130 | 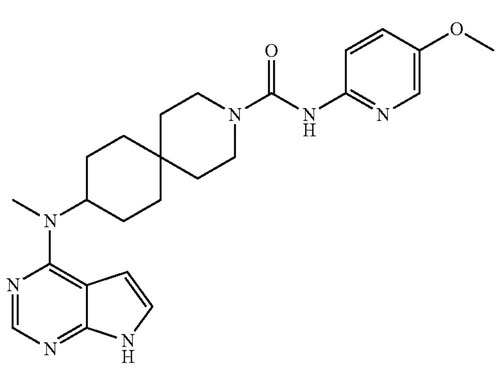 [SMILES: COc1ccc(NC(=O)N2CCC3(CCC(N(C)c4ncnc5[nH]ccc45)CC3)CC2)nc1] | 449.2/450.2, 451.3 | N-(5-methoxypyridin-2-yl)-9-(methyl(7H-pyrrolo[2,3-d]pyrimidin-4-yl)amino)-3-azaspiro[5.5]undecane-3-carboxamide |

-continued

| Entry | Structure | MS (cald) [M + H]+/ MS (found) | Name |
|---|---|---|---|
| 131 | 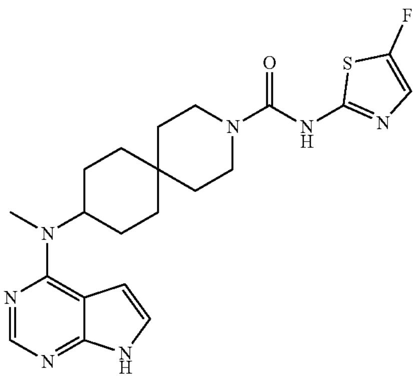 [SMILES: CN(c1ncnc2[nH]ccc12)C1CCC2(CC1)CCN(C(=O)Nc1ncc(F)s1)CC2] | 443.2/444.2 | N-(5-fluorothiazol-2-yl)-9-(methyl(7H-pyrrolo[2,3-d]pyrimidin-4-yl)amino)-3-azaspiro[5.5]undecane-3-carboxamide |
| 132 | 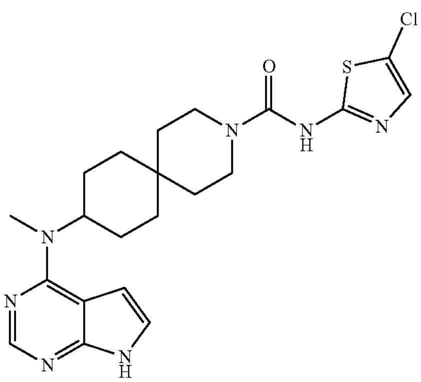 [SMILES: CN(c1ncnc2[nH]ccc12)C1CCC2(CC1)CCN(C(=O)Nc1ncc(Cl)s1)CC2] | 459.2/460.2, 461.2/463.2 | N-(5-chlorothiazol-2-yl)-9-(methyl(7H-pyrrolo[2,3-d]pyrimidin-4-yl)amino)-3-azaspiro[5.5]undecane-3-carboxamide |
| 133 | 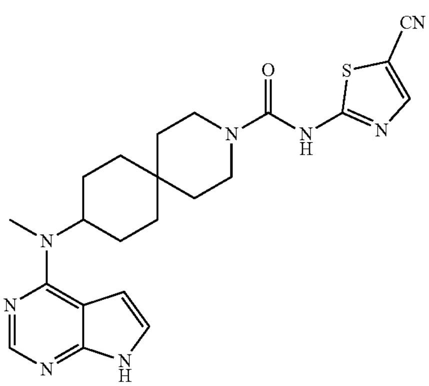 [SMILES: CN(c1ncnc2[nH]ccc12)C1CCC2(CC1)CCN(C(=O)Nc1ncc(C#N)s1)CC2] | 450.2/451.2, 452.2, 453.2 | N-(5-cyanothiazol-2-yl)-9-(methyl(7H-pyrrolo[2,3-d]pyrimidin-4-yl)amino)-3-azaspiro[5.5]undecane-3-carboxamide |
| 134 | 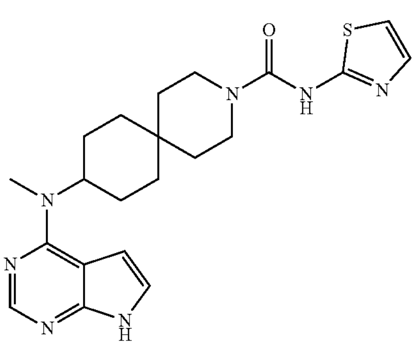 [SMILES: CN(c1ncnc2[nH]ccc12)C1CCC2(CC1)CCN(C(=O)Nc1nccs1)CC2] | 425.2/426.2, 427.2 | 9-(methyl(7H-pyrrolo[2,3-d]pyrimidin-4-yl)amino)-N-(thiazol-2-yl)-3-azaspiro[5.5]undecane-3-carboxamide |

-continued

| Entry | Structure | MS (cald) [M + H]+/ MS (found) | Name |
|---|---|---|---|
| 135 | 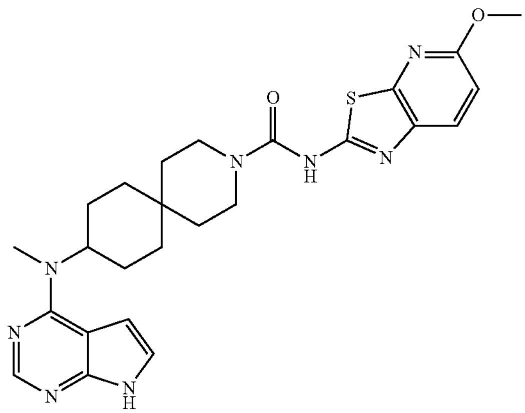 [SMILES: COc1ccc2nc(NC(=O)N3CCC4(CCC(N(C)c5ncnc6[nH]ccc56)CC4)CC3)sc2n1] | 506.2/506.2 | N-(5-methoxythiazolo[5,4-b]pyridin-2-yl)-9-(methyl(7H-pyrrolo[2,3-d]pyrimidin-4-yl)amino)-3-azaspiro[5.5]undecane-3-carboxamide |

JAK Kinase Assay 384-well plates in the left foot butoxy measured progress. The final assay volume was 25 µL, 250 nL 100× compounds, 10 µL enzyme mix and 15 µL substrate mix (fluoresceinated peptide and ATP) in assay buffer (20 mM HEPES (pH 7.5), 10 mM $MgCl_2$, 0.0100 TritonX-100, 0.0% Brij35, 0.5 mM EGTA and 2 mM DTT) prepared as test compound. By mixing the JAK1 with substrates and test compounds to start the reaction. There action mixture was incubated for 120 minutes at room temperature, then added 30 µL stop buffer for each sample to terminate the reaction with 50 mM EDTA. After termination of the kinase reaction, the proportion of phosphorylated product was determined as a fraction of total peptide substrate using Caliper EZ Reader II. Inhibition data were calculated by comparison with 100% of the reaction mixture without enzyme inhibition and vehicle-only reaction mixture billion % inhibition compared. The final concentration of reagents in the assays is: ATP, 76.5 µM; JAK1 fluorescent peptide (5-FAM-EEP-LYWSFPAKKK-CONH2), 3 µM; JAK1, 10 nM, and DMSO, 1%. Dose response curve were generated to determine the concentration required for $IC_{50}$ of JAK activity.

JAK2 Assay 384-well plates in the left foot butoxy measured progress. The final assay volume was 25 µL, 250 nL 100× compounds, 10 µL enzyme mix and 15 µL substrate mix (fluoresceinated peptide and ATP) in assay buffer (50 mM HEPES (pH 7.5), 10 mM $MgCl_2$, 0.01% TritonX-100, 0.01% Brij35, 0.5 mM EGTA and 2 mM DTT) prepared as test compound By mixing the JAK2 with substrates and test compounds to start the reaction. The reaction mixture was incubated for 15 minutes at room temperature, then added 30 µL stop buffer for each sample to terminate the reaction with 50 mM EDTA. After termination of the kinase reaction, the proportion of phosphorylated product was determined as a fraction of total peptide substrate using Caliper EZ Reader 1 Inhibition data were calculated by comparison with 100% of the reaction mixture without enzyme inhibition and vehicle-only reaction mixture billion % inhibition compared. The final concentration of reagents in the assays is: ATP, 11.4 µM; JAK2 fluorescent peptide (5-FAM-EEP-LYWSFPAKKK-CONH2), 3 µM; JAK2, 0.25 nM; and DMSO, 1%. Dose response curve were generated to determine the concentration required for $IC_{50}$ of JAK2 activity.

JAK3 Assay 384-well plates in the left foot butoxy measured progress. The final assay volume was 25 µL, 250 nL 100× compounds, 10 µL enzyme mix and 15 µL substrate mix (fluoresceinated peptide and ATP) in assay buffer (50 mM HEPES (pH 7.5), 10 mM $MgCl_2$, 0.01% TritonX-100, 0.01% Brij35, 0.5 mM EGTA and 2 mM DTT) prepared as test compound. By mixing the JAK3 with substrates and test compounds to start the reaction. The reaction mixture was incubated for 30 minutes at room temperature, then added 30 µL stop buffer for each sample to terminate the reaction with 50 mM EDTA. After termination of the kinase reaction, the proportion of phosphorylated product was determined as a fraction of total peptide substrate using Caliper EZ Reader II. Inhibition data were calculated by comparison with 100% of the reaction mixture without enzyme inhibition and vehicle-only reaction mixture billion % inhibition compared. The final concentration of reagents in the assays is: ATP, 3.5 µM; JAK3 fluorescent peptide (5-FAM-EEPLYWSFPAKKK-CONH2), 3 µM; JAK3, 0.5 nM; and DMSO, 1%. Dose response curve were generated to determine the concentration required for $IC_{50}$ of JAK3 activity.

TYK2 Assay 384-well plates in the left foot butoxy measured progress. The final assay volume was 25 µL, 250 nL 100× compounds, 10 µL enzyme mix and 15 µL substrate mix (fluoresceinated peptide and ATP) in assay buffer (50 mM HEPES (pH 7.5), 10 mM $MgCl_2$, 0.01% TritonX-100, 0.01% Brij35, 0.5 mM EGTA and 2 mM DTT) prepared as test compound. B mixing the TYK2 with substrates and test compounds to start the reaction. The reaction mixture was incubated for 10 minutes at room temperature, then added 30 µL stop buffer for each sample to terminate the reaction with 50 mM EDTA. After termination of the kinase reaction, the proportion of phosphorylated product was determined as a fraction of total peptide substrate using Caliper EZ Reader 1. Inhibition data were calculated by comparison with 100% of the reaction mixture without enzyme inhibition and vehicle-only reaction mixture billion % inhibition compared. The final concentration of reagents in the assays is: ATP, 35.4 µM; TYK2 fluorescent peptide (5-FAM-KKKKEEIYFFF-CONH2), 3 µM; TYK2, 10 nM; and DMSO, 1% Dose response curve were generated to determine the concentration required for $IC_{50}$ of TYK2 activity.

Example 136

The following Table shows the activity of selected compounds of this invention in the JAK inhibition assay. The compound numbers correspond to the compound numbers in previous Tables. Compounds having an activity designated as "A" provided an IC $50 \leq 10$ nM; Compounds having an activity designated as "B" provided an $IC_{50}$ 10-100 nM; Compounds having an activity designated as "C" provided an $IC_{50}$ 100-1000 nM; Compounds having an activity designated as "D" provided an $IC_{50}$ 1000-10000 nM; Compounds having an activity designated as "E" provided an $IC_{50} \geq 10000$ nM.

| | JAK | | | |
|---|---|---|---|---|
| Comp. # | JAK1 inhibition | JAK2 inhibition | JAK3 inhibition | TYK2 inhibition |
| 1 | B | D | E | E |
| 2 | C | C | D | |
| 3 | C | C | D | |
| 4 | C | C | E | |
| 5 | C | C | D | |
| 6 | C | C | E | |
| 7 | C | D | D | |
| 8 | C | D | D | |
| 9 | B | C | D | |
| 10 | B | C | D | |
| 11 | B | C | D | |
| 12 | B | C | D | |
| 13 | C | D | D | |
| 14 | B | C | E | E |
| 15 | C | D | D | |
| 16 | C | D | D | |
| 17 | C | D | E | |
| 18 | C | D | E | |
| 19 | B | C | D | |
| 20 | B | D | D | |
| 21 | B | C | D | |
| 22 | B | D | D | |
| 23 | C | D | D | |
| 24 | B | D | E | E |
| 25 | B | D | E | E |
| 26 | A | C | E | D |
| 27 | B | D | E | E |
| 28 | B | C | E | E |
| 29 | C | D | E | |
| 30 | B | C | E | D |
| 31 | C | D | E | E |
| 32 | B | D | E | E |
| 33 | C | D | E | E |
| 34 | B | D | D | |
| 35 | B | D | D | |
| 36 | B | D | D | |
| 37 | B | C | D | |
| 38 | B | C | D | |
| 39 | B | C | D | |
| 40 | A | C | D | |
| 41 | A | B | D | |
| 42 | A | B | D | |
| 43 | A | C | D | |
| 44 | C | D | E | |
| 45 | D | D | E | |
| 46 | A | C | E | |
| 47 | A | C | D | |
| 48 | B | D | D | |
| 49 | D | D | E | |
| 50 | C | E | E | |
| 51 | B | | | |
| 52 | B | | | |
| 53 | A | C | D | D |
| 54 | B | | | |
| 55 | B | | | |
| 56 | A | | | |
| 57 | A | | | |
| 58 | A | | | |
| 59 | B | | | |
| 60 | A | | | |
| 61 | A | | | |
| 62 | B | | | |
| 63 | A | | | |
| 64 | A | | | |
| 65 | B | | | |
| 66 | A | | | |
| 67 | A | | | |
| 68 | C | D | D | |
| 69 | C | D | E | |
| 70 | A | | | |
| 71 | A | | | |
| 72 | B | | | |
| 73 | A | C | C | |
| 74 | A | | | |
| 75 | B | B | C | |
| 76 | C | C | D | |
| 77 | B | B | C | |
| 78 | C | C | D | |
| 79 | C | C | C | |
| 80 | C | C | C | |
| 81 | C | C | C | |
| 82 | C | D | D | |
| 83 | C | C | D | |
| 84 | C | C | D | |
| 85 | B | C | C | |
| 86 | C | C | D | |
| 87 | C | C | C | |
| 88 | C | C | D | |
| 89 | C | C | D | |
| 90 | C | C | D | |
| 91 | C | C | D | |
| 92 | C | C | C | |
| 93 | C | C | C | |
| 94 | C | C | D | |
| 95 | C | C | C | |
| 96 | C | C | D | |
| 97 | C | C | D | |
| 98 | B | C | D | |
| 99 | B | C | D | |
| 100 | C | C | D | |
| 101 | C | C | D | |
| 102 | C | C | C | |
| 103 | B | C | C | |
| 104 | D | D | D | |
| 105 | C | C | D | |
| 106 | D | | | |
| 107 | A | | | |
| 108 | C | | | |
| 109 | B | | | |
| 110 | B | | | |
| 111 | E | | | |
| 112 | B | | | |
| 113 | D | | | |
| 114 | A | | | |
| 115 | A | | | |
| 116 | B | | | |
| 117 | B | | | |
| 118 | B | | | |
| 119 | B | | | |
| 120 | A | | | |
| 121 | B | | | |
| 122 | A | | | |
| 123 | A | | | |
| 124 | B | | | |
| 125 | D | | | |
| 126 | C | | | |
| 127 | C | | | |
| 128 | D | | | |
| 129 | B | | | |
| 130 | B | | | |
| 131 | B | | | |
| 132 | C | | | |

-continued

| | JAK | | | |
|---|---|---|---|---|
| Comp. # | JAK1 inhibition | JAK2 inhibition | JAK3 inhibition | TYK2 inhibition |
| 133 | A | | | |
| 134 | A | | | |
| 135 | N/A | | | |

What is claimed is:

1. A compound of general formula (I), or a pharmaceutically acceptable salt, prodrug, hydrate, or solvate thereof,

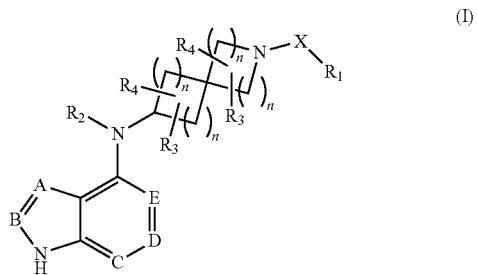

(I)

wherein:

n is an integer of 0-5;

A, B, C, and D are independently N or C—$R_5$, and E is N;

$R_5$ is selected from the group consisting of hydrogen, deuterium, halogen, hydroxy, amino, nitro, CN, —$SO_2NH_2$, —$SONH_2$, —NHOH, —$CONH_2$, —$OR_{5a}$, —$N(R_{5a})_2$, —$SR_{5a}$, alkyl, cycloalkyl, alkoxy, alkylthio, alkylsulfonyl, heterocyclyl, aryl, heteroaryl, —$CF_3$, —$CF_2H$, —$OCF_3$, —$OCF_2H$, $C_{1-6}$ alkyl substituted with one to five fluorines, $C_{3-6}$ cycloalkyl substituted with one to five fluorines, $C_{1-4}$ alkoxy substituted with one to five fluorines, $C_{1-4}$ alkylthio substituted with one to five fluorines, $C_{1-4}$ alkylsulfonyl substituted with one to five fluorines, carboxy, $C_{1-4}$ alkyloxycarbonyl, and $C_{1-4}$ alkylcarbonyl;

$R_{5a}$ is selected from the group consisting of alkyl, cycloalkyl, alkoxy, alkylthio, alkylsulfonyl, heterocyclyl, aryl, heteroaryl, —$CF_3$, —$CF_2H$, —$OCF_3$, —$OCF_2H$, $C_{1-6}$ alkyl substituted with one to five fluorines, $C_{3-6}$ cycloalkyl substituted with one to five fluorines, $C_{1-4}$ alkoxy substituted with one to five fluorines, $C_{1-4}$ alkylthio substituted with one to five fluorines, $C_{1-4}$ alkylsulfonyl substituted with one to five fluorines, carboxy, $C_{1-4}$ alkyloxycarbonyl, and $C_{1-4}$ alkylcarbonyl;

$R_2$, $R_3$, and $R_4$ independently at each occurrence are selected from the group consisting of hydrogen, alkyl, alkenyl, alkynyl, cycloalkyl, cycloalkenyl, cycloalkylalkyl, cycloalkylalkenyl, cycloalkylalkynyl, cycloalkenylalkyl, cycloalkenylalkenyl, cycloalkenylalkynyl, heterocyclyl, heterocyclylalkyl, heterocyclylalkenyl, heterocyclylalkynyl, aryl, arylalkyl, arylalkenyl, arylalkynyl, arylcycloalkyl, aryloxyalkyl, aryloxycycloalkyl, heteroaryl, heteroarylalkyl, heteroarylalkenyl, heteroarylalkynyl, heteroarylcycloalkyl, heteroaryloxyalkyl, and heteroaryloxycycloalkyl, any of which may be optionally substituted with one or more $R_{2a}$;

$R_{2a}$ is selected from the group consisting of halogen, cyano, hydroxy, oxo, —$NH_2$, —$SO_2NH_2$, —$SONH_2$, —$CONH_2$, alkyl, alkenyl, alkynyl, cycloalkyl, cycloalkeny, heterocyclyl, $R_{2b}$O-L-, $R_{2b}$S-L-, $(R_{2b})_2$N-L-,$R_{2b}$—C(=O)L-, $R_{2b}$—C(=O)-L-, $(R_{2b})_2$N—C(=O)-L-, $R_{2b}$—C(=O)N($R_{2b}$)-L-, $R_{2b}$O—C(=O)N($R_{2b}$)-L-, $(R_{2b})_2$NC(=O)N($R_{2b}$)-L-, $R_{2b}$—C(=O)O-L-, $R_{2b}$O—C(=O)O-L-, $(R_{2b})_2$N—C(=O)O-L-, $R_{2b}$O—S(=O)$_2$-L-, $(R_{2b})_2$ N—S(=O)$_2$-L-, $R_{2b}$—S(=O)$_2$N($R_{2b}$)-L-, $R_{2b}$—S(=O)$_2$N($R_{2b}$)-L-, $(R_{2b})_2$N—S(=O)$_2$N($R_{2b}$)-L-,$R_{2b}$ S(=O)$_2$O-L-, $R_{2b}$—S(=O)$_2$O-L-, $(R_{2b})$N—S(=O)$_2$O-L-, aryl-, aryloxy-, heteroaryl, and heteroaryloxy;

$R_{2b}$ independently at each occurrence is selected from the group consisting of alkyl, alkenyl, alkynyl, cycloalkyl, heterocyclyl, aryl, and heteroaryl;

$R_1$ is hydrogen, alkyl, heteroalkyl, aryl, aryloxy, heteroaryl, or heteroaryloxy, which may be optionally substituted with one or more $R_{1a}$, wherein any two $R_{1a}$ form, together with the ring atom(s) to which they are attached, a cycloalkyl or heterocycle, and two $R_{1a}$ are either attached to the same C atom or to two nonadjacent C atoms; $R_{1a}$ independently at each occurrence is selected from the group consisting of halogen, cyano, hydroxy, oxo, —$NH_2$, —$SO_2NH_2$, —$SONH_2$, —$CONH_2$, alkyl, alkenyl, alkynyl, alkenylalkyl, alkynylalkyl, cycloalkyl, cycloalkenyl, cycloalkylalkyl, cycloalkylalkenyl, heterocyclyl, $R_{1b}$O-L, $R_{1b}$S-L-, $(R_{1b})_2$N-L-, $R_{1b}$—C(=O)L-, $R_{1b}$—C(=O)-L-, $(R_{1b})_2$N—C(=O)-L-, $R_{1b}$—C(=O)N($R_{1b}$)-L-, $R_{1b}$O—C(=O)N($R_{1b}$)-L-, $(R_{1b})_2$NC(=O)N($R_{1b}$)-L-, $R_{1b}$—C(=O)O-L-, $R_{1b}$O—C(=O)O-L-, $(R_{1b})_2$N—C(=O)O-L-, $R_{1b}$O—S(=O)$_2$-L-, $(R_{1b})_2$N—S(=O)$_2$-L-, $R_{1b}$—S(=O)$_2$N($R_{1b}$)-L-, $R_{1b}$—S(=O)$_2$N($R_{1b}$)-L-, $(R_{1b})_2$N—S(=O)$_2$N($R_{1b}$)-L-, $R_{1b}$ S(=O)$_2$O-L-, $R_{1b}$—S(=O)$_2$O-L-, $(R_{1b})$N—S(=O)$_2$O-L-, aryl, aryloxy, heteroaryl, and heteroaryloxy;

$R_{1b}$ independently at each occurrence is selected from the group consisting of alkyl, alkenyl, alkynyl, cycloalkyl, heterocyclyl, aryl, and heteroaryl;

L is a covalent bond or L is independently at each occurrence selected from the group consisting of alkyl, cycloalkyl, alkylcycloalkyl and cycloalkyl; and X is a covalent bond or X is —C(=O)—, —S(=O)—, —S(=O)$_2$—, —C(=O)O—, —C(=O)NH—, —S(=O)NH—, —S(=O)$_2$NH—.

2. The compound of general formula (I) of claim 1, wherein $R_3$ and $R_4$ are both hydrogens.

3. The compound of general formula (I) of claim 1, wherein $R_5$ is hydrogen.

4. The compound of general formula (I) of claim 1, wherein $R_2$ is alkyl.

5. The compound of general formula (I) of claim 1, wherein X is —C(=O)—, —S(=O)—, —S(=O)$_2$—, —C(=O)O—, —C(=O)NH—, —S(=O)NH—, —S(=O)$_2$NH—.

6. The compound of general formula (I) of claim 1, wherein $R_1$ is

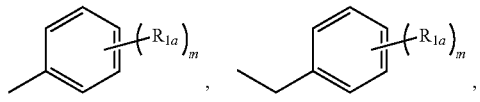

-continued

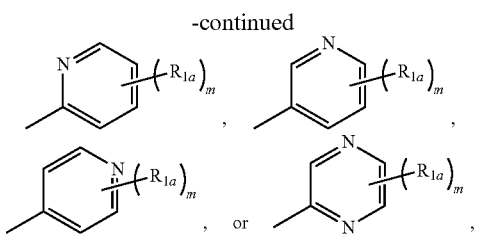

wherein m is an integer of 1-3; and Ria independently at each occurrence is selected from the group consisting of halogen, cyano, hydroxy, —NH₂, —SO₂NH₂, —SONH₂, —CONH₂, alkyl, alkenyl, alkynyl, alkenylalkyl, alkynylalkyl, cycloalkyl, cycloalkenyl, cycloalkylalkyl, cycloalkylalkenyl, heterocyclyl, aryl, aryloxy, heteroaryl, and heteroaryloxy.

7. The compound of general formula (I) of claim 1, wherein R₁ is

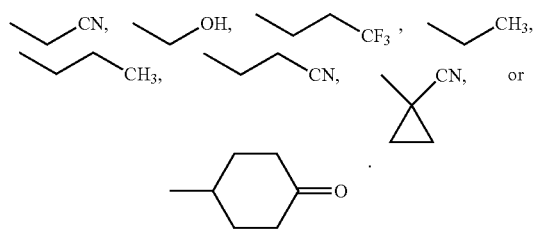

8. The compound of general formula (I) of claim 1, wherein R₁ is

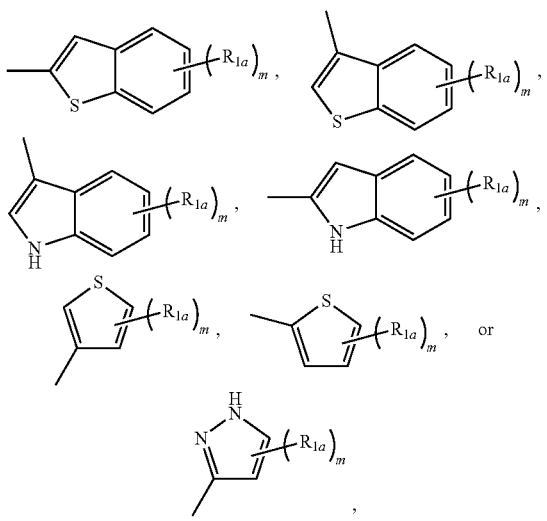

wherein m is an integer of 1-3; and Ria independently at each occurrence is selected from the group consisting of halogen, cyano, hydroxy, —NH₂, —SO₂NH₂, —SONH₂, —CONH₂, alkyl, alkenyl, alkynyl, alkenylalkyl-, alkynylalkyl, cycloalkyl, cycloalkenyl, cycloalkylalkyl, cycloalkylalkenyl, heterocyclyl, aryl-, aryloxy-, heteroaryl, and heteroaryloxy.

9. The compound of general formula (I) of claim 1, wherein A and B are CH, C is N, D is CH, and E is N.

10. The compound of general formula (I) of claim 1, wherein the compound is selected from the group consisting of 2-fluoro-4-(6-(methyl(7H-pyrrolo[2,3-d]pyrimidin-4-yl)amino)-2-azaspiro[3.3]heptane-2-carbonyl)benzonitrile; 3-(6-(methyl(7H-pyrrolo[2,3-d]pyrimidin-4-yl)amino)-2-azaspiro[3.3]heptan-2-yl)-3-oxopropanenitrile; 2-hydroxy-1-(6-(methyl(7H-pyrrolo[2,3-d]pyrimidin-4-yl)amino)-2-azaspiro[3.3]heptan-2-yl)ethanone; 1-(6-(methyl(7H-pyrrolo[2,3-d]pyrimidin-4-yl)amino)-2-azaspiro[3.3]heptan-2-yl)ethanone; 1-(6-(methyl(7H-pyrrolo[2,3-d]pyrimidin-4-yl)amino)-2-azaspiro[3.3]heptan-2-yl)propan-1-one; N-(2-(ethylsulfonyl)-2-azaspiro[3.3]heptan-6-yl)-N-methyl-7H-pyrrolo[2,3-d]pyrimidin-4-amine; methyl 6-(methyl(7H-pyrrolo[2,3-d]pyrimidin-4-yl)amino)-2-azaspiro[3.3]heptane-2-carboxylate; ethyl 6-(methyl(7H-pyrrolo[2,3-d]pyrimidin-4-yl)amino)-2-azaspiro[3.3]heptane-2-carboxylate; (6-(methyl(7H-pyrrolo[2,3-d]pyrimidin-4-yl)amino)-2-azaspiro[3.3]heptan-2-yl)(pyridin-3-yl)methanone; 4-(6-(methyl(7H-pyrrolo[2,3-d]pyrimidin-4-yl)amino)-2-azaspiro[3.3]heptan-2-yl)-4-oxobutanenitrile; 3-(6-(methyl(7H-pyrrolo[2,3-d]pyrimidin-4-yl)amino)-2-azaspiro[3.3]heptane-2-carbonyl)benzonitrile; 4-(6-(methyl(7H-pyrrolo[2,3-d]pyrimidin-4-yl)amino)-2-azaspiro[3.3]heptane-2-carbonyl)cyclohexanone; (6-(methyl(7H-pyrrolo[2,3-d]pyrimidin-4-yl)amino)-2-azaspiro[3.3]heptan-2-yl)(3-(trifluoromethyl)phenyl)methanone; 3-fluoro-4-(6-(methyl(7H-pyrrolo[2,3-d]pyrimidin-4-yl)amino)-2-azaspiro[3.3]heptane-2-carbonyl)benzonitrile; 4-(2-(6-(methyl(7H-pyrrolo[2,3-d]pyrimidin-4-yl)amino)-2-azaspiro[3.3]heptan-2-yl)-2-oxoethyl)benzonitrile; (6-(methyl(7H-pyrrolo[2,3-d]pyrimidin-4-yl)amino)-2-azaspiro[3.3]heptan-2-yl)(3-(trifluoromethoxy)phenyl)methanone; (6-(methyl(7H-pyrrolo[2,3-d]pyrimidin-4-yl)amino)-2-azaspiro[3.3]heptan-2-yl)(pyrazin-2-yl)methanone; 1-(6-(methyl(7H-pyrrolo[2,3-d]pyrimidin-4-yl)amino)-2-azaspiro[3.3]heptane-2-carbonyl)cyclopropanecarbonitrile; benzo[b]thiophen-2-yl(6-(methyl(7H-pyrrolo[2,3-d]pyrimidin-4-yl)amino)-2-azaspiro[3.3]heptan-2-yl)methanone; 4,4,4-trifluoro-1-(6-(methyl(7H-pyrrolo[2,3-d]pyrimidin-4-yl)amino)-2-azaspiro[3.3]heptan-2-yl)butan-1-one; benzo[b]thiophen-3-yl(6-(methyl(7H-pyrrolo[2,3-d]pyrimidin-4-yl)amino)-2-azaspiro[3.3]heptan-2-yl)methanone; 2-(1H-indol-3-yl)-1-(6-(methyl(7H-pyrrolo[2,3-d]pyrimidin-4-yl)amino)-2-azaspiro[3.3]heptan-2-yl)ethenone; (4-methoxyphenyl)(6-(methyl(7H-pyrrolo[2,3-d]pyrimidin-4-yl)amino)-2-azaspiro[3.3]heptan-2-yl)methanone; (4-chlorophenyl)(6-(methyl(7H-pyrrolo[2,3-d]pyrimidin-4-yl)amino)-2-azaspiro[3.3]heptan-2-yl)methanone; (4-ethynylphenyl)(6-(methyl(7H-pyrrolo[2,3-d]pyrimidin-4-yl)amino)-2-azaspiro[3.3]heptan-2-yl)methanone; (4-fluorophenyl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(3-methylthiophen-2-yl)methanone; (6-(methyl(7H-pyrrolo[2,3-d]pyrimidin-4-yl)amino)-2-azaspiro[3.3]heptan-2-yl)(6-methylpyrazin-2-yl)methanone; (1H-indol-2-yl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(4-(trifluoromethyl)phenyl)methanone; (5-chloropyridin-2-yl)(6-(methyl(7H-pyrrolo[2,3-d]pyrimidin-4-yl)amino)-2-azaspiro[3.3]heptan-2-yl)methanone; N-(3-chlorophenyl)-6-(methyl(7H-pyrrolo[2,3-d]pyrimidin-4-yl)amino)-2-azaspiro[3.3]heptane-2-carboxamide; 2-methyl-4-(6-(methyl(7H-pyrrolo[2,3-d]pyrimidin-4-yl)amino)-2-azaspiro[3.3]heptane-2-carbonyl)benzonitrile; 5-(6-(methyl(7H-pyrrolo[2,3-d]pyrimidin-4-yl)amino)-2-azaspiro[3.3]heptane-2-carbonyl)

picolinonitrile; 2-chloro-4-(6-(methyl(7H-pyrrolo[2,3-d]pyrimidin-4-yl)amino)-2-azaspiro[3.3]heptane-2-carbonyl)benzonitrile; 3-chloro-4-(6-(methyl(7H-pyrrolo[2,3-d]pyrimidin-4-yl)amino)-2-azaspiro[3.3]heptane-2-carbonyl)benzonitrile; (4-iodophenyl)(6-(methyl(7H-pyrrolo[2,3-d]pyrimidin-4-yl)amino)-2-azaspiro[3.3]heptan-2-yl)methanone; (4-cyclopropylphenyl)(6-(methyl(7H-pyrrolo[2,3-d]pyrimidin-4-yl)amino)-2-azaspiro[3.3]heptan-2-yl)methanone; (4-ethynyl-3-methylphenyl)(6-(methyl(7H-pyrrolo[2,3-d]pyrimidin-4-yl)amino)-2-azaspiro[3.3]heptan-2-yl)methanone; (4-ethynyl-2-fluorophenyl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(4-(prop-1-yn-1-yl)phenyl)methanone; (2-chloro-4-ethynylphenyl)(6-(methyl(7H-pyrrolo[2,3-d]pyrimidin-4-yl)amino)-2-azaspiro[3.3]heptan-2-yl)methanone; 3-methyl-4-(6-(methyl(7H-pyrrolo[2,3-d]pyrimidin-4-yl)amino)-2-azaspiro[3.3]heptane-2-carbonyl)benzonitrile; (6-(methyl(7H-pyrrolo[2,3-d]pyrimidin-4-yl)amino)-2-azaspiro[3.3]heptan-2-yl)(1H-pyrazol-3-yl)methanone; (3-chloro-4-ethynylphenyl)(6-(methyl(7H-pyrrolo[2,3-d]pyrimidin-4-yl)amino)-2-azaspiro[3.3]heptan-2-yl)methanone; (4-ethynyl-3-fluorophenyl)(6-(methyl(7H-pyrrolo[2,3-d]pyrimidin-4-yl)amino)-2-azaspiro[3.3]heptan-2-yl)methanone; (5-ethynylpyridin-2-yl)(6-(methyl(7H-pyrrolo[2,3-d]pyrimidin-4-yl)amino)-2-azaspiro[3.3]heptan-2-yl)methanone; (6-(methyl(7H-pyrrolo[2,3-d]pyrimidin-4-yl)amino)-2-azaspiro[3.3]heptan-2-yl)(1-methyl-1H-benzo[d]imidazol-5-yl)methanone; (6-(methyl(7H-pyrrolo[2,3-d]pyrimidin-4-yl)amino)-2-azaspiro[3.3]heptan-2-yl)(1-methyl-1H-pyrazol-3-yl)methanone.2,5-difluoro-4-(6-(methyl(7H-pyrrolo[2,3-d]pyrimidin-4-yl)amino)-2-azaspiro[3.3]heptane-2-carbonyl)benzonitrile; 2,6-difluoro-4-(6-(methyl(7H-pyrrolo[2,3-d]pyrimidin-4-yl)amino)-2-azaspiro[3.3]heptane-2-carbonyl)benzonitrile; 2,3-difluoro-4-(6-(methyl(7H-pyrrolo[2,3-d]pyrimidin-4-yl)amino)-2-azaspiro[3.3]heptane-2-carbonyl)benzonitrile; 5-fluoro-2-methyl-4-(6-(methyl(7H-pyrrolo[2,3-d]pyrimidin-4-yl)amino)-2-azaspiro[3.3]heptane-2-carbonyl)benzonitrile; (2,3-difluorophenyl)(6-(methyl(7H-pyrrolo[2,3-d]pyrimidin-4-yl)amino)-2-azaspiro[3.3]heptan-2-yl)methanone; 3,5-difluoro-4-(6-(methyl(7H-pyrrolo[2,3-d]pyrimidin-4-yl)amino)-2-azaspiro[3.3]heptane-2-carbonyl)benzonitrile.2-Fluoro-5-{6-[methyl-(7H-pyrrolo[2,3-d]pyrimidin-4-yl)-amino]-2-aza-spiro[3.3]heptane-2-carbonyl}-benzonitrile; 3-Fluoro-5-{6-[methyl-(7H-pyrrolo[2,3-d]pyrimidin-4-yl)-amino]-2-aza-spiro[3.3]heptane-2-carbonyl}-benzonitrile; 2,5-Difluoro-4-{6-[methyl-(7H-pyrrolo[2,3-d]pyrimidin-4-yl)-amino]-2-aza-spiro[3.3]heptane-2-carbonyl}-benzonitrile; 2,3-Dichloro-4-{6-[methyl-(7H-pyrrolo[2,3-d]pyrimidin-4-yl)-amino]-2-aza-spiro[3.3]heptane-2-carbonyl}-benzonitrile; 2,3-Difluoro-5-{6-[methyl-(7H-pyrrolo[2,3-d]pyrimidin-4-yl)-amino]-2-aza-spiro[3.3]heptane-2-carbonyl}-benzonitrile; 3,4-Difluoro-5-{6-[methyl-(7H-pyrrolo[2,3-d]pyrimidin-4-yl)-amino]-2-aza-spiro[3.3]heptane-2-carbonyl}-benzonitrile; (4-Ethynyl-3-fluoro-phenyl)-{6-[-[(methyl-$d_3$)-(7H-pyrrolo[2,3-d]pyrimidin-4-yl)-amino]-2-aza-spiro[3.3]hept-2-yl}-methanone; 2-Fluoro-4-{6-[-[(methyl-$d_3$)-(7H-pyrrolo[2,3-d]pyrimidin-4-yl)-amino]-2-aza-spiro[3.3]heptane-2-carbonyl}-benzonitrile; (3-Fluoro-4-prop-1-ynyl-phenyl)-{6-[-[(methyl-$d_3$)-(7H-pyrrolo[2,3-d]pyrimidin-4-yl)-amino]-2-aza-spiro[3.3]hept-2-yl}-methanone; 2,3-Difluoro-4-{6-[-[(methyl-$d_3$)-(7H-pyrrolo[2,3-d]pyrimidin-4-yl)-amino]-2-aza-spiro[3.3]heptane-2-carbonyl}-benzonitrile; [4-(1-Methyl-1H-pyrazol-3-yl)-phenyl]-{6-[methyl-(7H-pyrrolo[2,3-d]pyrimidin-4-yl)-amino]-2-aza-spiro[3.3]hept-2-yl}-methanone; (1-Cyclopropyl-1H-pyrazol-4-yl)-{6-[methyl-(7H-pyrrolo[2,3-d]pyrimidin-4-yl)-amino]-2-aza-spiro[3.3]hept-2-yl}-methanone; 2,6-Difluoro-3-{6-[methyl-(7H-pyrrolo[2,3-d]pyrimidin-4-yl)-amino]-2-aza-spiro[3.3]heptane-2-carbonyl}-benzonitrile; N-(3-methoxy-1,2,4-thiadiazol-5-yl)-6-(methyl(7H-pyrrolo[2,3-d]pyrimidin-4-yl)amino)-2-azaspiro[3.3]heptane-2-carboxamide; 4-(6-(methyl(7H-pyrrolo[2,3-d]pyrimidin-4-yl)amino)-2-azaspiro[3.3]heptane-2-carbonyl)benzenesulfonamide; 1-{9-[Methyl-(7H-pyrrolo[2,3-d]pyrimidin-4-yl)-amino]-3-aza-spiro[5.5]undec-3-yl}-ethanone; (3-Ethanesulfonyl-3-aza-spiro[5.5]undec-9-yl)-methyl-(7H-pyrrolo[2,3-d]pyrimidin-4-yl)-amine; 2-Hydroxy-1-{9-[methyl-(7H-pyrrolo[2,3-d]pyrimidin-4-yl)-amino]-3-aza-spiro[5.5]undec-3-yl}-ethanone; 1-{9-[Methyl-(7H-pyrrolo[2,3-d]pyrimidin-4-yl)-amino]-3-aza-spiro[5.5]undec-3-yl}-propan-1-one; Methyl-(7H-pyrrolo[2,3-d]pyrimidin-4-yl)-[3-(2,2,2-trifluoro-ethyl)-3-aza-spiro[5.5]undec-9-yl]-amine; {9-[Methyl-(7H-pyrrolo[2,3-d]pyrimidin-4-yl)-amino]-3-aza-spiro[5.5]undec-3-yl}-pyridin-3-yl-methanone; 4-{9-[Methyl-(7H-pyrrolo[2,3-d]pyrimidin-4-yl)-amino]-3-aza-spiro[5.5]undec-3-yl}-4-oxo-butyronitrile; 4-{9-[Methyl-(7H-pyrrolo[2,3-d]pyrimidin-4-yl)-amino]-3-aza-spiro[5.5]undecane-3-carbonyl}-cyclohexanone; {9-[Methyl-(7H-pyrrolo[2,3-d]pyrimidin-4-yl)-amino]-3-aza-spiro[5.5]undec-3-yl}-(3-trifluoromethyl-phenyl)-methanone; 3-Fluoro-4-{9-[methyl-(7H-pyrrolo[2,3-d]pyrimidin-4-yl)-amino]-3-aza-spiro[5.5]undecane-3-carbonyl}-benzonitrile; 4-(2-{9-[Methyl-(7H-pyrrolo[2,3-d]pyrimidin-4-yl)-amino]-3-aza-spiro[5.5]undec-3-yl}-2-oxo-ethyl)-benzonitrile; 2-Fluoro-4-{9-[methyl-(7H-pyrrolo[2,3-d]pyrimidin-4-yl)-amino]-3-aza-spiro[5.5]undecane-3-carbonyl}-benzonitrile; {9-[Methyl-(7H-pyrrolo[2,3-d]pyrimidin-4-yl)-amino]-3-aza-spiro[5.5]undec-3-yl}-pyrazin-2-yl-methanone; 1-{9-[Methyl-(7H-pyrrolo[2,3-d]pyrimidin-4-yl)-amino]-3-aza-spiro[5.5]undecane-3-carbonyl}-cyclopropanecarbonitrile; (6-Methyl-pyrazin-2-yl)-{9-[methyl-(7H-pyrrolo[2,3-d]pyrimidin-4-yl)-amino]-3-aza-spiro[5.5]undec-3-yl}-methanone; 4,4,4-Trifluoro-1-{9-[methyl-(7H-pyrrolo[2,3-d]pyrimidin-4-yl)-amino]-3-aza-spiro[5.5]undec-3-yl}-butan-1-one; Benzo[b]thiophen-3-yl-{9-[methyl-(7H-pyrrolo[2,3-d]pyrimidin-4-yl)-amino]-3-aza-spiro[5.5]undec-3-yl}-methanone; 2-(1H-Indol-3-yl)-1-{9-[methyl-(7H-pyrrolo[2,3-d]pyrimidin-4-yl)-amino]-3-aza-spiro[5.5]undec-3-yl}-ethanone; {9-[Methyl-(7H-pyrrolo[2,3-d]pyrimidin-4-yl)-amino]-3-aza-spiro[5.5]undec-3-yl}-(3-methyl-thiophen-2-yl)-methanone; (1H-Indol-2-yl)-{9-[methyl-(7H-pyrrolo[2,3-d]pyrimidin-4-yl)-amino]-3-aza-spiro[5.5]undec-3-yl}-methanone; 2-Methylamino-1-{9-[methyl-(7H-pyrrolo[2,3-d]pyrimidin-4-yl)-amino]-3-aza-spiro[5.5]undec-3-yl}-ethanone; Cyclopropyl-{9-[methyl-(7H-pyrrolo[2,3-d]pyrimidin-4-yl)-amino]-3-aza-spiro[5.5]undec-3-yl}-methanone 1-{9-[Methyl-(7H-pyrrolo[2,3-d]pyrimidin-4-yl)-amino]-3-aza-spiro[5.5]undec-3-yl}-butan-1-one; {9-[Methyl-(7H-pyrrolo[2,3-d]pyrimidin-4-yl)-amino]-3-aza-spiro[5.5]undec-3-yl}-(3-trifluoromethoxy-phenyl)-methanone; 3-{9-[Methyl-(7H-pyrrolo[2,3-d]pyrimidin-4-yl)-amino]-3-aza-spiro[5.5]undecane-3-carbonyl}-benzonitrile; 9-[Methyl-(7H-pyrrolo[2,3-d]pyrimidin-4-yl)-amino]-3-aza-spiro[5.5]undecane-3-carboxylic acid ethyl ester; Methyl-(7H-pyrrolo[2,3-d]pyrimidin-4-yl)-[3-(2,2,2-trifluoro-ethanesulfonyl)-3-aza-spiro[5.5]undec-9-yl]-amine; 3-{9-[Methyl-(7H-pyrrolo[2,3-d]pyrimidin-4-yl)-amino]-3-aza-spiro[5.5]undec-3-yl}-3-oxo-propionitrile; Benzo[b]thiophen-2-yl- {9-[methyl-(7H-pyrrolo[2,3-d]pyrimidin-4-yl)-amino]-3-aza-spiro[5.5]undec-3-yl}-methanone; tert-butyl 9-(methyl (7H-pyrrolo[2,3-d]pyrimidin-4-yl)amino)-3-azaspiro[5.5] undecane-3-carboxylate; 2-methoxy-1-(9-(methyl(7H-pyrrolo[2,3-d]pyrimidin-4-yl)amino)-3-azaspiro[5.5] undecan-3-yl)ethan-1-one; 1-(9-(methyl(7H-pyrrolo[2,3-d]pyrimidin-4-yl)amino)-3-azaspiro[5.5]undecan-3-yl)-2-phenoxyethan-1-one; 2,2,2-trifluoroethyl 9-(methyl(7H-pyrrolo[2,3-d]pyrimidin-4-yl)amino)-3-azaspiro[5.5] undecane-3-carboxylate; N-(3-methoxy-1,2,4-thiadiazol-5-yl)-9-(methyl(7H-pyrrolo[2,3-d]pyrimidin-4-yl)amino)-3-azaspiro[5.5]undecane-3-carboxamide; 9-(methyl(7H-pyrrolo[2,3-d]pyrimidin-4-yl)amino)-N-(2,2,2-trifluoroethyl)-3-azaspiro[5.5]undecane-3-carboxamide; N-methyl-9-(methyl(7H-pyrrolo[2,3-d]pyrimidin-4-yl) amino)-3-azaspiro[5.5]undecane-3-carboxamide; N,N-diethyl-9-(methyl(7H-pyrrolo[2,3-d]pyrimidin-4-yl)amino)-3-azaspiro[5.5]undecane-3-sulfonamide; 4-(9-(methyl(7H-pyrrolo[2,3-d]pyrimidin-4-yl)amino)-3-azaspiro[5.5] undecane-3-carbonyl)benzenesulfonamide; 3-(9-(methyl (7H-pyrrolo[2,3-d]pyrimidin-4-yl)amino)-3-azaspiro[5.5] undecan-3-yl)-3-oxopropane-1-sulfonamide; 3-fluoro-5-(2-(9-(methyl(7H-pyrrolo[2,3-d]pyrimidin-4-yl)amino)-3-azaspiro[5.5]undecan-3-yl)-2-oxoethoxy)benzonitrile; 4-(2-(9-(methyl(7H-pyrrolo[2,3-d]pyrimidin-4-yl)amino)-3-azaspiro[5.5]undecan-3-yl)-2-oxoethoxy)benzonitrile; 3-(2-(9-(methyl(7H-pyrrolo[2,3-d]pyrimidin-4-yl)amino)-3-azaspiro[5.5]undecan-3-yl)-2-oxoethoxy)benzonitrile; 2-fluoro-4-(2-(9-(methyl(7H-pyrrolo[2,3-d]pyrimidin-4-yl) amino)-3-azaspiro[5.5]undecan-3-yl)-2-oxoethoxy)benzonitrile; 2,3-difluoro-4-(2-(9-(methyl(7H-pyrrolo[2,3-d]pyrimidin-4-yl)amino)-3-azaspiro[5.5]undecan-3-yl)-2-oxoethoxy)benzonitrile; N-(4-methoxyphenyl)-9-(methyl (7H-pyrrolo[2,3-d]pyrimidin-4-yl)amino)-3-azaspiro[5.5] undecane-3-carboxamide; N-(3-methoxyphenyl)-9-(methyl (7H-pyrrolo[2,3-d]pyrimidin-4-yl)amino)-3-azaspiro[5.5] undecane-3-carboxamide; N-(4-cyanophenyl)-9-(methyl (7H-pyrrolo[2,3-d]pyrimidin-4-yl)amino)-3-azaspiro[5.5] undecane-3-carboxamide; N-(3-cyanophenyl)-9-(methyl (7H-pyrrolo[2,3-d]pyrimidin-4-yl)amino)-3-azaspiro[5.5] undecane-3-carboxamide; N-(6-cyanopyridin-2-yl)-9-(methyl(7H-pyrrolo[2,3-d]pyrimidin-4-yl)amino)-3-azaspiro[5.5]undecane-3-carboxamide; N-(6-methoxypyridin-2-yl)-9-(methyl(7H-pyrrolo[2,3-d] pyrimidin-4-yl)amino)-3-azaspiro[5.5]undecane-3-carboxamide; N-(5-cyanopyridin-2-yl)-9-(methyl(7H-pyrrolo[2,3-d]pyrimidin-4-yl)amino)-3-azaspiro[5.5] undecane-3-carboxamide; 9-(methyl(7H-pyrrolo[2,3-d] pyrimidin-4-yl)amino)-N-(5-methylthiazol-2-yl)-3-azaspiro [5.5]undecane-3-carboxamide; 9-(methyl(7H-pyrrolo[2,3-d]pyrimidin-4-yl)amino)-N-(1-methyl-1H-pyrazol-3-yl)-3-azaspiro[5.5]undecane-3-carboxamide; 9-(methyl(7H-pyrrolo[2,3-d]pyrimidin-4-yl)amino)-N-(5-methylpyrazin-2-yl)-3-azaspiro[5.5]undecane-3-carboxamide; N-(5-methoxypyrazin-2-yl)-9-(methyl(7H-pyrrolo[2,3-d] pyrimidin-4-yl)amino)-3-azaspiro[5.5]undecane-3-carboxamide; N-(5-methoxypyridin-2-yl)-9-(methyl(7H-pyrrolo[2,3-d]pyrimidin-4-yl)amino)-3-azaspiro[5.5] undecane-3-carboxamide; N-(5-fluorothiazol-2-yl)-9-(methyl(7H-pyrrolo[2,3-d]pyrimidin-4-yl)amino)-3-azaspiro[5.5]undecane-3-carboxamide; N-(5-chlorothiazol-2-yl)-9-(methyl(7H-pyrrolo[2,3-d]pyrimidin-4-yl)amino)-3-azaspiro[5.5]undecane-3-carboxamide; N-(5-cyanothiazol-2-yl)-9-(methyl(7H-pyrrolo[2,3-d]pyrimidin-4-yl)amino)-3-azaspiro[5.5]undecane-3-carboxamide; 9-(methyl(7H-pyrrolo[2,3-d]pyrimidin-4-yl)amino)-N-(thiazol-2-yl)-3-azaspiro[5.5]undecane-3-carboxamide; and N-(5-methoxythiazolo[5,4-b]pyridin-2-yl)-9-(methyl(7H-pyrrolo[2,3-d]pyrimidin-4-yl)amino)-3-azaspiro[5.5]undecane-3-carboxamide.

11. A pharmaceutical composition comprising a therapeutically effective amount of the compound of formula (I) of claim 1, and a pharmaceutically acceptable excipient.

12. A method for treating an autoimmune disease, cancers, tumors, inflammatory diseases, or immunologically mediated diseases comprising administering to a subject in need thereof a composition containing a therapeutically effective amount of the compound of formula (I) of claim 1 and other therapeutic agents.

13. The method of claim 12, which is administered in combination with a therapeutic agent selected from the group consisting of: anticancer drugs, steroid drugs, methotrexates, leflunomides, anti-TNFa agents, calcineurin inhibitors, antihistaminic drugs, and a mixture thereof.

14. A compound selected from the group consisting of 1-(6-(methyl(7H-pyrrolo[2,3-d]pyrimidin-4-yl)amino)-2-azaspiro[3.3]heptan-2-yl)-3-(methylsulfonyl)propan-1-one; 3-methanesulfonyl-1-{9-[methyl-(7H-pyrrolo[2,3-d]pyrimidin-4-yl)-amino]-3-aza-spiro[5.5]undec-3-yl}-propan-1-one; (6,7-dihydro-5H-pyrrolo[2,3-d]pyrimidin-4-yl)-methyl-[3-(propane-1-sulfonyl)-3-aza-spiro[5.5]undec-9-yl]-amine; and 9-[(6,7-dihydro-5H-pyrrolo[2,3-d] pyrimidin-4-yl)-methyl-amino]-3-aza-spiro[5.5]undecane-3-carboxylic acid isopropyl ester.

\* \* \* \* \*